(12) United States Patent
Qiu et al.

(10) Patent No.: US 8,841,512 B2
(45) Date of Patent: Sep. 23, 2014

(54) **FLAX (*LINUM USITATISSIMUM* L.) SEED-SPECIFIC PROMOTORS**

(75) Inventors: Xiao Qiu, Saskatoon (CA); Martin Truksa, Saskatoon (CA); Zhiyuan Hu, Apex, NC (US)

(73) Assignee: Bioriginal Food & Science Corporation, Saskatoon (CA)

(*) Notice: Subject to any disclaimer, the term of this patent is extended or adjusted under 35 U.S.C. 154(b) by 761 days.

(21) Appl. No.: 12/336,184

(22) Filed: Dec. 16, 2008

(65) Prior Publication Data
US 2009/0172835 A1    Jul. 2, 2009

Related U.S. Application Data

(62) Division of application No. 11/655,545, filed on Jan. 19, 2007, now Pat. No. 7,473,820, which is a division of application No. 10/165,289, filed on Jun. 6, 2002, now Pat. No. 7,193,134.

(60) Provisional application No. 60/295,823, filed on Jun. 6, 2001.

(51) Int. Cl.
| | |
|---|---|
| *C12N 15/82* | (2006.01) |
| *A01H 5/00* | (2006.01) |
| *C12N 5/10* | (2006.01) |
| *C07H 21/04* | (2006.01) |
| *C07K 14/415* | (2006.01) |

(52) U.S. Cl.
CPC .......... *C12N 15/8234* (2013.01); *C07K 14/415* (2013.01); *C12N 15/8247* (2013.01)
USPC ........... 800/281; 800/298; 800/320; 435/419; 435/320.1; 536/24.1

(58) Field of Classification Search
None
See application file for complete search history.

(56) References Cited

U.S. PATENT DOCUMENTS

| | | |
|---|---|---|
| 6,777,591 B1 | 8/2004 | Chaudhary et al. |
| 7,642,346 B2 * | 1/2010 | Chaudhary et al. .......... 536/24.1 |

FOREIGN PATENT DOCUMENTS

| | | |
|---|---|---|
| JP | 408173167 | 7/1996 |
| WO | WO-94/18337 A1 | 8/1994 |
| WO | WO-98/18948 A1 | 5/1998 |
| WO | WO-01/16340 A1 | 3/2001 |

OTHER PUBLICATIONS

Kim et al, Plant Molecular Biology 24: 105-117, 1994.*
Fourgoux-Nicol et al, Plant Mol Biol 40:857-872, 1999.*
"cDNA Encoding Omega3-Linoleic Acid Desaturase Llocalized in Microsome", EMBL Database, Accession No. E11610, Jul. 9, 2006.
Alonso, D. L., et al., "Plants as 'Chemical Factories' for the Production of Polyunsaturated Fatty Acids", Biotechnol. Adv., 2000, vol. 18, No. 6, pp, 481-497.
"Perilla Frutescens Omega-3 Fatty Acid Desaturase (FAD3) mRNA, Complete cds.", EMBL Database, Accession No. AF047039, Mar. 11, 1999.
"Omega-3 fatty acid desaturase", EMBL Database, Accession No. Q9ZPP7, May 1, 1999.
"Pelargonium x Hortorum Omega-3 Desaturase (pxh-15) mRNA, Partial cds.", EMBL Database, Accession No. AF020204, May 18, 1998.
"Omega-3 Desaturase", EMBL Database, Accession No. O64907, Aug. 1, 1998.
"*L. usitatissimum* mRNA for Stearoyl-(Acyl-Carrier-Protein) Desaturase", EMBL Database, Accession No. X70962, Feb. 16, 1993.
Singh, S., et al., "Sequence of a cDNA from *Linum usitatissimum* eEncoding the Stearoyl-Acyl Carrier Protein Desaturase", Plant Physiiol., 1994, vol. 104, No. 3, p. 1075.
Anderson, P. A., et al., "Inactivation of the Flax Rust Resistance Gene M Associated with Loss of a Repeated Unit within the Leucine-Rich Repeat Coding Region", The Plant Cell, 1997, vol. 9, No. 4, pp. 641-651.
Kalh, G, "The Dictionary of Gene Technology, Genomics, Transcriptornics, Proteomics", Second Edition, Wiley-VCH, 2001, p. 855.
Madhusudhan, K. T., et al., "Isolation and Characterization of a Small Molecular Weight Protein of Linseed Meal", Phytochemistry, 1985, vol. 24, No. 11, pp. 2507-2509.
Vrinten, P., et al., "Two *FAD* 3 Desaturase Genes Control the Level of Linolenic Acid in Flax Seed", Plant Physiology, 2005, vol. 139, pp. 79-87.
Yadav, N. S., et al., "Cloning of Higher Plant ω-3 Fatty Acid Desaturases", Plant Physiology, 1993, vol. 103, pp. 467-476.
European Search Report for Application No. 08003928.2-1212, dated Apr. 29, 2008.
Kim, Y., et al., "A 20 Nucleotide Upstream Element is Essential for the Nopaline Synthase (*nos*) Promoter Activity", Plant Molecular Biology, 1994, vol. 24, pp. 105-117.
Hauschild, K., et al., "Isolation and Analysis of the Gene *bbe*1 Encoding the Berberine Bridge Enzyme from the California Poppy *Eshscholzia californica*", Plant Molecular Biololgy, 1998, vol. 36, pp. 473-478.
Hannenhalli, S., et al., "Promoter Prediction in the Human Genome", Bioinformatics, 2001, vol. 17, Suppl. 1, pp. S90-S96.
Qiu, X., et al., "Expression of Borage Δ6 Desaturase in *Saccharomyces cerevisiae* and Oilseed Crops", Canadian J. Botany, 2002, vol. 80, No. 1, pp. 42-49.
Facchini, P. J., "Expression Patterns Conferred by Tyrosine/Dihydroxyphenylalanine Decarboxylase Promoters from Opium Poppy Are Conserved in Transgenic Tobacco", Plant Physiol., 1998, vol. 118, pp. 69-81.
Jain, R. K., et al., "Isolation and Characterization of Two Promoters from Linseed for Genetic Engineering", Crop Science, 1999, vol. 39, pp. 1696-1701.
Truksa, M., et al., "Molecular Analysis of Flax 2S Storage Protein Conlinin and Seed Specific Activity of its Promoter", Plant Physiology and Biochemistry, 2003, vol. 41, No. 2, pp. 141-147.

* cited by examiner

*Primary Examiner* — Elizabeth McElwain
(74) *Attorney, Agent, or Firm* — Drinker Biddle & Reath LLP

(57) ABSTRACT

The present invention is directed to promoters of flax conlinin and ω-3 desaturase genes. The promoters guide high levels of the expression exclusively in flax developing seeds. This specific expression pattern concomitant with the biosynthesis of storage lipids and proteins make these promoters particularly useful for seed-specific modification of fatty acid and protein compositions in plant seeds.

18 Claims, 30 Drawing Sheets

***Conlinin 1* cDNA; 673 bases**

GAAAAACCAATCATAACCAAAATGGCAAAGCTGATGAGCCTAGCAGCCGT
AGCAACGGCATTCCTCTTCCTCATTGTGGTGGACGCATCCGTCCGAACCA
CAGTGATCATCGACGAGGACACCAACCAAGGCCGCGGTGGCCAAGGTGGG
CAAGGACAGCAGCAGCAATGCGAGAAGCAGATCCAGGAGCAAGACTACCT
GAGGAGCTGCCAGCAGTTCCTGTGGGAGAAAGTCCAGAAGGGCGGCCGCA
GCTACTACTACAACCAAGGCCGTGGAGGAGGGCAACAGAGCCAGCACTTC
GATAGCTGCTGCGATGATCTTAAGCAATTGAGGAGCGAGTGCACATGCAG
GGGACTGGAGCGTGCAATCGGCCAGATGAGGCAGGACATCCAGCAGCAGG
GACAGCAGCAGGAAGTTGAGAGGTGGGTCCAGCAAGCTAAACAAGTCGCT
AGGGACCTTCCGGGACAGTGCGGCACCCAGCCTAGCCGATGCCAGCTCCA
GGGGCAGCAGCAGTCTGCATGGTTTTGAAGTGGTGATCGATGAGATCGTA
TAAAGACACTTGCTAGGTGTTAAGGATGGGATAATAAGATGTGTTTTAAG
TCATTAACCCGTAATTAAAAGGAGAGAGAGCTTGATGGAATGGTATTGAT
GTTCCTTGGGTTTTAAAAAAAAA (SEQ ID NO: 1)

Figure 1

> CONLININ 1 protein; 168 amino acids.

MAKLMSLAAVATAFLFLIVVDASVRTTVIIDEDTNQGRGGQGGQGQQQQCEKQIQEQDYLRSCQ
QFLWEKVQKGGRSYYYNQGRGGGQQSQHFDSCCDDLKQLRSECTCRGLERAIGQMRQDIQQQG
QQQEVERWVQQAKQVARDLPGQCGTQPSRCQLQGQQQSAWF (SEQ ID NO: 2)

Figure 2

>*Conlinin 2* cDNA; 676 bases

AAGAACCAATCACCACCAAAAAATGGCAAAGCTGATGAGCCTGGCAGCCG
TAGCAACGGCATTCCTCTTCCTGATCGTGGTGGACGCATCCGTCCGAACC
ACAGTGATTATCGACGAGGAGACCAACCAAGGCCGCGGTGGAGGCCAAGG
TGGCCAGGGACAGCAGCAGTCTTGCGAGCAGCAGATCCAGCAGCAAGACT
TCCTGAGGAGCTGCCAGCAGTTCATGTGGGAGAAAGTCCAGAGGGGCGGC
CGCAGCCACTATTACAACCAGGGCCGTGGAGGAGGCGAACAGAGCCAGTA
CTTCGACAGCTGTTGTGACGACCTTAAGCAATTGAGCACCGGGTGCACAT
GCAGGGGACTTGAGCGTGCCATCGGCCAAATGAGGCAGGAAATCCAGCAG
CAGGGACAGCAGCAGGAAGTTCAGAGGTGGATCCAGCAAGCTAAACAAAT
CGCTAAGGACCTCCCCGGACAGTGCCGACCCAGCCTAGCCAATGCCAGTT
CCAGGGCCAGCAGCAATCTGCATGGTTTTGAAGGGGTGATCGATTATGAG
ATCGTACAAGACACTGCTAGGTGTTAAGGATGGATAATAATAATAATAA
TGAGATGGATGTGTTTTAAGTTAATGTAACAGCTTAATAAAGAGAGAGAG
AGAGAGAGAGAGAGAGTCAAAAAA (SEQ ID NO: 3)

Figure 3

> CONLININ 2 protein; 169 amino acids.

MAKLMSLAAVATAFLFLIVVDASVRTTVIIDEETNQGRGGGQGGQGQQQSCEQQ
IQQQDFLRSCQQFMWEKVQRGGRSHYYNQGRGGGEQSQYFDSCCDDLKQLSTG
CTCRGLERAIGQMRQEIQQQGQQQEVQRWIQQAKQIAKDLPGQCRTQPSQCQFQ
GQQQSAWF (SEQ ID NO: 4)

Figure 4

```
                                        start
Con11   1  GAAAAACCAATCATAACC...AAAATGGCAAAGCTGATGAGCCTAGCAGCCGTAGCAACGG
Con12   1  AAGAACCAATCACCACCAAAAAATGGCAAAGCTGATGAGCCTGGCAGCCGTAGCAACGG Con11  59  CATTCCTCTTCCTCATTGTGGTGGACGCATCCGTCCGAACCACAGTGATCATCGACGAGG
Con12  60  CATTCCTCTTCCTGATCGTGGTGGACGCATCCGTCCGAACCACAGTGATTATCGACGAGG Con11 119  ACACCAACCAAGGCCGCGGT...GGCCAAGGTGGGCAAGGACAGCAGCAGCAATGCGAGA
Con12 120  AGACCAACCAAGGCCGCGGTGGAGGCCAAGGTGGCCAGGGACAGCAGCAGTCTTGCGACC Con11 176  AGCAGATCCAGCAGCAAGACTACCTGAGGAGCTGCCAGCAGTTCCTGTGGGAGAAAGTCC
Con12 180  AGCAGATCCAGCAGCAAGACTTCCTGAGGAGCTGCCAGCAGTTCATGTGGGAGAAAGTCC Con11 236  AGAAGGGCGGCCGCAGCTACTACTACAACCAAGGCCGTGGAGGAGGGCAACAGAGCCAGC
Con12 240  AGAGGGGCGGCCGCAGCCACTATTACAACCAGGGCCGTGGAGGAGGCGAACAGAGCCAGT Con11 296  ACTTCGATAGCTGCTGCGATGATCTTAAGCAATTGAGGAGCGAGTGCACATGCAGGGGAC
Con12 300  ACTTCGACAGCTGTTGTGACGACCTTAAGCAATTGAGCACCGGGTGCACATGCAGGGGAC Con11 356  TGGAGCGTGCAATCGGCCAGATGAGGCAGGACATCCAGCAGCAGGGACAGCAGCAGGAAG
Con12 360  TTGAGCCTGCCATCGGCCAAATGAGGCAGGAAATCCAGCAGCAGGGACAGCAGCAGGAAG Con11 416  TTGAGAGGTGGGTCCAGCAAGCTAAACAAGTCGCTAGGGACCTTCCGGGACAGTGCCGCA
Con12 420  TTCAGAGGTGGATCCAGCAAGCTAAACAAATCGCTAAGGACCTCCCCGGACAGTGCCGCA stop
Con11 476  CCCAGCCTAGCCGATGCCAGCTCCAGGGGCAGCAGCAGTCTGCATGGTTTTGAAGTGGTG
Con12 480  CCCAGCCTAGCCAATGCCAGTTCCAGGGCCAGCAGCAATCTGCATGGTTTTGAAGGGGTG Con11 536  ATCG...ATGAGATCGTATAAAGACACTTGCTAGGTGTTAAGGATGGGATAATAAGATGT
Con12 540  ATCGATTATGAGATCGTACAAAGACAC.TGCTAGGTGTTAAGGATGGATAATAATAATAA Con11 593  GTTTTAAGTCATTAACCCGTAATTAAAAGGAGAGAGAGCTTGATGGAATGGTATTCCATG
Con12 599  TAATGAGATGGATGTGTTTAAGTTAATGTAACAGCTCTAATAAAGAGAGAGAGAGAGAG Con11 653  TTCCCTTGGGTTTTAAAAAAAAAA
Con12 659  AGAGAGAGAGAGGCTGAAAAAAAA
```

Figure 5

```
CONL1  MAKLMSLAAVATAFLFLIVVDASVRTTVIIDEDTNQGP.GGQGGQGQQQQCEKQIQEQDY
CONL2  MAKLMSLAAVATAFLFLIVVDASVRTTVIIDEETNQGRGGGQGGQGQQQSCEQQIQQQDF

CONL1  LRSCQQFMWEKVQRGGRSHYYNQGRGGGEQSQYFDSCCDDLKQLSTGCTCRGLERAIGQM
CONL2  LRSCQQFLWEKVQKGGRSYYYNQGRGGGQQSQHFDSCCDDLKQLRSECTCRGLERAIGQM

CONL1  RQEIQQGQQQEVQRWIQQAKQIAKDLPGQCRTQPSQCQFQGQQQSAWF
CONL2  RQDIQQGQQQEVERWVQQAKQVARDLPGQCGTQPSRCQLQGQQQSAWF
```

Figure 6

```
CONLININ 1    1 MAKLMSLAAVATAFLFLTVVDASVRTTVIIDEDTNQGRGGQGGQGQQQC 50
                || : |    |   ||:  .   || |   |||          | .|.|
    At2S2     1 MANKLFLVCATFALCFLLTNASIYRTVVEFDED.....DASNPMGPRQKC 45

CONLININ 1   51 EKQIQEQDYLRSCQQFLWEKVQK...GGRSY........YYNQGRGGGQQ 89
                :|: |: :||.||. :   ....   || |              .| |
    At2S2    46 QKEFQQSQHLRACQKLMRMQMRQGRGGGPSLDDEFDLEDDIENPQGPQQG 95

CONLININ 1   90 SQHFDSCCDDLKQLRSECTCRGLERAIGQMRQDIQQQGQQQEVERWVQQA 139
                |    || :|:|   ||  | .|     . :  |||    :   ..
    At2S2    96 HQILQQCCSELRQEEPVGVCPTLRQA....ARAVSLQGQHGPFQS..RKI 139

CONLININ 1  140 KQVARDLPGQCGTQP.SRCQLQ 160
                 .|: ||   |   |    |  |
    At2S2   140 YKTAKYLPNICKIQQVGECPFQ 161

Notes: MAKLMSLAAVATAFLFLTVVDA - predicted signal peptide
```

Figure 7

> *Conlinin Promoter 1 Sequence*

CAACGGTTCCGGCGGTATAGAGTTGGGTAATTCGAAACCGCACAGATCCA
ATTCGATTAGCAGATATTTGGTGTCTAAATGTTTATTTTGTGATATGTTC
ATGTTTGAAATGGTGGTTTCGAAACCAGGGACAACGTTGGGATCTGATAG
GGTGTCAAAGAGTATTATGGATTGGGACAATTTCGGTCATGAGTTGCAAA
TTCAAGTATATCGTTCGATTATGAAAATTTTCGAAGAATATCCCATTTGA
GAGAGTCTTTACCTCATTAATGTTTTTAGATTATGAAATTTTATCATAGT
TCATCGTAGTCTTTTTGGTGTAAAGGCTGTAAAAGAAATTGTTCACTTT
TGTTTTCGTTTATGTGAAGGCTGTAAAAGATTGTAAAGACTATTTTGGT
GTTTTGGATAAAATGATAGTTTTTATAGATTCTTTTGCTTTTAGAAGAAA
TACATTTGAAATTTTTTCCATGTTGAGTATAAAATACCGAAATCGATTGA
AGATCATAGAAATATTTTAACTGAAAACAAATTTATAACTGATTCAATTC
TCTCCATTTTTATACCTATTTAACCGTAATCGATTCTAATAGATGATCGA
TTTTTTATATAATCCTAATTAACCAACGGCATGTATGGATAATTAACCGA
TCAACTCTCACCCCTAATAGAATCAGTATTTTCCTTCGACGTTAATTGAT
CCTACACTATGTAGGTCATATCCATCGTTTTAATTTTTGGCCACCATTCA
ATTCTGTCTTGCCTTTAGGGATGTGAATATGAACGGCCAAGGTAAGAGAA
TAAAATAATCCAAATTAAAGCAAGAGAGGCCAAGTAAGATAATCCAAAT
GTACACTTGTCATTGCCAAAATTAGTAAATACTCGGCATATTGTATTCC
CACACATTATTAAAATACCGTATATGTATTGGCTGCATTTGCATGAATAA
TACTACGTGTAAGCCCAAAAGAACCCACGTGTAGCCCATGCAAAGTTAAC
ACTCACGACCCCATTCCTCAGTCTCCACTATATAAACCCACCATCCCCAA
TCTCACCAAACCCACCACACAACTCACAACTCACTCTCACACCTTAAAGA
ACCAATCACCACCAAAAAATG (SEQ ID NO:5)

Figure 8

\> Conlinin Promoter 2 sequence

AACTGATATATATTACTTTGTTGGTTGGTTAATAGATTAACCTATTTTTCATAAAATTATAATTAATAAAA
AAATTGAGTTTTTGAAATTTTGAGCTTTCTTGTATTATGTTGGAACTTCTTGTTCCATTGCAATAAAATCA
GTTATAAAAAAATTACAAACGAAGTGCACTCAGTAATTAACCACCTCAAACAGACTCTCACTTACTCATAG
TAGGATCAATATTTTCCTTCGGCGATAATCGTTCCTCCACTATGTAGGTCATTATTTTAATTTTTGGTGAT
TTATTATGTGTCTAATTTTAAAAATTAATTATTCGATAAATATTACTTTTATGTATTGTTAGTTTGTTTTG
GAATTTTAAAGTTTGAGTTGGTCTTAAGAGTTATCTTGTTTAACCGATATTAATTGTAATACTAGAAAAAT
AAAGCTTATAAAAAACCTTTTATTTGTACATAGATAGGGGAATCGAAGAAGAAAAAAATTCAAAGTTTAAA
TTATTTATTTTATATTTATGTTATTTACTTTAAATTTTCTAATTTCTATTAAATATTAATCATATACGTCA
AAGCGTAATATAATGGGCACCTTACACAAACATTCGATAGAAGGGATGTGAATATGAAGGGACCAAAGTGA
GATCTTGCCCTCAGCTCCTAGTGCGCCTCTTGCTGTTGCTCCACGTGTTAATCCAAGTGGCGAGAAAAGGA
GAATAATAACGCAAAAAAACAGGCCAAGTAAGATAATCCAAGTGTACACTTGTCATCGCCAAACTTACTAA
AATACGCGGCAAATTGTATACCCACACATTATTACCATACCATATATTGGCTGCATTTGCATGTATAATAC
TACGTGTAAGCTCAGAAAATTCCACGTGTCGCCCATGCAAAATTAACACTCACGACCCATTCCTAAATCTC
CACTATATAAACCCCCACTCCCCCATCTTACCAAACCCACCACACAACTCACAACTTAGAAAAACCAATCA
TAACCAAAATGGCAAAGCTGATG (SEQ ID NO: 6)

Figure 9

> *LuFad3* cDNA sequence

```
CAAAAATATATATTGGGTTTGTTTGGTGCAGATTACAGTG    40
ACTTCAAAACTGTGGCTCTGCACGACCAAACTATGAGCCC    80
TCCAAACTCAATGAGTCCCGCCACCAACGGCAGCACCAAT   120
GGTGTGGCTATCAATGGGGCGAAGAAGCTACTCGATTTCG   160
ACCCGAGTGCTGCTCCCCCTTTCAAGATTGCAGACATCCG   200
TGCTGCAATCCCGCCGCATTGTTGGGTGAAGAACCCCTGG   240
AGGTCACTCAGCTACGTCCTGAGAGACCTCCTGGTCATCC   280
TCAGCTTCGCCGTTGCGGCGACAAAGCTGGACAGCTGGAC   320
TGTCTGGCCTCTCTACTGGATTGCTCAAGGAACCATGTTC   360
TGGGCAGTCTTTGTTCTTGGACATGATTGTGGCCATGGGA   400
GCTTCTCAGACAGTTGGTTGTTGAACAACGTGATGGGACA   440
TATACTCCATTCCTCAATCCTCGTACCTTACCATGGATGG   480
AGAATTAGCCACAAGACCCATCACCAGAATCACGGCAATG   520
TGGAGAAAGATGAATCCTGGGTTCCACTGCCGGAGAAGGT   560
GTACAAGAGCTTGGATACCGGCACCAAGTTCATGAGGTTC   600
ACCATCCCTCTCCCAATGTTTGCGTATCCTATCTACTTGT   640
GGAGGAGAAGTCCGGGGAAGAAAGGGTCGCATTTCAACCC   680
ATACAGTGACCTGTTCGCACCGAACGAGAGGACATCGGTC   720
ATGATTTCGACATTGTGCTGGACAGCCATGGCCTTACTCC   760
TCTGCTACTCATCGTTCATCTACGGCTTCCTTCCGGTCTT   800
CAAAATCTACGGCGTCCCTTATCTAATATTCGTGGCGTGG   840
CTCGACATGGTGACCTACCTTCACCACCACGGGTACGAGC   880
AGAAGCTGCCGTGGTACAGAGGCAAAGAGTGGAGCTACCT   920
ACGTGGAGGGCTGACGACCGTCGATCGAGATTACGGGGTC   960
ATCAACAACATCCACCATGACATTGGCACCCATGTTATTC  1000
ACCATCTCTTCCCTCAAATGCCACACTATCACCTAGTCGA  1040
AGCGACTCAGGCAGCGAAGCACGTGCTGGGGAAGTACTAC  1080
AGAGAACCGAAGAAATCAGGGCCTTTCCCATTCCACTTGT  1120
TTGGGTACTTGGTGAGGAGCCTGGGCGAGGATCACTACGT  1160
TAGCGATACAGGCGACGTCGTTTTCTATCAATCTGACCCA  1200
CATATTCCCAAGTTCCCTACCAGTGCCACCACCAAGTCCA  1240
AATCTAGCTGATGATATTGGCTCTGATCTGATGTATGCTG  1280
CAGGCTGTTTTATTTTGTCCTTTGTTCGTTTCTTTCTGCC  1320
AGAAACAAATTCTCTGTTTCTATGTTTCTCTGTCTCTCCC  1360
ACCCCAGCTTTCTTTCTGAGTATATCGTATAAAGTTTCAA  1400
GTGATTGTAAGAGCAGAAAAGAAAGAAGAAGAAGAATAA   1440
TAAAGAGGATTGGCAACAAAAAAAAAAAAAAAAA        1475
(SEQ ID NO: 7)
```

Figure 14

➢ LuFAD3 protein sequence, 392 aa

MSPPNSMSPATNGSTNGVAINGAKKLLDFDPSAAPPFKIADIRAAIPPHCWVKNPWRSLSYVLRDLLVILS
FAVAATKLDSWTVWPLYWIAQGTMFWAVFVLGHDCGHGSFSDSWLLNNVMGHILHSSILVPYHGWRISHKT
HHQNHGNVEKDESWVPLPEKVYKSLDTGTKFMRFTIPLPMFAYPIYLWRRSPGKKGSHFNPYSDLFAPNER
TSVMISTLCWTAMALLLCYSSFIYGFLPVFKIYGVPYLIFVAWLDMVTYLHHHGYEQKLPWYRGKEWSYLR
GGLTTVDRDYGVINNIHHDIGTHVIHHLFPQMPHYHLVEATQAAKHVLGKYYREPKKSGPFPFHLFGYLVR
SLGEDHYVSDTGDVVFYQSDPHIPKFPTSATTKSKSS (SEQ ID NO:8)

Figure 15

➤ Normandy *LuFad3* promoter sequence

```
ACTACCTGCAAACCAAAACAGATTCATGGCCAAGCTTATT    40
CCCACAAAAGGGTCCAAACAAAAGGAAAATGGTCTGATTG    80
TCTGCTAAAGTTTATTGATCAGTACGTGGGTGGATGTTTT   120
GTTCACCTTTACAGTGCCATTCTTTACCACAGTTGTTACC   160
AGCATCACTCATCATCATCAGCATCATTAATCCTTAGTTT   200
TCTATGCACTCACTTTCATTAGTGTTCACTTTGCAATTCA   240
ATAATCCATCTATTATTCGATTGCAAAGCAAGAGAGTTGT   280
AAGAGTTTCGACTAAGTTCAAATGGAGCCCAAAGTTTGAT   320
CATCAGTTTGTGAAAACAAAGTCAAGCTCGTCCATATCTC   360
TGCCTTGTTCCCAACCCACTACATAGCATCTGGAAGACCT   400
CGTACTTCACATTCTCGGACCGAAGGACAACCAATACCCC   440
CCTTGTGATCCTAAACACATGCACAAATCCCTCTGCCCGA   480
AACTTGCCCGAACTTACTCCCTAAGACCGATGCCCACTTG   520
AGTCACATGAGTTGATTAGTCGATTCCACCCTAGCTCCCG   560
CGAACTCAGCAGTGCCCGTTGCGACTCCGCCAAATCACTA   600
ATCCTTAATTAAAAGAACTAATAAGTTGATATCATCACAT   640
TTGTGGTAACTCATGCATGCACATAGGTTTCCTAGATACC   680
ATTGAAGGAAGTTGCCATGTGTTTGAATCAAAGATTTGCC   720
CACCACCATTGATACTGAAATTGAAGAACCTAGCAGCCAG   760
CAACGGCTCCTTTTCATTTGTCTTTCAACAGAGCAAGTAA   800
CAACAACCGTTGCCTAAACTGAAACCCAATAAAGAGCAAA   840
AAAAAAGGGGTTGGGTGGTGTAGGCTAGTTTGTCTGAAAT   880
CAGTGTACATTTTGCATTTCCATTTACTCTTCTCCATCCA   920
CTTGGCATCCTGCATTACTTCTTCTTCGTTAGTTCTCACC   960
AACCTACATACTCTTCGGTTATAAATACTGTGAGGCTGAA  1000
ACCAAAGGCCACTCAGTCTATTCATTATTATTCAAAAATA  1040
TATATTGGGTTTGTTTGGTGCAGATTACAGTGACTTCAAA  1080
ACTGTGGCTCTGCACGACCAAACTATC              1107
(SEQ ID NO:9)
```

Figure 21

> Solin *LuFad3* promoter sequence

```
ACTACCTGCAAACCAAAACAGATTCATGGCCAAGCTTATT    40
CCCACAAAAGGGTCCAAACAAAAGGAAAATGGTCTGATTG    80
TCTGCTAAAGTTTATTGATCAGTACGTGGGTGGATGTTTT   120
GTTCACCTTTACAGTGCCATTCTTTACCACAGTTGTTACC   160
AGCATCACTCATCATCATCAGCATCATTAATCCTTAGTTT   200
TCTATGCACTCACTTTCATTAGTGTTCACTTTGCAATTCA   240
ATAATCCATCTATTATTCGATTGCAAAGCAAGAGAGTTGT   280
AAGAGTTTCGACTAAGTTCAAATGGAGCCCAAAGTTTGAT   320
CATCAGTTTGTGAAAACAAAGTCAAGCTCGTCCATATCTC   360
TGCCTTGTTCCCAACCCACTACATAGCATCTGGAAGACCT   400
CGTACTTCACATTCTCGGACCGAAGGACAACCAATACCCC   440
CCTTGTGATCCTAAACACATGCACAAATCCCTCTGCCCGA   480
AACTTGCCCGAACTTACTCCCTAAGACCGATGCCCACTTG   520
AGTCACATGAGTTGATTAGTCGATTTCACCCTAGCTCCCG   560
CGAACTCAGCAGTGCCCGTTGCGACTCCGCCAAATCACTA   600
ATCCTTAATTAAAAGAACTAATAAGTTGATATCATCACAT   640
TTGTGGTAACTCATGCATGCACATAGGTTTCCTAGATACC   680
ATTGAAGGAAGTTGCCATGTGTTTGAATCAAAGATTTGCC   720
CACCACCATTGATACTGAAATTGAAGAACCTAGCAGCCAG   760
CAACGGCTCCTTTTCATTTGTCTTTCAACAGAGCAAGTAA   800
CAACAACCGTTGCCTAAACTGAAACCCAATAAAGAGCAAA   840
AAAAAAGGGGTTGGGTGGTGTAGGCTAGTTTGTCTGAAAT   880
CAGTGTACATTTTGCATTTCCATTTACTCTTCTCCATCCA   920
CTTGGCATCCTGCATTACTTCTTCTTCGTTAGTTCTCACC   960
AACCTACATACTCTTCGGTTATAAATACTGTGAGGCTGAA  1000
ACCAAAGGCCACTCAGTCTATTCATTATTATTCAAAAATA  1040
TATATTGGGTTTGTTTGGTGCAGATTACAGTGACTTCAAA  1080
ACTGTGGCTCTGCACGACCAAACTATG  1107
(SEQ ID NO:10)
```

Figure 22

> *Normandy LuFad3* genomic sequence

```
ACTACCTGCAAACCAAAACAGATTCATGGCCAAGCTTATT    40
CCCACAAAAGGGTCCAAACAAAAGGAAAATGGTCTGATTG    80
TCTGCTAAAGTTTATTGATCAGTACGTGGGTGGATGTTTT   120
GTTCACCTTTACAGTGCCATTCTTTACCACAGTTGTTACC   160
AGCATCACTCATCATCATCAGCATCATTAATCCTTAGTTT   200
TCTATGCACTCACTTTCATTAGTGTTCACTTTGCAATTCA   240
ATAATCCATCTATTATTCGATTGCAAAGCAAGAGAGTTGT   280
AAGAGTTTCGACTAAGTTCAAATGGAGCCCAAAGTTTGAT   320
CATCAGTTTGTGAAAACAAAGTCAAGCTCGTCCATATCTC   360
TGCCTTGTTCCCAACCCACTACATAGCATCTGGAAGACCT   400
CGTACTTCACATTCTCGGACCGAAGGACAACCAATACCCC   440
CCTTGTGATCCTAAACACATGCACAAATCCCTCTGCCCGA   480
AACTTGCCCGAACTTACTCCCTAAGACCGATGCCCACTTG   520
AGTCACATGAGTTGATTAGTCGATTCCACCCTAGCTCCCG   560
CGAACTCAGCAGTGCCCGTTGCGACTCCGCCAAATCACTA   600
ATCCTTAATTAAAAGAACTAATAAGTTGATATCATCACAT   640
TTGTGGTAACTCATGCATGCACATAGGTTTCCTAGATACC   680
ATTGAAGGAAGTTGCCATGTGTTTGAATCAAAGATTTGCC   720
CACCACCATTGATACTGAAATTGAAGAACCTAGCAGCCAG   760
CAACGGCTCCTTTTCATTTGTCTTTCAACAGAGCAAGTAA   800
CAACAACCGTTGCCTAAACTGAAACCCAATAAAGAGCAAA   840
AAAAAAGGGGTTGGGTGGTGTAGGCTAGTTTGTCTGAAAT   880
CAGTGTACATTTTGCATTTCCATTTACTCTTCTCCATCCA   920
CTTGGCATCCTGCATTACTTCTTCTTCGTTAGTTCTCACC   960
AACCTACATACTCTTCGGTTATAAATACTGTGAGGCTGAA  1000
ACCAAAGGCCACTCAGTCTATTCATTATTATTCAAAAATA  1040
TATATTGGGTTTGTTTGGTGCAGATTACAGTGACTTCAAA  1080
ACTGTGGCTCTGCACGACCAAACTATGAGCCCTCCAAACT  1120
CAATGAGTCCCGCCACCAACGGCAGCACCAATGGTGTGGC  1160
TATCAATGGGGCGAAGAAGCTACTCGATTTCGACCCGAGT  1200
GCTGCTCCCCCTTTCAAGATTGCAGACATCCGTGCTGCAA  1240
TCCCGCCGCATTGTTGGGTGAAGAACCCCTGGAGGTCACT  1280
CAGCTACGTCCTGAGAGACCTCCTGGTCATCCTCAGCTTC  1320
GCCGTTGCGGCGACAAAGCTGGACAGCTGGACTGTCTGGC  1360
CTCTCTACTGGATTGCTCAAGGAACCATGTTCTGGGCAGT  1400
CTTTGTTCTTGGACATGATTGGTAATTTCACATGATCTTT  1440
CTGGTAATGTGGGTTTTCTTTTCTTATTGAAAAGATTAA  1480
AACTTTTTATCTGGGCTGTTGCATGCAGTGGCCATGGGAG  1520
CTTCTCAGACAGTTGGTTGTTAACAACGTGATGGGACAT  1560
ATACTCCATTCCTCAATCCTCGTACCTTACCATGGATGGT  1600
ATTGTAACTATTGTTCGATATTCGATTATGATTACTGTTC  1640
TTTCAGATGAAGAATCTGTACCCTAATTGTTTTTTGTTAC  1680
CAGGAGAATTAGCCACAAGACCCATCACCAGAATCACGGC  1720
AATGTGGAGAAAGATGAATCCTGGGTTCCAGTAAGTTGAC  1760
ATGCAGTTTGCTCTAAAATGCAGAGTCCTCTGTTTTTTGT  1800
GTGTTCTTGTGCTTTAATGGCGAATGATAATGAAATTGAA  1840
ATTTGTAATAGCTGCCGGAGAAGGTGTACAAGAGCTTGGA  1880
```

Figure 23

```
TACCGGCACCAAGTTCATGAGGTTCACCATCCCTCTCCCA 1920
ATGTTTGCGTATCCTATCTACTTGGTAAGTAAACAGACTG 1960
ACTCCAAAGTAGGAACTAATGACAATTTTGGACCCGACCT 2000
GGTTTGGTTGACTCGGGTCGATATGTTTCGGGTGGGTAAT 2040
TACCCGATCTGGCGATGGGTGTGCGGCGGACATTGTCTTG 2080
CTCGTGGTCCACCCCGCTCCCAACCCGCCCCATTCTTGAC 2120
GAAAAGATTTCGGAATATGTATCAACAGAAAATCTAGT 2160
TTTTATGTTACTAGTTTTCTGTATTTCCATGTTTTTTCCT 2200
CAATTCTAGCCGGAATTTGAATTCAAACTGAAATCGGGTA 2240
ATTCCGTCCATAACAAAACGGAATTGGGCCACCGGTAATT 2280
AGTTGAAACTAACCTCAATTTTGGCGGAATTGGACCGGCC 2320
ATTTTTTACGTTTGCAAACGGAAAACGTTTTTTTTTTGTA 2360
AAGCGCAAAATGAAAAACGTATCTAAGTGGAATTATTGGA 2400
CCCATCTAGAATGGGTCCATTCCACCCCCAATTTCGGGCT 2440
CCAATTCATGCCCGGAAAACACTACTGTCATGCATTTTAA 2480
TCTTGTATGGTTTTACCCCAATGGATGCAGATGGATCCGG 2520
ACGATTTTTAAAATATTATCGGGTTAAATTTAAAAATATC 2560
TTAAAACTATAAGAAAAAATAACCAATTTTAAAGAATAA 2600
AAGAACTGGACACATATGACGGGTGTCGTGGATGGATGTA 2640
CTTGTCCCGCTCTATTAAAGGCTGATAATATACAGGTCAA 2680
CGGTGAATGAAGGTTAGATGCGCTATTGGATTTGAATCCG 2720
ATATGAAATGATAATTTTGGACACGATCTGTTTTGGGTGG 2760
GTAATATTTGATCTAGGGATGGCTCGTGCTCCAAACCGCA 2800
CCAAAACCGCCTAATTCTCGACCAAAAGATTTTATGAAT 2840
ACATATCAACAGAAAATCTAGTTTTCATGTTACTAGTTT 2880
TATGTACAACAATATTAGGTGTCGTTTTCCCAGCCTTTTT 2920
CTTCAATTCCGGCCGGAATTCGCATTCAAACCGGAATTGG 2960
ATGGAATCGGTATACCTCGTCACGGATGCATTGTCAATTC 3000
CTAGTTAGTTTCATGGTTTTGAAACCAATCAATCTATTCT 3040
ATATGGTTTTGATTAACAGTGGAGGAGAAGTCCGGGGAAG 3080
AAAGGGTCGCATTTCAACCCATACAGTGACCTGTTCGCAC 3120
CGAACGAGAGGACATCGGTCATGATTTCGACATTGTGCTG 3160
GACAGCCATGGCCTTACTCCTCTGCTACTCATCGTTCATC 3200
TACGGCTTCCTTCCGGTCTTCAAAATCTACGGCGTCCCTT 3240
ATCTAATATTCGTGGCGTGGCTCGACATGGTGACCTACCT 3280
TCACCACCACGGGTACGAGCAGAAGCTGCCGTGGTACAGA 3320
GGCAAAGAGTGGAGCTACCTACGTGGAGGGCTGACGACCG 3360
TCGATCGAGATTACGGGGTCATCAACAACATCCACCATGA 3400
CATTGGCACCCATGTTATTCACCATCTCTTCCCTCAAATG 3440
CCACACTATCACCTTGTGGAAGCGGTAAACAATTTGATTA 3480
TTAATTTACTGTTTTTGTTGTTATAATTTGAGTCGGGAGA 3520
TTTCCTTCCTAAATCCGATCCCTGGTCAATCTTGGCCCTT 3560
GAATCTTCATATAATCTAAAAATCTAGATTAATCAGGAAC 3600
AATATGATCATGTTGTTTAAACTAATTTGTTGGACCATA 3640
ACCTACCGCCAACTGATGGACCACCGTCTCTGGTTACCGG 3680
ACCCATCATTTCCGGTTACCAAGAAGTTTCTCGATCAGTT 3720
TTCCGGTTACTTTGACCTGCGTTGAGGAAAATTCTTTCAC 3760
CCACGTAAACACTGTCGTCAACTTTACGTTTCTGGAAAGT 3800
```

Figure 23 continued

```
TTTTCCGATGATTGGCCGTACAATTTTGTACSAAAGAGTT 3840
GTACGGATCATATAAATGTGTATAAGTTTCTAGAAATCCG 3880
TACTGAAATATATACATATTTGACTTTTGTATAAAGTGTA 3920
ATACTAAATACTATACTAAGTGCTGTACTCAGTATGATAC 3960
TTAGTACACATTTGTATGACTATGAAATGTCAATTTTG   4000
CCCTTATATTCTCAGCCGTTAGATCTAAGACACAGTTTTT 4040
ATACGGCTGAAATTTGTGGGGCTTTGTAGATCGGATCCA  4080
TAAGTCATTTCTTCGCTCAAGATTCGGACTCGATTATTAA 4120
CTATATTATTCATCAACTCTGACGTTTGATGTTGCAGTCG 4160
AAGCGACTCAGGCAGCGAAGCACGTGCTGGGGAAGTACTA 4200
CAGAGAACCGAAGAAATCAGGGCCTTTCCCATTCCACTTG 4240
TTTGGGTACTTGGTGAGGAGCCTGGGCGAGGATCACTACG 4280
TTAGCGATACAGGCGACGTCGTTTTCTATCAATCTGACCC 4320
ACATATTCCCAAGTTCCCTACCAGTGCCACCACCAAGTCC 4360
AAATCTAGCTGATGATATTGGCTCTGATCTGATGTATGCT 4400
GCAGGCTGTTTTATTTTGTCCTTTGTTCGTTTCTTTCTGC 4440
CAGAAACAAATTCTCTGTTTCTATGTTTCTCTGTCTCTCC 4480
CACCCCAGCTTTCTTTCTGAGTATATCGTATAAAGTTTCA 4520
AGTGATTGTAAGAGCAGAAAAGAAAGAAGAAGAAGAATA  4560
ATAAAGAGGATTGGC 4575
(SEQ ID NO: 11)
```

Figure 23 continued

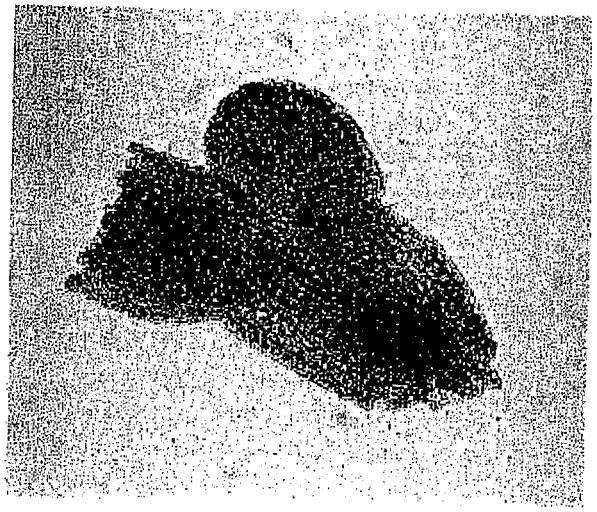
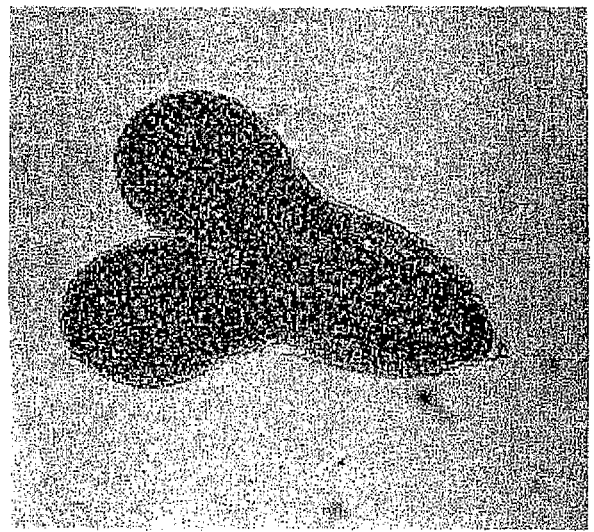
Figure 25

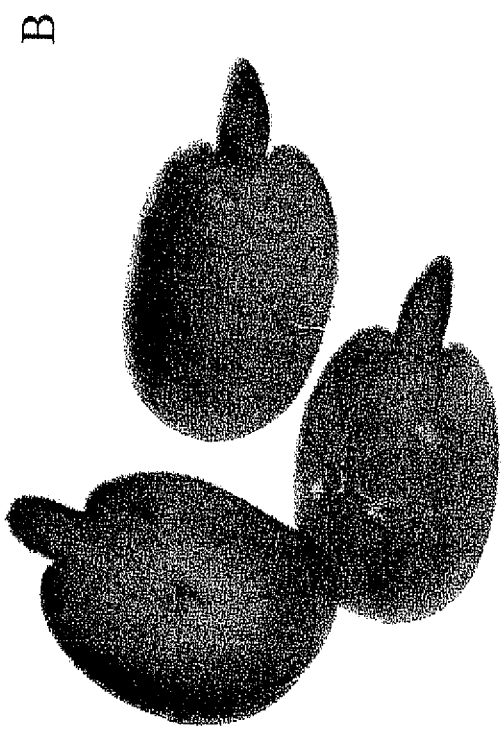
Figure 26

FLAX (*LINUM USITATISSIMUM* L.) SEED-SPECIFIC PROMOTORS

RELATED APPLICATIONS

This application is a divisional of patent application Ser. No. 11/655,545, filed Jan. 19, 2007, now U.S. Pat. No. 7,473,820, which is a divisional of patent application Ser. No. 10/165,289, filed Jun. 6, 2002, now U.S. Pat. No. 7,193,134, which claims priority to U.S. Provisional Application No. 60/295,823 entitled "Flax (*Linum usitatissimuin* L.) Speed-Specific Promoters" filed Jun. 6, 2001. The entire content of each above-mentioned application is hereby incorporated by reference in its entirety. The entire contents of Appendix A including the entire contents of all references cited therein also are expressly incorporated by reference and are intended to be part of the present application.

BACKGROUND OF THE INVENTION

The recent advances in plant molecular biology have made possible genetic engineering of most crop species. The technology has been applied to improving agronomic traits, producing pharmaceutical protein, and modifying the final storage products.

The essential parts of plant genetic engineering techniques are promoters that regulate the expression of newly introduced genes. Promoters are genomic fragments that are usually preceding the coding regions of genes and contain regulatory elements recognized by transcription factors of the plant cells. The specific interaction of regulatory elements in promoter region and transcription factors in the cells results in the switch-on and -off of gene transcription.

In general, gene expression is monitored by the comprehensive mechanism which includes multi-levels of the integrative controls, such as transcription, RNA processing, translation and protein processing. However, the majority of genes, especially tissue-specific genes, are mainly regulated at the transcriptional level. Precise control of the tissue-specific genes at transcriptional level in time and space is a prerequisite of cell division and cell differentiation. Therefore, isolation and characterization of the upstream regulatory region of a gene—the promoter are important not only in genetic engineering of plant traits, but also in understanding basic mechanism of cell division and differentiation, which are basis of plant growth and development.

As an important oilseed crop, flax is an excellent target for fixture genetic engineering in efforts to improve agronomic performance, modify fatty acid composition of the seed oil or produce recombinant proteins. Unfortunately, there has been little effort in identification of tissue-specific promoters in flax. In flax, two homologous promoters have been isolated by the PCR cloning strategy, both being the upstream regions of stearoyl-acyl carrier protein desaturase (SAD) genes. The expression pattern of the SAD2 promoter in flax can be regarded as constitutive as it is expressed in most of the tissues. SAD1, on the other hand, is expressed only in roots and seeds, but at the significantly lower level.

SUMMARY OF THE INVENTION

Identification of effective tissue-specific promoters is essential to the overall understanding of the molecular mechanism underlying the developmental process. Identifying seed-specific promoters will allow for the developmental process to be manipulated and will have an impact on the flaxseed or agricultural industry. This invention relates to identification of two types of promoters (Conlinin and LuFad3) from flax (*Linum usitatissimum*) that guide high levels of the expression exclusively at the middle stage of seed development. These promoters can be utilized to improve seed traits, modify the fatty acid composition of seed oil and amino acid composition of seed storage protein, and produce bioactive compounds in plant seeds.

The invention is described for the purpose of demonstration with methods and sequences related to Conlinin 1, Conlinin 2, and LuFad3. It is recognized, however, that within the scope of the invention, the utility of the invention will include employing the illustrative method to identify and use the genes from other plants which have a sufficient degree of nucleotide and amino acid identity, and genes with proper changes made by a person skilled in the art.

In one embodiment, the invention features an isolated nucleic acid molecule which encodes a polypeptide having an activity of catalyzing the formation of a double bond. In a further embodiment, the nucleic acid molecule features a nucleotide sequence of LuFad3 from the genus *Linum*. In another embodiment, the invention consists of a nucleotide sequence which is at least about 60% identical to the nucleotide sequence of SEQ ID NO:7, or a complement thereof. In yet another embodiment, the invention features a nucleotide sequence comprising a fragment of the nucleotide sequence of SEQ ID NO:7. In still another embodiment of the invention, the invention features a nucleotide sequence which encodes a polypeptide comprising an amino acid sequence that is at least about 70% homologous to the amino acid sequence of SEQ ID NO:8. In still another embodiment, the invention features a nucleotide sequence which encodes a fragment of a polypeptide comprising the amino acid sequence of SEQ ID NO:8, wherein the fragment comprises at least 15 contiguous amino acids of SEQ ID NO:8. In a flier embodiment, the invention describes a nucleotide sequence which encodes a naturally occurring allelic variant of a polypeptide comprising the amino acid sequence of SEQ ID NO:8, wherein the nucleic acid molecule hybridizes to a nucleic acid molecule comprising SEQ ID NO:7, or a complement thereof under stringent conditions. In yet a further embodiment, the isolated nucleic acid molecule encodes a polypeptide having an activity of catalyzing the formation of a double bond at position 15 from the carboxyl end of a fatty acyl chain.

In another aspect, the invention features an isolated nucleic acid molecule which consists of a nucleotide sequence of Conlinin 1 from the genus *Linum*. In another embodiment, the invention features a nucleotide sequence which is at least about 60% identical to the nucleotide sequence of SEQ ID NO:1, or a complement thereof. In still another embodiment, the invention includes a nucleotide sequence comprising a fragment of the nucleotide sequence of SEQ ID NO:1. In yet another embodiment, the invention includes a nucleotide sequence which encodes a polypeptide comprising an amino acid sequence that is at least about 60% homologous to the amino acid sequence of SEQ ID NO:2. In still another embodiment, the invention features a nucleotide sequence which encodes a fragment of a polypeptide comprising the amino acid sequence of SEQ ID NO:2, wherein the fragment comprises at least 15 contiguous ammo acids of SEQ ID NO:2. In a farther embodiment, the invention includes a nucleotide sequence which encodes a naturally occurring allelic variant of a polypeptide comprising the amino acid sequence of SEQ ID NO:2, wherein the nucleic acid molecule hybridizes to a nucleic acid molecule comprising SEQ ID NO:1, or a complement thereof under stringent conditions.

Another aspect of the invention includes an isolated nucleic acid molecule, which consists of a nucleotide sequence of Conlinin 2 from the genus *Linum*. In another embodiment, the invention features a nucleotide sequence which is at least about 60% identical to the nucleotide sequence of SEQ ID NO:3, or a complement thereof. In yet another embodiment, the invention features a nucleotide sequence comprising a fragment of the nucleotide sequence of SEQ ID NO:3. in still a further embodiment, the invention features a nucleotide sequence which encodes a polypeptide comprising an amino acid sequence that is at least about 55% homologous to the amino acid sequence of SEQ ID NO:4. In another embodiment, the invention features a nucleotide sequence which encodes a fragment of a polypeptide comprising the amino acid sequence of SEQ ID NO:4, wherein the fragment comprises at least 15 contiguous amino acids of SEQ ID NO:4. The invention also features, a nucleotide sequence which encodes a naturally occurring allelic variant of a polypeptide comprising the amino acid sequence of SEQ ID NO:4, wherein the nucleic acid molecule hybridizes to a nucleic acid molecule comprising SEQ ID NO:3, or a complement thereof under stringent conditions.

The invention provides a vector comprising the nucleic acid molecule of an isolated nucleic acid molecule, comprising a nucleotide sequence of Conlinin 1, Conlinin 2, and/or Lufad3 from the genus *Linum*. The invention also provides a host cell transformed with the vector containing Conlinin 1, Conlinin 2, and/or Lufad3 from *Linum*, including an expression vector. In another embodiment of the invention, a method is provided of producing a polypeptide by culturing the host cell of containing such an expression vector in an appropriate culture medium in order to produce the polypeptide. The cell of the invention can be, but is not limited to, a plant cell.

In another embodiment of the invention, a method of producing a cell capable of generating α-linoleic acid is provided by performing a method consisting of introducing into a cell the nucleic acid molecule of LuFad3, wherein the nucleic acid molecule encodes a desaturase having an activity of catalyzing the formation of a double bond at position 15 from the carboxyl end of a fatty acyl chain.

In yet another embodiment of the invention, a promoter consisting of a nucleotide sequence isolated from *Linum* which is capable of directing gene expression in developing flax seeds is provided. In one embodiment, an isolated *Linum* Conlinin 1 promoter consisting of the nucleotide sequence of SEQ ID NO: 5, or a portion thereof is provided. In yet another embodiment, an isolated *Linum* Conlinin 2 promoter comprising the nucleotide sequence of SEQ ID NO: 6, or a portion thereof is provided. In still another embodiment, a vector comprising the *Linum* Conlinin promoter Conlinin and/or Conlinin 2 operably linked to a heterologous gene of interest is provided. in still another embodiment, an isolated *Linum* LuFad 3 promoter comprising the nucleotide sequence of SEQ ID NO: 9 and/or SEQ ID NO:10, or a portion thereof is provided. The Lufad3 promoter can be isolated from flax variety cultivar CDC Normandy and/or cultivar CDC Solin. A vector comprising a *Linum* LuFad3 promoter operably linked to a heterologous gene of interest is also provided In another embodiment, the invention provides an isolated nucleic acid sequence capable of directing seed-specific expression in a plant consisting of a nucleic acid comprising the nucleotides of SEQ ID NO: 5 or SEQ ID NO: 6. or a nucleic acid sequence that is complimentary to the nucleotide sequence of SEQ ID NO: 5 or SEQ ID NO: 6, or a nucleic acid sequence that is at least about 60% homologous to the nucleotide sequence of SEQ ID NO: 5 or SEQ ID NO: 6.

The invention also provides an isolated nucleic acid sequence capable of directing seed-specific expression in a plant consisting of a nucleic acid comprising the nucleotides of SEQ ID NO: 9 or SEQ ID NO: 10, or a nucleic acid sequence that is complimentary to the nucleotide sequence of SEQ ID NO: 9 or SEQ ID NO: 10, or a nucleic acid sequence that is at least about 60% homologous to the nucleotide sequence of SEQ ID NO: 9 or SEQ ID NO: 10.

Also provided by the invention is a method for the expression of a nucleic acid sequence of interest in flax seeds consisting of preparing a nucleic acid construct comprising a seed-specific promoter operably linked to a gene of interest, wherein the gene of interest is non-native to the seed-specific promoter, introducing the construct into a flax plant cell, and growing said cell into a mature plant capable of setting seed wherein the gene of interest is expressed in the seed under the control of the seed-specific promoter.

BRIEF DESCRIPTION OF THE FIGURES

FIG. 1 depicts the nucleotide sequence of Conlinin 1 cDNA (SEQ ID NO: 1).

FIG. 2 depicts the deduced protein sequence of Conlinin 1 (SEQ ID NO: 2).

FIG. 3 depicts the nucleotide sequence of Conlinin 2 cDNA (SEQ ID NO: 3).

FIG. 4 depicts the deduced protein sequence of Conlinin 2 (SEQ ID NO: 4).

FIG. 5 depicts a comparison of the nucleotide sequences of Conlinin 1 and Conlinin 2.

FIG. 6 depicts a comparison of the amino acid sequences of Conlinin 1 and Conlinin 2 proteins.

FIG. 7 depicts a comparison of the Conlinin 1 protein with the *Arabidopsis thaliana* 2S storage protein (At2S2).

FIG. 8 depicts the promoter sequence of Conlinin 1 (SEQ ID NO: 5).

FIG. 9 depicts the promoter sequence of Conlinin 2 (SEQ ID NO:6).

FIG. 14 depicts the cDNA nucleotide sequence of LuFad3 from flax (SEQ ID NO: 7).

FIG. 15 depicts the deduced protein sequence of LuFad3 from flax (SEQ ID NO: 8).

FIG. 21 depicts the promoter sequence of LuFad3 (Normandy) (SEQ ID NO:9).

FIG. 22 depicts the promoter sequence of LuFad3 (Solin) (SEQ ID NO:10).

FIG. 23 depicts the nucleotide sequence of the LuFad3 genomic sequence from Normandy (SEQ ID NO: 11).

FIG. 25 depicts flax promoter activity in *Arabidopsis thaliana*. A shows positive GUS staining of the developing embryo from a transgenic plant B shows negative results from GUS staining of the developing embryo from a non-transformed plant FIG. 26 shows the LuFad3 promoter activity in flax. A depicts GUS expression under control of the LuFad3 promoter in the developing embryo. B shows the control embryo.

DETAILED DESCRIPTION OF THE INVENTION

Figure 10:
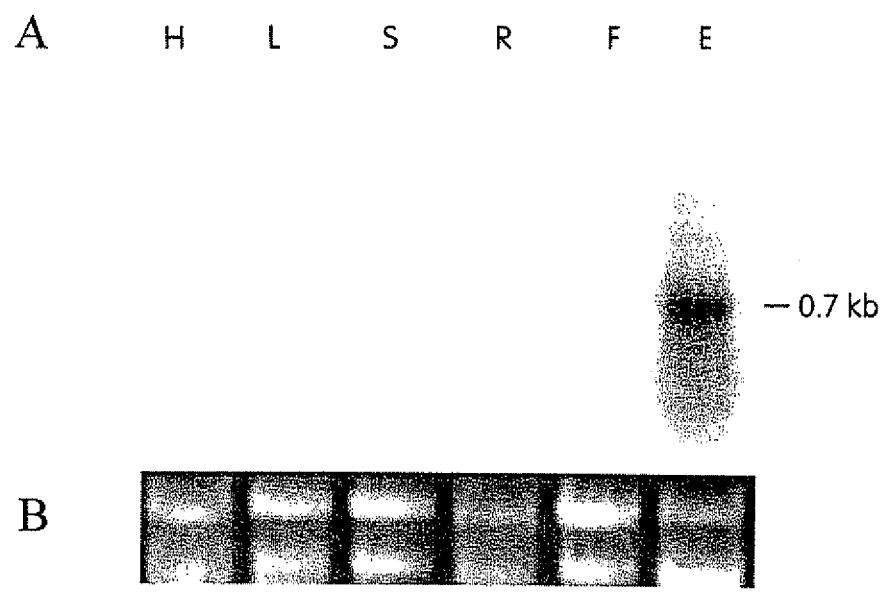
FIG. 10 depicts the spatial expression of Conlinin. A shows a northern blot hybridization with the Conlinin 1 probe. B shows an ethidium bromide gel indicating RNA loading. The total RNA was isolated from H: hypocotyls, L: leaves, S: stems, R: roots, F: flowers, and B: embryo at 20 days after flowering.

The present invention is based, at least in part, on the discovery of novel promoters from genes from flax (*Linum usitatissimum* L.) that guide high levels of expression exclusively during the middle stage of seed development. Specifically, the inventors have identified two Conlinin genes (Conlinin 1 and Conlinin 2) and their respective promoter regions. The inventors have also identified an ω-3 desaturase (formerly Δ15 desaturase) LuFad3 and its corresponding promoter sequence. The described promoters can be utilized to improve seed traits, modify the fatty acid composition of seed oil and amino acid composition of seed storage protein, and produce bioactive compounds in plant seeds. Accordingly, the present invention features methods based on using the presently identified genes to transform plants such that the proteins of the invention are expressed. The present invention also features methods based on using the described promoter sequences of LuFad3, Conlinin 1, and Conlinin 2 to direct seed-specific expression of a gene of interest.

As used herein, the term "2S storage proteins" refers to seed storage proteins which are generally classified on the basis of solubility and size (more specifically sedimentation rate, for instance as defined by Svedberg (in Stryer, L., Biochemistry, 2nd ed., W.H. Freeman, New York, page 599). The 2S seed storage proteins are water soluble albumins and thus easily separated from other proteins. Their small size also simplifies their purification. Several 2S storage proteins have been characterized at either the protein or cDNA levels (Crouch et al., 1983; Sharief and Li, 1982; Ampe et al., 1986; Altenbach et al., 1987; Ericson et al., 1986; Scofield and Crouch, 1987; Josefsson et al., 1987; and work described in the present application).

As used herein, the term "conjugated double bonds" is art recognized and includes conjugated fatty acids (CFAS) containing conjugated double bonds. For example, conjugated double bonds include two double bonds in the relative positions indicated by the formula —CH=CH—CH=CH—. Conjugated double bonds form additive compounds by saturation of the 1 and 4 carbons, so that a double bond is produced between the 2 and 3 carbons.

As used herein, the term "fatty acids" is art recognized and includes a long-chain hydrocarbon based carboxylic acid. Fatty acids are components of many lipids including glycerides. The most common naturally occurring fatty acids are monocarboxylic acids which have an even number of carbon atoms (16 or 18) and which may be saturated or unsaturated. "Unsaturated" fatty acids contain cis double bonds between the carbon atoms. "Polyunsaturated" fatty acids contain more than one double bond and the double bonds are arranged in a methylene interrupted system (—CH=CH—CH$_2$—CH=CH—). Fatty acids encompassed by the present invention include, for example, linoleic acid, linolenic acid, oleic acid, calendic acid and palmitoleic acid.

Fatty acids are described herein by a numbering system in which the number before the colon indicates the number of carbon atoms in the fatty acid, whereas the number after the colon is the number of double bonds that are present. In the case of unsaturated fatty acids, this is followed by a number in parentheses that indicates the position of the double bonds. Each number in parenthesis is the lower numbered carbon atom of the two connected by the double bond. For example, oleic acid can be described as 18:1(9) and linoleic acid can be described as 18:2(9, 12) indicating 18 carbons, one double bond at carbon 9 and 18 carbons, two double bonds at carbons 9 and 12, respectively.

As used herein, the term "conjugated fatty acids" is art recognized and includes fatty acids containing at least one set of conjugated double bonds. The process of producing conjugated fatty acids is art recognized and includes, for example, a process similar to desaturation, which can result in the introduction of one additional double bond in the existing fatty acid substrate.

As used herein, the term "linoleic acid" is art recognized and includes an 18 carbon polyunsaturated fatty acid molecule ($C_{17}H_{29}COOH$) which contains 2 double:bonds (18:2 (9,12)). The term "Conjugated linoleic acid" (CLA) is a general term for a set of positional and geometric isomers of linoleic acid that possess conjugated double bonds, in the cis or trans configuration.

As used herein, the term "desaturase" is art recognized and includes enzymes that are responsible for introducing conjugated double bonds into acyl chains. In the present invention, for example, the ω-3 desaturase (formerly Δ15 desaturase) from *Linum usitatissimum* is a desaturase that can introduce a double bond at position 15 of linoleic acid.

In one embodiment, a recombinant vector of the present invention includes nucleic acid sequences that encode at least one plant gene product operably linked to a promoter or promoter sequence. Preferred promoters of the present invention include *Linum* promoters. In one example, the promoter comprises a Conlinin 1 promoter (SEQ ID NO:5), or a portion thereof. In another example, the promoter of the invention comprises a Conlinin 2 promoter (SEQ ID NO:6), or a portion thereof. In yet another embodiment of the invention, the promoter comprises a LuFad3 promoter (SEQ ID NOs: 9 and 10), or a portion thereof.

In yet another embodiment, a recombinant vector of the present invention includes a terminator sequence or terminator sequences (e.g., transcription terminator sequences). The term "terminator sequences" includes regulatory sequences which serve to terminate transcription of mRNA. Terminator sequences (or tandem transcription terminators) can farther serve to stabilize mRNA (e.g., by adding structure to mRNA), for example, against nucleases.

In yet another embodiment, a recombinant vector of the present invention includes antibiotic resistance sequences. The term "antibiotic resistance sequences" includes sequences which promote or confer resistance to antibiotics on the host organism (e.g., *Linum*). In one embodiment, the antibiotic resistance sequences are selected from the group consisting of cat (chloramphenicol resistance), tet (tetracycline resistance) sequences, erm (erythromycin resistance) sequences, neo (neomycin resistance) sequences and spec (spectinomycin resistance) sequences. Recombinant vectors of the present invention can further include homologous recombination sequences (e.g., sequences designed to allow recombination of the gene of interest into the chromosome of the host organism). For example, amyE sequences can be used as homology targets for recombination into the host chromosome.

It will further be appreciated by one of skill in the art that the design of a vector can be tailored depending on such factors as the choice of cell to be genetically engineered, the level of expression of gene product desired and the like.

In one embodiment of the invention, a promoter region, or portion thereof, from Conlinin 1, Conlinin 2, and/or LuFad3 (SEQ ID NOs: 5, 6, 9, and/or 10) is operably linked to a non-native sequence. As used herein, the term "non-native" refers to any nucleic acid sequence including any RNA or DNA sequence, which is not normally associated with the seed-specific promoter. This includes heterologous nucleic acid sequences which are obtained from the same plant species as the promoter but are not associated with the promoter in the wild-type (non-transgenic) plant. In one embodiment, non-native genes of the invention include any gene associated with lipid biosynthesis and/or fatty acid biosynthesis.

In one embodiment of the invention, the non-native nucleic acid comprises any gene associated with lipid biosynthesis and/or fatty acid biosynthesis. Examples of genes involved in fatty acid biosynthesis include, but are not limited to, conjugases, Δ4 desaturase, Δ5 desaturase, and Δ6 desaturase. The gene of interest, including the examples set forth here, can be operatively linked to a promoter of the invention such that the gene of interest is expressed in developing seeds. In a preferred embodiment, the gene of interest is "plant derived." The term "plant-derived" or "derived-from", for example a plant, includes a gene product which is encoded by a plant gene.

The non-native nucleic acid sequence when linked to a seed-specific promoter from flax results in a chimeric or fusion product. The chimeric construct is introduced into a flax plant cell to create a transgenic flax plant cell which results in a detectably different phenotype of the flax plant cell or a flax plant grown from it when compared with a non-transgenic flax plant cell or flax plant grown from it. A contiguous nucleic acid sequence identical to the nucleic acid sequence of the chimeric construct is not present in the non-transformed flax plant cell or flax plant grown from it. In this respect, chimeric nucleic acid sequences include those sequences which contain a flax promoter linked to a nucleic acid sequence obtained from another plant species or a nucleic acid sequence from flax but normally not associated with that promoter. Chimeric nucleic acid sequences as used herein further include sequences comprising a flax promoter and a nucleic acid sequence that is normally linked to the promoter but additionally containing a non-native nucleic acid sequence. For example, if the promoter is a flax seed-specific ω-3 desaturase LuFa43 promoter, sequences "non-native" to the flax ω-3 desaturase LuFad3 promoter also include a sequence comprising a fusion between the flax ω-3 desaturase LuFad3 gene naturally associated with the ω-3 desaturase promoter, and a coding sequence of interest that is not naturally associated with the promoter. The term non-native is also meant to include a fusion gene, which additionally includes a cleavage sequence separating the nucleic acid sequence that is normally linked to the promoter sequence and the gene encoding the protein of interest.

The term "seed-specific promoter", means that a gene expressed under the ω-3 control of the promoter is predominantly expressed in plant seeds with no or no substantial expression, typically less than 5% of the overall expression level, in other plant tissues.

In one aspect of the invention, the present invention provides novel flax seed specific promoters useful for the expression of non-native genes in flax seeds and the seeds of other plant species. The promoters may be used to modify for example the protein, oil, or polysaccharide composition of the seeds.

In another aspect of the invention, the chimeric nucleic acid sequences can be incorporated in a known manner in a recombinant expression vector. Accordingly, the present invention includes a recombinant expression vector comprising a chimeric nucleic acid sequence of the present invention suitable for expression in a seed cell.

The term "suitable for expression in a seed cell" means that the recombinant expression vectors contain the chimeric nucleic acids sequence of the invention, a regulatory region, and a termination region, selected on the basis of the seed cell to be used for expression, which is operatively linked to the nucleic acid sequence encoding the polypeptide of the gene of interest. "Operatively linked" or "operably linked" are intended to mean that the chimeric nucleic acid sequence encoding the polypeptide is linked to a regulatory sequence and termination region which allows expression in the seed cell. A typical construct consists, in the 5' to 3' direction of a regulatory region complete with a promoter capable of directing expression in a plant, a polypeptide coding region, and a transcription termination region functional in plant cells. These constructs may be prepared in accordance with methodology well known to those of skill in the art of molecular biology (see for example: Sambrook et at. (1990), Molecular Cloning, 2nd ed. Cold Spring Harbor Press). The preparation of constructs may involve techniques such as restriction digestion, ligation, gel electrophoresis, DNA sequencing and PCR. A wide variety of cloning vectors is available to perform the necessary cloning steps. Especially suitable for this purpose are the cloning vectors with a replication system that is functional in *Escherichia coli* such as pBR322, the pUC series M13mp series, pACYC184, pBluescript etc. Nucleic acid sequences may be introduced into these vectors and the vectors may be used to transform *E. coli* which may be grown in an appropriate medium. Plasmids may be recovered from the cells upon harvesting and lysing the cells. Final constructs may be introduced into plant vectors compatible with integration into the plant such as the Ti and Ri plasmids.

The methods for the expression of non-native genes in flax seeds in accordance with the present invention may be practiced using any flax seed-specific promoter and are not limited to the specific flax seed specific promoter that is described herein. In preferred embodiments of the present invention, the flax seed-specific promoter confers to the non-native nucleic acid sequence at least one phenotypic characteristic which is similar or identical to a phenotypic characteristic conferred to the native nucleic acid sequence by the native promoter. The term "phenotypic characteristic" or "phenotype" as used herein refers to any measurable property or effect conferred by the flax seed-specific promoter to the nucleic acid sequence operably linked to the flax seed-specific promoter. In one embodiment, timing of expression in the plant's life cycle, of the non-native nucleic acid sequence is similar or identical to timing of expression of the native nucleic acid sequence. In another embodiment the expression level of the heterologous nucleic acid sequence is similar or identical to the expression level of the native nucleic acid sequence. Other desired expression characteristics conferred by a flax seed-specific promoter may be recognized by those skilled in the art and a flax seed-specific promoter may be selected accordingly.

Flax-seed specific promoters that may be used in accordance with the present invention include promoters associated with seed storage proteins, such as all albumins and globulins, including the vicilin and legumin-like proteins, as well as seed-specific promoters not associated with seed storage proteins, such as oleosins. Of further particular interest are promoters associated with fatty acid metabolism, such as acyl carrier protein (ACP), saturases, desaturases, and elongases.

In one feature of the invention, the flax Conlinin and Lufad3 gene promoters are capable of controlling gene expression specifically during seed development. In one embodiment of the invention, the seed-specific promoter is the promoter sequence of LuFad3 (SEQ ID NO:9 or SEQ ID NO:10), or a portion thereof. In another embodiment of the invention, the seed-specific promoter is the promoter sequence of Conlinin 1 and/or Conlinin 2 (SEQ ID NO:5 and/or SEQ ID NO:6), or a portion thereof. In another embodiment, the seed-specific promoter has the nucleotide sequence as described in FIG. 21 and/or FIG. 22. In yet another embodiment of the invention, the seed-specific promoter has the nucleotide sequence described in FIG. 8 and/or FIG. 9. In still another embodiment of the invention, a promoter sequence is used which is at least about 60%, preferably about 70%, more preferably about 80%, and even more preferably about 90% or more identical to a promoter nucleotide sequence set forth in SEQ ID NO:5, SEQ ID NO:6. SEQ ID NO:9, and/or SEQ ID NO:10. In still another embodiment a promoter sequence of the invention is used which hybridizes under stringent conditions to any of SEQ ID NO:5, SEQ ID NO:6. SEQ ID NO:9, and/or SEQ ID NO:10.

The gene of interest to be operatively linked to the promoter may be any nucleic acid sequence of interest including any RNA or DNA sequence encoding a peptide or protein of interest, for example, an enzyme, or a sequence complementary to a genomic sequence, where the genomic sequence may be at least one of an open reading frame, an intron, a non-coding leader sequence, or any sequence where the complementary sequence will inhibit transcription, messenger RNA processing, for example splicing or translation. The nucleic acid sequence of the gene of interest may be synthetic, naturally derived or a combination thereof. As well, the nucleic acid sequence of interest could be a fragment of the natural sequence, for example just include the catalytic domain or a structure of particular importance. The gene of interest might also be a recombinant protein. Depending upon the nature of the nucleic acid sequence of interest it may be desirable to synthesize the sequence with plant preferred codons. The plant preferred sly codons may be determined from the codons of highest frequency in the proteins expressed in the largest amount in particular plant species of interest, and is known to one skilled in the art.

In one embodiment of the invention, the described seed-specific promoter can be operatively linked the gene of interest, particularly a desaturase and/or a conjugase, such that the gene of interest, or product thereof, is overexpressed and purified and/or extracted from the seed. One aspect of the present invention features culturing a cell containing the seed-specific promoter linked to the gene of interest. In this aspect the gene of interest is involved in this biosynthesis, and overexpression of this gene leads to increased production in fatty acid biosynthesis. Accordingly, in one aspect the present invention features a method of producing a conjugase or a desaturase which includes culturing a cell (e.g., a *Saccharomyces cerevisae* cell) under conditions such that a conjugase or desaturase is produced. The term "overexpressing cell" includes a cell which has been manipulated such that the conjugase or desaturase is overexpressed. The term "overexpressed" or "overexpression" includes expression of a gene product at a level greater than that expressed prior to manipulation of the cell or in a comparable cell which has not been manipulated. In one embodiment the cell can be genetically manipulated (e.g., genetically engineered) to overexpress a level of gene product greater than that expressed prior to manipulation of the cell or in a comparable cell which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins). In another embodiment the cell can be physically or environmentally manipulated to overexpress a level of gene product greater than that expressed prior to manipulation of the cell or in a comparable cell which has not been manipulated. For example, a cell can be treated with or cultured in the presence of an agent known or suspected to increase transcription of a particular gene and/or translation of a particular gene product such that transcription and/or translation are enhanced or increased.

The term "culturing" includes maintaining and/or growing a living cell of the present invention (e.g., maintaining and/or growing a culture or strain) such that it can perform its intended function. In one embodiment, a cell of the invention is cultured in liquid media. In another embodiment, a cell of the invention is cultured in solid media or semi-solid media. In a preferred embodiment, a cell of the invention is cultured in media (e.g., a sterile, liquid media) comprising nutrients essential or beneficial to the maintenance and/or growth of the cell (e.g., carbon sources or carbon substrate, for example carbohydrate, hydrocarbons, oils, fats, fatty acids, organic acids, and alcohol's; nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts (e.g., magnesium sulfate), cobalt salts and/or manganese salts; as well as growth factors such as amino acids, vitamins, growth promoters, and the like).

Preferably, cells of the present invention are cultured under controlled pH. The term "controlled pH" includes any pH which results in production of the desired product (e.g., a conjugase). In one embodiment cells are cultured at a pH of about 7. In another embodiment, cells are cultured at a pH of between 6.0 and 8.5. The desired pH may be maintained by any number of methods known to those skilled in the art.

Also preferably, cells of the present invention are cultured under controlled aeration. The term "controlled aeration" includes sufficient aeration (e.g., oxygen) to result in production of the desired product (e.g., a fatty acid conjugase). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the fermentor or by various pumping equipment. Aeration may be further controlled by the passage of sterile air through the medium (e.g., through the fermentation mixture). Also preferably, cells of the present invention are cultured without excess foaming (e.g., via addition of antifoaming agents).

Moreover, cells of the present invention can be cultured under controlled temperatures. The term "controlled temperature" include any temperature which results Ad in production of the desired product. In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C.

Cells can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment the cells are cultured in shake flasks. In a more preferred embodiment, the cells are cultured in a fermentor (e.g., a fermentation process). Fermentation processes of the present invention include, but are not limited to, batch, fed-batch and continuous processes or methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or cell death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to an open system in which a defined fermentation media is added continuously to a fermentor and an equal amount of used or "conditioned" media is simultaneously removed, preferably for recovery of the desired product (e.g., conjugated fatty acid). A variety of such processes have been developed and are well-known in the art.

The phrase "culturing under conditions such that conjugated fatty acid is produced" includes maintaining and/or growing cells under conditions (e.g., temperature, pressure, pH, duration, etc.) appropriate or sufficient for obtaining production of a particular conjugated fatty acid or for obtaining desired yields of the particular conjugated fatty acid being produced. For example, culturing is continued for a time sufficient to produce the desired amount of conjugated fatty acid. Preferably, culturing is continued for a time sufficient to substantially reach maximal production of conjugated fatty acid. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, or greater tan 120 hours.

In one embodiment of the invention, the gene of interest, which preferably is involved in fatty acid biosynthesis including desaturases and conjugases, is operatively-linked to a seed-specific promoter of the invention and is overexpressed in a cell such that fatty acid and/or lipid production is increased in a cultured cell. In producing conjugated fatty acids, it may further be desirable to culture cells of the present invention in the presence of supplemental fatty acid biosynthetic substrates. The term "supplemental fatty acid biosynthetic substrate" includes an agent or compound which, when brought into contact with a cell or included in the culture medium of a cell, serves to enhance or increase conjugated fatty acid biosynthesis. Supplemental fatty acid biosynthetic substrates of the present invention can be added in the form of a concentrated solution or suspension (e.g., in a suitable solvent such as water or buffer) or in the form of a solid (e.g., in the form of a powder). Moreover, supplemental fatty acid biosynthetic substrates of the present invention can be added as a single aliquot, continuously or intermittently over a given period of time. In another embodiment, the invention includes the gene of interest, which preferably is involved in fatty acid biosynthesis (e.g. desaturases and conjugases), is operatively-linked to a seed-specific promoter of the invention and is expressed in a transgenic plant.

The methodology of the present invention can further include a step of recovering the conjugated fatty acid which is produced through use of the described invention comprising a seed-specific promoter operatively linked to a gene of interest which is involved in lipid biosynthesis. The term "recovering" the conjugated fatty acid includes extracting, harvesting, isolating or purifying the conjugated fatty acid from culture media. Recovering the conjugated fatty acid can be performed according to any conventional isolation or purification methodology known in the art including, but not limited to, treatment with a conventional resin (e.g., anion or cation exchange resin, non-ionic adsorption resin, etc.), treatment with a conventional adsorbant (e.g., activated charcoal, silicic acid, silica gel, cellulose, alumina, etc.), alteration or pH, solvent extraction (e.g., with a conventional solvent such as alcohol and the like), dialysis, filtration, concentration, crystallization, recrystallization, pH adjustment, lyophilization and the like. For example, a conjugated fatty acid (e.g., CLA) can be recovered from culture media by first removing the cells from the culture. Media is then passed through or over a cation exchange resin to remove cations and then through or over an anion exchange resin to remove inorganic anions and organic acids having stronger acidities than the conjugated fatty acid of interest.

Preferably, a conjugated fatty acid is "extracted", "isolated" or "purified" such that the resulting preparation is substantially free of other media components. The language "substantially free of other media components" includes preparations of conjugated fatty acid in which the compound is separated from media components of the culture from which it is produced. In one embodiment, the preparation has greater tan about 80% (by dry weight) of conjugated fatty acid (e.g., less than about 20% of other media components), more preferably greater than about 90% of conjugated fatty acid (e.g., less than about 10% of other media components), still more preferably greater than about 95% of conjugated fatty acid (e.g., less than about 5% of other media components), and most preferably greater than about 98-99% conjugated fatty acid (erg, less than about 1-2% other media components). When the conjugated fatty acid is derivatized to a salt (e.g. a calendic acid salt), the conjugated fatty acid is preferably further free of chemical contaminants associated with the formation of the salt. When the conjugated fatty acid is derivatized to an alcohol, the conjugated fatty acid is preferably further free of chemical contaminants associated with the formation of the alcohol.

Isolated nucleotides of the present invention, preferably Conlinin 1, Conlinin 2, and/or LuFad3 promoter sequences, have a nucleotide sequence sufficiently identical to SEQ ID NO: 5, SEQ ID NO: 6, SEQ ID NO:9, and SEQ ID NO:10, respectively. Isolated polypeptides of the present invention, preferably Conlinin 1, Conlinin 2, and/or LuFad3 polypeptides, have an amino acid sequence sufficiently identical to the amino acid sequence of SEQ ID NO:2, SEQ ID NO:4, or SEQ ID NO:8, respectively. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 95%, 96%, 97%, 98%, 99% or more homology or identity across the amino acid sequences of the domains and contain at least one and preferably two structural domains or motifs, are defined herein as sufficiently identical. Furthermore, amino acid or nucleotide sequences which share at least 50%, 55%, 60%, 65%, 70%, 75%, 80%, 85%, 85%, 90%, 95%, 96%, 97%, 98%, 99% or more homology or identity and share a common functional activity are defined herein as sufficiently identical.

In a preferred embodiment, Conlinin 1, Conlinin 2, or LuFad3 polypeptide has an amino acid sequence at least about 50%, 55%, 60%, 65%, 70%, 75%, 80%, 85%, 85%, 90%, 95%, 96%, 97%, 98%, 99% or more homologous or identical to the amino acid sequence of SEQ ID NO:2, SEQ ID NO:4, or SEQ ID NO:8. In yet another preferred embodiment, a Conlinin 1, Conlinin 2, or LuFad3 polypeptide is encoded by a nucleic acid molecule having a nucleotide sequence which hybridizes under stringent hybridization conditions to a complement of a nucleic acid molecule comprising the nucleotide sequence of SEQ ID NO:1, SEQ ID NO:3, or SEQ ID NO:7.

Ranges intermediate to the above-recited values, e.g., isolated proteins comprising an amino acid sequence which is about 20-60%, 60-70%, 70-80% or 80-90% identical to the amino acid sequence set forth in SEQ ID NO:2, SEQ ID NO:4, or SEQ ID NO:8 are also intended to be encompassed by the present invention. In another example, isolated promoter nucleotide sequences comprising a nucleotide sequence which is about 20-60%, 60-70%, 70-80% or 80-90% identical to the nucleotide sequence set forth in SEQ ID NO: 5, SEQ ID NO: 6, SEQ ID NO:9, or SEQ ID NO:10 are also intended to be encompassed by the present invention Values and ranges included and/or intermediate within the ranges set forth herein are also intended to be within the scope of the present invention. For example, isolated proteins comprising an amino acid sequence which is about 91%, 92%, 93%, 94%, 95%, 96%, 97%, 98%, and 99% identical to the amino acid sequence set forth in SEQ ID NO:2, SEQ ID NO:4, or SEQ ID NO:8 are intended to be included within the range of about 90% identical to the amino acid sequence set forth in SEQ ID NO:2 or SEQ ID NO:4. Furthermore, isolated promoter sequences comprising a nucleotide sequence which is about 91%, 92%, 93%, 94%, 95%, 96%, 97%, 98%, and 99% identical to the nucleotide sequence set forth in SEQ ID NO: 5, SEQ ID NO: 6, SEQ ID NO:9, or SEQ ID NO:10 are intended to be included within the range of about 90% identical to the nucleotide sequence set forth in SEQ ID NO: 5, SEQ ID NO: 6, SEQ ID NO:9, or SEQ ID NO:10.

As used interchangeably herein a "Conlinin 1 activity," "Conlinin 2 activity," "LuFad3 activity," "biological activity of Conlinin 1," "biological activity of Conlinin 2," "biological activity of LuFad3," "functional activity of Conlinin 1," or "functional activity of Conlinin 2," "functional activity of LuFad3," refers to an activity exerted by a Conlinin 1, Conlinin 2, and/or LuFad3 protein, polypeptide or nucleic acid molecule on a Conlinin 1, Conlinin 2, and/or LuFad3 responsive cell or tissue, or on a Conlinin 1, Conlinin 2, and/or LuFad3 protein substrate, as determined in vivo, or in vitro, according to standard techniques. In one embodiment, a Conlinin 1, Conlinin 2, and/or LuFad3 activity is a direct activity, such as an association with a Conlinin 1, Conlinin 2, and/or LuFad3-target molecule. As used herein, a "target molecule" or "binding partner" is a molecule with which a Conlinin 1, Conlinin 2, and/or LuFad3 protein binds or interacts in nature, such that Conlinin 1, Conlinin 2, and/or LuFad3 mediated function is achieved. In an exemplary embodiment, a Lufad3 target molecule is a fatty acyl chain. For example, the LuFad3 protein of the present invention can act as a desaturase and introduce a double bond at position 15 numbered from the carboxyl end of an acyl chain. Conlinin 1 and Conlinin 2 proteins act as storage proteins during seed development.

The nucleotide sequences of the isolated flax Conlinin 1 and Conlinin 2 promoters regions are shown in FIG. 8 (SEQ ID NO:5) and FIG. 9 (SEQ ID NO:6), respectively. The promoter sequence for Conlinin 1 is approximately 1,118 nucleotides in length. The promoter sequence for Conlinin 2 is approximately 1,014 nucleotides in length. The nucleotide sequences of the isolated flax LUFad3 promoter from types Normandy and Solin are shown in FIG. 21 (SEQ ID NO:9) and FIG. 22 (SEQ ID NO:10). The Normandy LuFad3 promoter is approximately 1,104 nucleotides in length, and the Solin LuFad3 promoter sequence is approximately 1,104 nucleotides in length. The Conlinin and LuFad3 promoters are each capable of controlling gene expression during seed development in flax.

The nucleotide sequence of the isolated flax Conlinin 1 and/or Conlinin 2 cDNA and the predicted amino acid sequence of the flax Conlinin 1 and/or Conlinin 2 polypeptides are shown in FIGS. 1-4 and in SEQ ID NOs:1, 2, 3, 4. The nucleotide sequence of the isolated flax LuFad3 cDNA and the predicted amino acid sequence of the flax LuFad3 polypeptide is shown in FIGS. 14 and 15 and in SEQ ID NOs: 7 and 8.

The flax Conlinin 1 cDNA sequence, which is approximately 673 nucleotides in length, encodes a polypeptide which is approximately 168 amino acid residues in length. The flax Conlinin 2 cDNA sequence, which is approximately 676 nucleotides in length, encodes a polypeptide which is approximately 169 amino acid residues in length. The flax LuFad3 genomic sequence is shown in FIG. 23 and SEQ ID NO:11, and is approximately 4,575 nucleotides. The flax LuFad 3 cDNA sequence is approximately 1,475 nucleotides, and encodes a polypeptide which is approximately 392 amino acids.

Various aspects of the invention are described in further detail in the following subsections:

I. Isolated Nucleic Acid Molecules

One aspect of the invention pertains to isolated nucleic acid molecules that encode Conlinin 1, Conlinin 2, and/or LuFad3 polypeptides or biologically active portions thereof as well as nucleic acid fragments sufficient for use as hybridization probes to identify Conlinin 1, Conlinin 2, and/or LuFad3-encoding nucleic acid molecules (e.g., Conlinin 1, Conlinin 2, and/or LuFad3 mRNA) and fragments for use as PCR primers for the amplification or mutation of Conlinin 1, Conlinin 2, and/or LuFad3 nucleic acid molecules. In another embodiment of the invention, isolated nucleic acids include promoter regions of the Conlinin and/or LuFad3 genes (e.g. SEQ ID NO: 5, SEQ ID NO:6, SEQ ID NO: 9, and/or SEQ ID NO:10). In yet another embodiment, the invention features any Conlinin promoter which is at least 418 nucleotides in length. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Conlinin 1, Conlinin 2, and/or LuFad3 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, or SEQ ID NO:7, or a portion thereof can be isolated using standard molecular biology techniques and the sequence information provided herein. Using all or a portion of the nucleic acid sequence of SEQ ID NO:1, SEQ ID NO:3, or SEQ ID NO:7, as a hybridization probe, Conlinin 1, Conlinin 2, and/or LuFad3 nucleic acid molecules can be isolated using standard hybridization and cloning techniques (e.g., as described in Sambrook, J., Fritsh, E. F., and Maniatis, T. *Molecular Cloning: A Laboratory Manual* 2nd, ed, Cold Spring Harbor Laboratory, Cold Spring Harbor Laboratory Press, Cold Spring Harbor, N.Y., 1989). In another embodiment of the invention, promoter regions to Conlinin 1, Conlinin 2, and/or LuFad3, including SEQ ID NO: 5, SEQ ID NO:6, SEQ ID NO: 9, and/or SEQ ID NO:10, or portions thereof, can be isolated using standard molecular biology techniques and the methods described above.

Moreover, a nucleic acid molecule encompassing all or a portion of SEQ ID NO:1, SEQ ID NO:3, or SEQ ID NO:7 can be isolated by the polymerase chain reaction (PCR) using synthetic oligonucleotide primers designed based upon the sequence of SEQ ID NO:1, SEQ ID NO:3, or SEQ ID NO:7. Similar methods can be used to isolate all or a portion of promoter sequences comprising SEQ ID NO: 5, SEQ ID NO:6, SEQ ID NO: 9, and/or SEQ ID NO:10.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Conlinin 1, Conlinin 2, and/or LuFad3 nucleotide sequences, including the corresponding promoter regions, can be prepared by standard synthetic techniques, e.g., using an automated DNA synthesizer.

In one embodiment, an isolated nucleic acid molecule of the invention comprises the nucleotide sequence shown in SEQ ID NO:1. The sequence of SEQ ID NO:1 corresponds to the flax Conlinin 1 cDNA. This cDNA comprises sequences encoding the flax Conlinin 1 polypeptide, as well as 5' untranslated sequences, and 3' untranslated sequences. In another embodiment, the nucleic acid molecule consists of the nucleotide sequence set forth as SEQ ID NO:1.

In another embodiment, an isolated nucleic acid molecule of the invention comprises the nucleotide sequence shown in SEQ ID NO:3. The sequence of SEQ ID NO:3 corresponds to the flax Conlinin 2 cDNA. This cDNA comprises sequences encoding the flax Conlinin 2 polypeptide, as well as 5' untranslated sequences, and 3' untranslated sequences. In another embodiment, the nucleic acid molecule consists of the nucleotide sequence set forth as SEQ ID NO:3.

In yet another embodiment, an isolated nucleic acid molecule of the invention comprises the nucleotide sequence shown in SEQ ID NO:7. The sequence of SEQ ID NO:7 corresponds to the flax LuFad3 cDNA. This cDNA comprises sequences encoding the flax LuFad3 polypeptide, as well as 5' untranslated sequences, and 3' untranslated sequences. In another embodiment, the nucleic acid molecule consists of the nucleotide sequence set forth as SEQ ID NO:7.

In still another embodiment, an isolated nucleic acid molecule of the invention comprises the nucleotide sequence shown in SEQ ID NO:5. The sequence of SEQ ID NO:5 corresponds to the flax Conlinin 1 promoter. This promoter comprises approximately 1,118 nucleotide bases, and includes a symmetrical arrangement of RY elements with a G-box in the center. The Conlinin 1 promoter is active in the developing seed, and is capable of controlling gene expression during seed development. In another embodiment, the nucleic acid molecule consists of the nucleotide sequence set forth as SEQ ID NO:5.

In yet another embodiment, an isolated nucleic acid molecule of the invention comprises the nucleotide sequence shown in SEQ ID NO:6. The sequence of SEQ ID NO:6 corresponds to the flax Conlinin 2 promoter. This promoter comprises approximately 1,014 nucleotide bases, and includes a symmetrical arrangement of RY elements with a G-box in the center. The Conlinin 2 promoter is capable of controlling gene expression in a seed-specific manner. In another embodiment, the nucleic acid molecule consists of the nucleotide sequence set forth as SEQ ID NO:6.

In a further embodiment of the invention, an isolated nucleic acid molecule of the invention comprises the nucleotide sequence shown in SEQ ID NO:9. The sequence of SEQ ID NO:9 corresponds to the flax Lufad3 promoter from the Normandy variety of flax. This promoter comprises approximately 1,104 nucleotide bases. The LuFad3 (Normandy) is capable of seed-specific gone expression, and is therefore capable of directing seed-specific gene expression. In another embodiment, the nucleic acid molecule consists of the nucleotide sequence set forth as SEQ ID NO:9.

In yet a further embodiment of the invention, an isolated nucleic acid molecule of the invention comprises the nucleotide sequence shown in SEQ ID NO:10. The sequence of SEQ ID NO:10 corresponds to the flax Lufad3 promoter from the Solin variety of flax. This promoter comprises approximately 1,104 nucleotide bases. The LuFad3 promoter (Solin) is also capable of directing seed-specific gene expression. In another embodiment, the nucleic acid molecule consists of the nucleotide sequence set forth as SEQ ID NO:10.

In still another embodiment, an isolated nucleic acid molecule of the invention comprises a nucleic acid molecule which is a complement of the nucleotide sequence shown in SEQ ID NO:1, SEQ ID NO:3, and/or SEQ ID NO:7, or alternatively SEQ ID NO: 5, SEQ ID NO:6, SEQ ID NO: 9, and/or SEQ ID NO:10, or a portion of any of these nucleotide sequences. A nucleic acid molecule which is complementary to the nucleotide sequence shown in SEQ ID NO:1, SEQ ID NO:3, or SEQ ID NO:7, is one which is sufficiently complementary to the nucleotide sequence shown in SEQ ID NO:1, SEQ ID NO:3, or SEQ ID NO:7, such that it can hybridize to the nucleotide sequence shown in SEQ ID NO:1, SEQ ID NO:3, or SEQ ID NO:7, thereby forming a stable duplex. Likewise, a nucleic acid molecule which is complementary to the nucleotide sequence shown in SEQ ID NO: 5, SEQ ID NO:6, SEQ ID NO: 9, and/or SEQ ID NO:10, is one which is sufficiently complementary to the nucleotide sequence shown in SEQ ID NO: 5, SEQ ID NO:6, SEQ ID NO: 9, and/or SEQ ID NO:10, such that it can hybridize to the nucleotide sequence shown in SEQ ID NO: 5, SEQ ID NO:6, SEQ ID NO: 9, and/or SEQ ID NO:10, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the nucleotide sequence shown in SEQ ID NO:1, SEQ ID NO:3, or SEQ ID NO:7, or alternatively SEQ ID NO: 5, SEQ ID NO:6, SEQ ID NO: 9, and/or SEQ ID NO:10 (e.g., to the entire length of the nucleotide sequence), or a portion of any of these nucleotide sequences. In one embodiment, a nucleic acid molecule of the present invention comprises a nucleotide sequence which is at least (or no greater than) 50-100, 100-250, 250-500, 500-750, 750-1000, 1000-1250, 1250-1500, 1500-1750, 1750-2000, 2000-2250, 2250-2500, 2500-2750, 2750-3000, 3000-3250, 3250-3500 or more nucleotides in length and hybridizes under stringent hybridization conditions to a complement of a nucleic acid molecule of SEQ ID NO:1, SEQ ID NO:3, or SEQ ID NO:7, or alternatively SEQ ID NO: 5, SEQ ID NO:6, SEQ ID NO: 9, and/or SEQ ID NO:10.

Moreover, the nucleic acid molecule of the invention can comprise only a portion of the nucleic acid sequence of SEQ ID NO:1, SEQ ID NO:3, or SEQ ID NO:7, for example, a fragment which can be used as a probe or primer or a fragment encoding a portion of a Conlinin 1, Conlinin 2, and/or LuFad3 polypeptide, e.g., a biologically active portion of a Conlinin 1, Conlinin 2, and/or LuFad3 polypeptide. Alternatively, the nucleic acid molecule of the invention can comprise only a portion of the nucleic acid sequence of SEQ ID NO: 5, SEQ ID NO:6, SEQ ID NO: 9, and/or SEQ ID NO:10, for example, a fragment which can be used as a probe or primer or a fragment encoding a portion of a Conlinin 1, Conlinin 2, and/or LuFad3 promoter sequence, e.g. a portion of a Conlinin 1, Conlinin 2, or LuFad3 promoter which is capable of directing seed-specific gene expression. The nucleotide sequence determined from the cloning of the Conlinin 1, Conlinin 2, and/or LuFad3 gene or promoter region allows for the generation of probes and primers designed for use in identifying and/or cloning other Conlinin 1, Conlinin 2, and/or LuFad3 family members, as well as Conlinin 1, Conlinin 2, and/or LuFad3 homologues from other species. The probe/primer typically comprises substantially purified oligonucleotide. The probe/primer (e.g., oligonucleotide) typically comprises a region of nucleotide sequence that hybridizes under stringent conditions to at least about 12 or 15, preferably about 20 or 25, more preferably about 30, 35, 40, 45, 50, 55, 60, 65, 75, 80, 85, 90, 95, or 100 or more consecutive nucleotides of a sense sequence of SEQ ID NO:1, SEQ ID NO:3, or SEQ ID NO:7 of an anti-sense sequence of SEQ ID NO:1, SEQ ID NO:3, or SEQ ID NO:7, or of a naturally occurring allelic variant or mutant of SEQ ID NO:1, SEQ ID NO:3, or SEQ ID NO:7.

Exemplary probes or primers are at least 12, 15, 20, 25, 30, 35, 40, 45, 50, 55, 60, 65, 70, 75 or more nucleotides in length and/or comprise consecutive nucleotides of an isolated nucleic acid molecule described herein. Probes based on the Conlinin 1, Conlinin 2, and/or LuFad3 nucleotide sequences can be used to detect (e.g., specifically detect) transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of a Conlinin 1, Conlinin 2, and/or LuFad3 sequence, e.g., a domain, region, site or other sequence described herein. The primers should be at least 5, 10, 20, 30, 40, 50, 60, 70, 80, 90, 100 or more nucleotides in length. Such probes can be used as a part of a diagnostic test kit for identifying cells or tissue which misexpress a Conlinin 1, Conlinin 2, and/or LuFad3 polypeptide, such as by measuring a level of a Conlinin 1, Conlinin 2, and/or LuFad3-encoding nucleic acid in a sample of cells from a subject e.g., detecting Conlinin 1, Conlinin 2, and/or LuFad3 mRNA levels or determining whether a genomic Conlinin 1, Conlinin 2, and/or LuFad3 genie has been mutated or deleted.

A nucleic acid fragment encoding a "biologically active portion of a Conlinin 1 polypeptide" and/or a "biologically active portion of a Conlinin 2 polypeptide" or a "biologically active portion of a LuFad3 polypeptide" can be prepared by isolating a portion of the nucleotide sequence of SEQ ID NO:1, SEQ ID NO:3, or SEQ ID NO:7, which encodes a polypeptide having a Conlinin 1, Conlinin 2, and/or LuFad3 biological activity, expressing the encoded portion of the Conlinin 1, Conlinin 2, and/or LuFad3 polypeptide (e.g., by recombinant expression in vitro) and assessing the activity of the encoded portion of the Conlinin 1, Conlinin 2, and/or LuFad3 polypeptide. In an exemplary embodiment, the nucleic acid molecule is at least 50-100, 100-250, 250-500, 500-750, 750-1000, 1000-1250, 1250-1500, 1500-1750, 1750-2000, 2000-2250, 2250-2500, 2500-2750, 2750-3000, 3000-3250, 3250-3500 or more nucleotides in length and encodes a polypeptide having a LuFad3 activity (as described herein). In another exemplary embodiment, the nucleic acid molecule is at least 50-100, 100-250, 250-500, 500-750, 750-1000, 1000-1250, 1250-1500, 1500-1750, 1750-1850 or more nucleotides in length and encodes a polypeptide having a Conlinin 1 or Conlinin 2 activity.

In another embodiment, the invention features a nucleic acid fragment or portion of the Conlinin 1, Conlinin 2, or LuFad3 promoter sequences shown SEQ ID NO: 5, SEQ ID NO:6, SEQ ID NO: 9, and/or SEQ ID NO:10. A fragment of a promoter of the invention is any fragment which is capable of controlling expression of the gene which is operatively linked in a developing seed. In an exemplary embodiment, the nucleic acid molecule is at least 50-100, 100-250, 250-500, 500-750, 750-1000, 1000-1250, 1250-1500, 1500-1750, 1750-2000, 2000-2250, 2250-2500, 2500-2750, 2750-3000, 3000-3250, 3250-3500 or more nucleotides in length and encodes a promoter having LuFad3 promoter activity (as described herein). In another exemplary embodiment, the nucleic acid molecule is at least 50-100, 100-250, 250-500, 500-750, 750-1000, 1000-1250, 1250-1500, 1500-1750, 1750-1850 or more nucleotides in length and encodes a promoter having a Conlinin 1 or Conlinin 2 promoter activity (as described herein).

The invention further encompasses nucleic acid molecules that differ from the nucleotide sequence shown in SEQ ID NO:1, SEQ ID NO:3, or SEQ ID NO:7. Such differences can be due to due to degeneracy of the genetic code, thus resulting in a nucleic acid which encodes the same Conlinin 1, Conlinin 2, and/or LuFad3 polypeptides as those encoded by the nucleotide sequence shown in SEQ ID NO:1, SEQ ID NO:3, or SEQ ID NO:7. In another embodiment, an isolated nucleic acid molecule of the invention has a nucleotide sequence encoding a polypeptide having an amino acid sequence which differs by at least 1, but no greater than 5, 10, 20, 50 or 100 amino acid residues from the amino acid sequence shown in SEQ ID NO:2, SEQ ID NO:4, or SEQ ID NO:3. In yet another embodiment, the nucleic acid molecule encodes the amino acid sequence of flax Conlinin 1, Conlinin 2, and/or LuFad3. If an alignment is needed for this comparison, the sequences should be aligned for maximum homology.

Nucleic acid variants can be naturally occurring, such as allelic variants (same locus), homologies (different locus), and orthologues (different organism) or can be non naturally occurring. Non-naturally occuring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the flax population) that lead to changes in the amino acid sequences of the Conlinin 1, Conlinin 2, and/or LuFad3 polypeptides. Such genetic polymorphism in the Conlinin 1, Conlinin 2, and/or LuFad3 genes may exist among individuals within a population due to natural allelic variation. As used herein, the terms "gene" and "recombinant gene" refer to nucleic acid molecules which include an open reading frame encoding a Conlinin 1, Conlinin 2, and/or LuFad3 polypeptide, preferably a plant Conlinin 1, Conlinin 2, and/or LuFad3 polypeptide, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2, SEQ ID NO:4, or SEQ ID NO:8, wherein the nucleic acid molecule hybridizes to a complement of a nucleic acid molecule comprising SEQ ID NO:1, SEQ ID NO:3, or SEQ ID NO:7, for example, under stringent hybridization conditions.

Allelic variants of flax Conlinin 1, Conlinin 2, and/or LuFad3 include both functional and non-functional Conlinin 1, Conlinin 2, and/or LuFad3 polypeptides. Functional allelic variants are naturally occurring amino acid sequence variants of the flax Conlinin 1, Conlinin 2, and/or LuFad3 polypeptide that have a Conlinin 1, Conlinin 2, and/or LuFad3 activity, e.g., maintain the ability to bind a Conlinin 1, Conlinin 2, and/or LuFad3 substrate and/or modulate the formation of double bounds. Functional allelic variants will typically contain only conservative substitution of one or more amino acids of SEQ ID NO:2. SEQ ID NO:4, or SEQ ID NO:8, or substitution, deletion or insertion of non-critical residues in non-critical regions of the polypeptide.

Non-functional allelic variants are naturally occurring amino acid sequence variants of the flax Conlinin 1, Conlinin 2, and/or LuFad3 polypeptide that do not have a Conlinin 1, Conlinin 2, and/or LuFad3 activity, e.g., they do not have the ability to introduce a double bond into a fatty acid. Non-functional allelic variants will typically contain a non-conservative substitution, a deletion, or insertion or premature truncation of the amino acid sequence of SEQ ID NO:2, SEQ ID NO:4, or SEQ ID NO:8, or a substitution, insertion or deletion in critical residues or critical regions.

The present invention further provides non-flax orthologues of the flax Conlinin 1, Conlinin 2, and/or LuFad3 polypeptide. Orthologues of flax Conlinin 1, Conlinin 2, and/or LuFad3 polypeptides are polypeptides that are isolated from non-flax organisms and possess the same Conlinin 1, Conlinin 2, and/or LuFad3 activity, e.g., ability to introduce double bonds into a fatty acid, as the flax Conlinin 1, Conlinin 2, and/or LuFad3 polypeptide. Orthologues of the flax Conlinin 1, Conlinin 2, and/or LuFad3 polypeptide can readily be identified as comprising an amino acid sequence that is substantially identical to SEQ ID NO:2, SEQ ID NO:4, or SEQ ID NO:5.

Moreover, nucleic acid molecules encoding other Conlinin 1, Conlinin 2, and/or LuFad3 family members and, thus, which have a nucleotide sequence which differs from the Conlinin 1, Conlinin 2, and/or LuFad3 sequences of SEQ ID NO:1, SEQ ID NO: 3, or SEQ ID NO:7 are intended to be within the scope of the invention. For example, another Conlinin 1, Conlinin 2, and/or LuFad3 cDNA can be identified based on the nucleotide sequence of flax Conlinin 1, Conlinin 2, and/or LuFad3. Moreover, nucleic acid molecules encoding Conlinin 1, Conlinin 2, and/or LuFad3 polypeptides from different species, and which, thus, have a nucleotide sequence which differs from the Conlinin 1, Conlinin 2, and/or LuFad3 sequences of SEQ ID NO:1, SEQ ID NO:3, or SEQ ID NO:7 are intended to be within the scope of the invention.

Nucleic acid molecules corresponding to natural allelic variants and homologues of the Conlinin 1, Conlinin 2, and/or LuFad3 cDNAs of the invention can be isolated based on their homology to the Conlinin 1, Conlinin 2, and/or LuFad3 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the Conlinin 1, Conlinin 2, and/or LuFad3 cDNAs of the t invention can further be isolated by mapping to the same chromosome or locus as the Conlinin 1, Conlinin 2, and/or LuFad3 gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, or SEQ ID NO:7. In other embodiment, the nucleic acid is at least 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2500, 2500-3000, 3000-3500 or more nucleotides in length. In other embodiment, the nucleic acid is at least 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450; 1450-1500, 1500-1550, 1550-1600, 1600-1650, 1650-1700, 1700-1750, 1750-1800, 1800-1850 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+ 4(# of G+C bases). For hybrids between 18 and 49 base pairs in length, $T_m$(° C.) 81.5+16.6($\log_{10}$[Na$^+$])+0.41(% G+C)− (600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or alternatively 0.2×SSC, 1% SDS).

Preferably, an isolated nucleic acid molecule of the invention that hybridizes under stringent conditions to the sequence of SEQ ID NO:1, SEQ ID NO:3, or SEQ ID NO:7 and corresponds to a naturally-occurring nucleic acid molecule. In another preferred embodiment, an isolated nucleic acid molecule of the invention that hybridizes under stringent conditions to the sequence of SEQ ID NO:5, SEQ ID NO:6, or SEQ ID NO:9, or SEQ ID NO:10, and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural polypeptide).

In addition to naturally-occurring allelic variants of the Conlinin 1, Conlinin 2, and/or LuFad3 sequences that may exist in the population, the skilled artisan will further appreciate that changes can be introduced by mutation into the nucleotide sequences of SEQ ID NO:1, SEQ ID NO:3, or SEQ ID NO:7, thereby leading to changes in the amino acid sequence of the encoded Conlinin 1, Conlinin 2, and/or LuFad3 polypeptides, without altering the functional ability of the Conlinin 1, Conlinin 2, and/or LuFad3 polypeptides. For example, nucleotide substitutions leading to amino acid substitutions at "non-essential" amino acid residues can be made in the sequence of SEQ ID NO:1, SEQ ID NO:3, or SEQ ID NO:7. A "non-essential"[1] amino acid residue is a residue that can be altered from the wild-type sequence of Conlinin 1, Conlinin 2, and/or LuFad3 (e.g., the sequence of SEQ ID NO:2, SEQ ID NO:4, or SEQ ID NO:8) without altering the biological activity, whereas an "essential" amino acid residue is required for biological activity. Furthermore, additional amino acid residues that are conserved between the Conlinin 1, Conlinin 2, and/or LuFad3 polypeptides of the present invention and other members of the Conlinin 1, Conlinin 2, and/or LuFad3 family are not likely to be amenable to alteration.

Accordingly, another aspect of the invention pertains to nucleic acid molecules encoding Conlinin 1, Conlinin 2, and/or LuFad3 polypeptides that contain changes in amino acid residues that are not essential for activity. Such Conlinin 1, Conlinin 2, and/or LuFad3 polypeptides differ in amino acid sequence from SEQ ID NO:2, SEQ ID NO:4, or SEQ ID NO:8, yet retain biological activity. In one embodiment, the isolated nucleic acid molecule comprises a nucleotide sequence encoding a polypeptide, wherein the polypeptide comprises an amino acid sequence at least about 50%, 55%, 60%, 65%, 70%, 75%, 80%, 85%, 90%, 95%, 96%, 97%, 98%, 99% or more identical to SEQ ID NO:2, SEQ ID NO:4, or SEQ ID NO:8. In another embodiment, the isolated nucleic acid molecule comprises a nucleotide sequence encoding a promoter region, wherein the polypeptide comprises an amino acid sequence at least about 50%, 55%, 60%, 65%, 70%, 75%, 80%, 85%, 90%, 95%, 96%, 97%, 98%, 99% or more identical to SEQ ID NO:5, SEQ ID NO:6, SEQ ID NO:9, or SEQ ID NO:10.

An isolated nucleic acid molecule encoding a Conlinin 1, Conlinin 2, and/or LuFad3 polypeptide identical to the polypeptide of SEQ ID NO:2, SEQ ID NO:4, or SEQ ID NO:3, can be created by introducing one or more nucleotide substitutions, additions or deletions into the nucleotide sequence of SEQ ID NO:1, SEQ ID NO:3, or SEQ ID NO:7, such that one or more amino acid substitutions, additions or deletions are introduced into the encoded polypeptide. Mutations can be introduced into SEQ ID NO:1, SEQ ID NO:3, or SEQ ID NO:7 such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a Conlinin 1, Conlinin 2, and/or LuFad3 polypeptide is preferably replaced with another amino acid residue from the same side chain family. Alternatively, in another embodiment, mutations can be introduced randomly along all or part of a Conlinin 1, Conlinin 2, and/or LuFad3 coding sequence, such as by saturation mutagenesis, and the resultant mutants can be screened for Conlinin 1, Conlinin 2, and/or LuFad3 biological activity to identify mutants that retain activity. Following mutagenesis of SEQ ID NO:1, SEQ ID NO:3, or SEQ ID NO:7, the encoded polypeptide can be expressed recombinantly and the activity of the polypeptide can be determined.

In addition to the nucleic acid molecules encoding Conlinin 1, Conlinin 2, and/or LuFad3 polypeptides described above, as well as the promoter regions of these genes, another aspect of the invention pertains to isolated nucleic acid molecules which are antisense thereto. In an exemplary embodiment, the invention provides an isolated nucleic acid molecule which is antisense to a Conlinin 1, Conlinin 2, and/or LuFad3 nucleic acid molecule (e.g., is antisense to the coding strand of a Conlinin 1, Conlinin 2, and/or LuFad3 nucleic acid molecule). An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Conlinin 1, Conlinin 2, and/or LuFad3 coding stand, or to only a portion thereof. In one embodiment, an antisense nucleic acid molecule is antisense to a "coding region" of the coding strand of a nucleotide sequence encoding Conlinin 1, Conlinin 2, and/or LuFad3. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding Conlinin 1, Conlinin 2, and/or LuFad3. The term "noncoding region" refers to 5' and 3' sequences which flank the coding region that are not translated into amino acids (i.e., also referred to as 5' and 3' untranslated regions).

Given the coding strand sequences encoding Conlinin 1, Conlinin 2, and/or LuFad3 disclosed herein, antisense nucleic acids of the invention can be designed Fen according to the rules of Watson and Crick base pairing. Similar methods can be applied to the promoters described in the invention, whereby antisense molecules interfere with specific control regions within the promoter. The antisense nucleic acid molecule can be complementary to the entire coding region of Conlinin 1, Conlinin 2, and/or LuFad3 mRNA, but more preferably is an oligonucleotide which is antisense to only a portion of the coding or non-coding region of Conlinin 1, Conlinin 2, and/or LuFad3 mRNA. For example, the antisense oligonucleotide can be complementary to the region surrounding the translation start site of Conlinin 1, Conlinin 2, and/or LuFad3 mRNA (e.g., between the −10 and +10 regions of the start site of a gene nucleotide sequence). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically generated in situ such that they hybridize with or bind to cellular mRNA and/or genomic DNA encoding a Conlinin 1, Conlinin 2, and/or LuFad3 polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells. For example, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intra-cellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave Conlinin 1, Conlinin 2, and/or LuFad3 mRNA transcripts to thereby inhibit translation of Conlinin 1, Conlinin 2, and/or LuFad3 mRNA. A ribozyme having specificity for a Conlinin 1, Conlinin 2, and/or LuFad3-encoding nucleic acid can be designed based upon the nucleotide sequence of a Conlinin 1, Conlinin 2, and/or LuFad3 cDNA disclosed herein (i.e., SEQ ID NO:1, SEQ ID NO:3, or SEQ ID NO:7). For example, a derivative of a Tetrahymena L-19 IVS RNA can be constructed in which the nucleotide sequence of the active site is complementary to the nucleotide sequence to be cleaved in a Conlinin 1, Conlinin 2, and/or LuFad3-encoding mRNA. See, egA, Cech et al. U.S. Pat. No. 4,987,071; and Cech et al. U.S. Pat. No. 5,116,742. Alternatively, Conlinin 1, Conlinin 2, and/or LuFad3 mRNA can be used to select a catalytic RNA having a specific ribonuclease activity from a pool of RNA molecules. See, e.g., Bartel, D. and Szostak, J. W. (1993) *Science* 261:1411-1418.

Alternatively, Conlinin 1, Conlinin 2, and/or LuFad3 gene expression can be inhibited by targeting nucleotide sequences complementary to the regulatory region of the Conlinin 1, Conlinin 2, and/or LuFad3 (erg, the Conlinin 1, Conlinin 2, and/or LuFad3 promoter and/or enhancers) to form triple helical structures that prevent transcription of the Conlinin 1, Conlinin 2, and/or LuFad3 gene in target cells. See generally, Helene, C. (1991) *Anticancer Drug Des.* 6(6):569-84; Helene, C. et al. (1992) *Ann. N Y Acad. Sci.* 660:27-36; and Maher, L. J. (1992) *Bioassays* 14(12):807-15.

In yet another embodiment, the Conlinin 1, Conlinin 2, and/or LuFad3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et at. *Proc. Natl. Acad. Sci.* 93: 14670-675.

PNAs of Conlinin 1, Conlinin 2, and/or LuFad3 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of Conlinin 1, Conlinin 2, and/or LuFad3 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of Conlinin 1, Conlinin 2, and/or LuFad3 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of Conlinin 1, Conlinin 2, and/or LuFad3 nucleic acid molecules can be generated which may combine the advantageous properties of PNA and DNA. Such chimeras a low DNA recognition enzymes, (e.g., RNase H and DNA polymerases), to interact with the DNA portion while the PNA portion would provide high binding affinity and specificity. PNA-DNA chimeras can be lied using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et at. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al (1989) *Nucleic Acid Res.* 17: 5973-88). PNA monomers are then coupled in a stepwise manner to produce a chimeric molecule with a 5' PNA segment and a 3' DNA segment (Finn P. J. et al (1996) supra). Alternatively, chimeric molecules can be synthesized with a 5' DNA segment and a 3' PNA segment (Peterser, K. H. et al (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958-

976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous Conlinin 1, Conlinin 2, and/or LuFad3 gene within a cell line or microorganism may be modified by inserting a heterologous DNA regulatory element into the genome of a stable cell line or cloned microorganism such that the inserted regulatory element is operatively linked with the endogenous Conlinin 1, Conlinin 2, and/or LuFad3 gene. For example, an endogenous Conlinin 1, Conlinin 2, and/or LuFad3 gene which is normally "transcriptionally silent", i.e., a Conlinin 1, Conlinin 2, and/or LuFad3 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous Conlinin 1, Conlinin 2, and/or LuFad3 gene may be activated by insertion of a promiscuous regulatory element that works across cell types.

A heterologous regulatory element may be inserted into a stable cell line or cloned microorganism, such that it is operatively linked with an endogenous Conlinin 1, Conlinin 2, and/or LuFad3 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated Conlinin 1, Conlinin 2, and LuFad3 Polypeptides

One aspect of the invention pertains to isolated Conlinin 1, Conlinin 2, and/or LuFad3 or recombinant polypeptides and polypeptides, and biologically active portions thereof, as well as polypeptide fragments suitable for use as immunogens to raise anti-Conlinin 1, Conlinin 2, and/or LuFad3 antibodies. In one embodiment, native Conlinin 1, Conlinin 2, and/or LuFad3 polypeptides can be isolated from cells or tissue sources by an appropriate purification scheme using standard protein purification techniques. In another embodiment, Conlinin 1, Conlinin 2, and/or LuFad3 polypeptides are produced by recombinant DNA techniques. Alternative to recombinant expression a Conlinin 1, Conlinin 2, and/or LuFad3 polypeptide or polypeptide can be synthesized chemically using standard peptide synthesis techniques.

An "isolated" or "purified" polypeptide or biologically active portion thereof is substantially fire of cellular material or other contaminating proteins from the cell or tissue source from which the Conlinin 1, Conlinin 2, and/or LuFad3 polypeptide is derived, or substantially free from chemical precursors or other chemicals when chemically synthesized. The language "substantially free of cellular material" includes preparations of Conlinin 1, Conlinin 2, and/or LuFad3 polypeptide in which the polypeptide is separated from cellular components of the cells from which it is isolated or recombinantly produced. In one embodiment, the language "substantially free of cellular material" includes preparations of Conlinin 1, Conlinin 2, and/or LuFad3 polypeptide having less than about 30% (by dry weight) of non-Conlinin 1, Conlinin 2, and/or LuFad3 polypeptide (also referred to herein as a "contaminating protein"), more preferably less than about 20% of non-Conlinin 1, Conlinin 2, and/or LuFad3 polypeptide, still more preferably less than about 10% of non-Conlinin 1 Conlinin 2, and/or LuFad3 polypeptide, and most preferably less than about 5% non-Conlinin 1, Conlinin 2, and/or LuFad3 polypeptide. When the Conlinin 1, Conlinin 2, and/or LuFad3 polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Conlinin 1, Conlinin 2, and/or LuFad3 polypeptide in which the polypeptide is separated from chemical precursors or other chemicals which are involved in the synthesis of the polypeptide. In one embodiment, the language "substantially free of chemical precursors or other chemicals" includes preparations of Conlinin 1, Conlinin 2, and/or LuFad3 polypeptide having less than about 30% (by dry weight) of chemical precursors or non-Conlinin 1, Conlinin 2, and/or LuFad3 chemicals, more preferably less than about 20% chemical precursors or non-Conlinin 1, Conlinin 2, and/or LuFad3 chemicals, still more preferably less than about 10% chemical precursors or non-Conlinin 1, Conlinin 2, and/or LuFad3 chemicals, and most preferably less than about 5% chemical precursors or non-Conlinin 1, Conlinin 2, and/or LuFad3 chemicals.

As used-herein, a "biologically active portion" of a Conlinin 1, Conlinin 2, and/or LuFad3 polypeptide includes a fragment of a Conlinin 1, Conlinin 2, and/or LuFad3 polypeptide which participates in an interaction between a Conlinin 1, Conlinin 2, and/or LuFad3 molecule and a non-Conlinin 1, Conlinin 2, and/or LuFad3 molecule. Biologically active portions of a Conlinin 1, Conlinin 2, and/or LuFad3 polypeptide include peptides comprising amino acid sequences sufficiently identical to or derived from the amino acid sequence of the Conlinin 1, Conlinin 2, and/or LuFad3 polypeptide, e.g., the amino acid sequence shown in SEQ ID NO:2, SEQ ID NO:4, or SEQ ID NO:8, which include less amino acids than the fill length Conlinin 1, Conlinin 2, and/or LuFad3 polypeptides, and exhibit at least one activity of a Conlinin 1, Conlinin 2, and/or LuFad3 polypeptide. Typically, biologically active portions comprise a domain or motif with at least one activity of the Conlinin 1, Conlinin 2, and/or LuFad3 polypeptide, e.g., modulating double bonds in fatty acids. A biologically active portion of a Conlinin 1, Conlinin 2, and/or LuFad3 polypeptide can be a polypeptide which is, for example, 25, 30, 35, 40, 45, 50, 75, 100, 125, 150, 175, 200, 225, 250, 275, 300, 325, 350, 375 or more amino acids in length. Biologically active portions of a Conlinin 1, Conlinin 2, and/or LuFad3 polypeptide can be used as targets for developing agents which modulate a Conlinin 1, Conlinin 2, and/or LuFad3 mediated activity, e.g., modulating double bonds in fatty acids.

Another aspect of the invention features fragments of the polypeptide having the amino acid sequence of SEQ ID NO:2, SEQ ID NO:4, or SEQ ID NO:8, for example, for use as immunogens. In one embodiment, a fragment comprises at least 5 amino acids (e.g., contiguous or consecutive amino acids) of the amino acid sequence of SEQ ID NO:2, SEQ ID NO:4, or SEQ ID NO:8. In another embodiment, a fragment comprises at least 10, 15, 20, 25, 30, 35, 40, 45, 50 or more amino acids (e.g., contiguous or consecutive amino acids) of the amino acid sequence of SEQ ID NO:2, SEQ ID NO:4, or SEQ ID NO:8.

In a preferred embodiment, a Conlinin 1, Conlinin 2, and/or LuFad3 polypeptide has an amino acid sequence shown in SEQ ID NO:2, SEQ ID NO:4, or SEQ ID NO:8. In other embodiments, the Conlinin 1, Conlinin 2, and/or LuFad3 polypeptide is substantially identical to SEQ ID NO:2, SEQ ID NO:4, or SEQ ID NO:8, and retains the functional activity of the polypeptide of SEQ ID NO:2, SEQ ID NO:4, or SEQ ID NO:8, yet differs in amino acid sequence due to natural allelic variation or mutagenesis, as described in detail in subsection I above. In another embodiment, the Conlinin 1, Conlinin 2, and/or LuFad3 polypeptide is a polypeptide which comprises an amino acid sequence at least about 50%, 55%, 60%, 65%, 70%, 75%, 80%, 85%, 90%, 95%, 96%, 97%, 98%, 99% or more identical to SEQ ID NO:2, SEQ ID NO:4, or SEQ ID NO:8.

In another embodiment, the invention features a Conlinin 1, Conlinin 2, and/or LuFad3 polypeptide which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:1, SEQ ID NO:3, or SEQ ID NO:7, or a complement thereof. This invention further features a Conlinin 1, Conlinin 2, and/or LuFad3 polypeptide which is encoded by a nucleic acid molecule consisting of a nucleotide sequence which hybridizes under stringent hybridization conditions to a complement of a nucleic acid molecule comprising the nucleotide sequence of SEQ ID NO:1, SEQ ID NO:3, or SEQ ID NO:7, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the LuFad3 amino acid sequence of SEQ ID NO:8 having 392 amino acid residues, at least 117, preferably at least 156, more preferably at least 196, more preferably at least 235, even more preferably at least 274, and even more preferably at least 313 or 352 or more amino acid residues are aligned; when aligning a second sequence to the Conlinin 1 or Conlinin 2 amino acid sequence of SEQ ID NO:2 having 168 amino acid residues and SEQ ID NO:4 having 169 amino acids, respectively, at least 51, preferably at least 67, more preferably at least 85, more preferably at least 101, even more preferably at least 118, and even more preferably at least 135 or 152 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 12, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of E. Meyers and W. Miller (*Comput. Appl. Biosci.*, 4:11-17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to Conlinin 1, Conlinin 2, or LuFad3 nucleic acid molecules of the invention. BLAST protein searches can be performed with the XBLAST program, score=100, wordlength=3, and a Blosum62 matrix to obtain amino acid sequences homologous to Conlinin 1, Conlinin 2, or LuFad3 polypeptide molecules of the invention. To obtain gapped alignments for comparison purposes, Gapped BLAST can be utilized as described in Altschul et al, (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The invention also provides Conlinin 1, Conlinin 2, and/or LuFad3 chimeric or fusion proteins. As used herein, a Conlinin 1, Conlinin 2, and/or LuFad3 "chimeric protein" or "fusion protein" comprises a Conlinin 1, Conlinin 2, and/or LuFad3 polypeptide operatively linked to a non-Conlinin 1, Conlinin 2, and/or LuFad3 polypeptide. A "Conlinin 1 polypeptide", a "Conlinin 2 polypeptide", and a "LuFad3 polypeptide" refers to a polypeptide having an amino acid sequence corresponding to Conlinin 1, Conlinin 2, and Lufad3, respectively, whereas a "non-Conlinin 1 polypeptide", a "non-Conlinin 2 polypeptide", and a "non-LuFad3 polypeptide" refers to a polypeptide having an amino acid sequence corresponding to a polypeptide which is not substantially homologous to the Conlinin 1, Conlinin 2, and LuFad3 polypeptides, respectively, e.g., a polypeptide which is different from the Conlinin 1, Conlinin 2, or LuFad3 polypeptide and which is derived from the same or a different organism. Within a Conlinin 1, Conlinin 2, and/or LuFad3 fusion protein the Conlinin 1, Conlinin 2, and/or LuFad3 polypeptide can correspond to all or a portion of a Conlinin 1, Conlinin 2, and/or LuFad3 polypeptide. In a preferred embodiment, a Conlinin 1, Conlinin 2, and/or LuFad3 fusion protein comprises at least one biologically active portion of a Conlinin 1, Conlinin 2, and/or LuFad3 polypeptide. In another preferred embodiment, a Conlinin 1, Conlinin 2, and/or LuFad3 fusion protein comprises at least two biologically active portions of a Conlinin 1, Conlinin 2, and/or LuFad3 polypeptide. Within the fusion protein, the term "operatively linked" is intended to indicate that the Conlinin 1, Conlinin 2, and/or LuFad3 polypeptide and the non-Conlinin 1, Conlinin 2, and/or LuFad3 polypeptide are fused in-frame to each other. The non-Conlinin 1, Conlinin 2, and/or LuFad3 polypeptide can be fused to the N-terminus or C-terminus of the Conlinin 1, Conlinin 2, and/or LuFad3 polypeptide.

For example, in one embodiment, the fusion protein is a GST-Conlinin 1 and/or GST-Conlinin 2 and/or GST-LuFAd3 fusion protein in which the Conlinin 1, Conlinin 2, and/or LuFad3 sequences are used to the C-terminus of the GST sequences. Such fusion proteins can facilitate the purification of recombinant Conlinin 1, Conlinin 2, and/or LuFad3.

In another embodiment, the fusion protein is a Conlinin 1, Conlinin 2, and/or LuFad3 polypeptide containing a heterologous signal sequence at its N-terminus. In certain host cells (e.g., mammalian host cells), expression and/or secretion of Conlinin 1, Conlinin 2, and/or LuFad3 can be increased through the use of a heterologous signal sequence.

III. Transgenic Plants

In another embodiment, the invention provides transgenic plants containing nucleic acids of the invention. In one embodiment, the transgenic plant contains the nucleotide sequence encoding the Conlinin 1, Conlinin 2, and/or Lufad3 polypeptides of the invention. In another embodiment, the invention further describes transgenic plants containing promoter sequences of Conlinin 1, Conlinin 2, and or LuFad3 operatively linked to a gene of interest, preferably a gene involved in lipid biosynthesis. In order to introduce nucleic acid sequences into plant cells in general a variety of techniques are available to the skilled artisan. *Agrobacterium*-mediated transformation for flax plant cells has been reported and flax transformants may be obtained in accordance with the methods taught by Dong and McHughen (1993) Plant Science 88: 61-77, although a variety of other techniques may also be used to introduce the chimeric DNA constructs in flax cells if so desired.

Transformed flax plants grown in accordance with conventional agricultural practices known to a person skilled in the art are allowed to set seed. Flax seed may then be obtained from mature flax plants and analyzed for desired altered properties with respect to the wild-type seed.

Two or more generations of plants may be grown and either crossed or selfed to allow identification of plants and strains with desired phenotypic characteristics including production of the recombinant polypeptide. It may be desirable to ensure homozygosity in the plants to assure continued inheritance of the recombinant trait. Methods for selecting homozygous plants are well known to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means (e.g. treatment with colchicine or other microtubule disrupting agents).

Furthermore, a variety of techniques are available for the introduction of nucleic acid sequences, in particular DNA, into plant host cells in general. For example, the chimeric DNA constructs may be introduced into host cells obtained from dicotelydenous plants, such as tobacco, and oleoagenous species, such as *Brassica napus* using standard *Agrobacterium* vectors by a transformation protocol such as described by Moloney et al (1989), Plant Cell Rep. 8: 238-242 or Hinchee et al. (1988) Bio/Technol. 6: 915-922; or other techniques known to those skilled in the art. For example, the use of T-DNA for transformation of plant cells has received extensive study and is amply described in EP 0 120 516, Hoekema et al., (1985), Chapter V In: *The Binary Plant Vector System* Offset-drukkerij Kanters B V, Alblasserdam); Knauf et al. (1983), *Genetic Analysis of Host Expression by Agrobacterium*, p. 245, In: *Molecular Genetics of Bacteria-Plant Interaction*, Puhler, A. ed. Springer-Verlag, NY); and An et al., (1985), (EMBO J., 4: 277-284). *Agrobacterium* transformation may also be used to transform monocot plant species (U.S. Pat. No. 5,591,616).

Explants may be cultivated with *Agrobacterium tumefaciens* or *Agrobacterium rhizogenes* to allow for the transfer of the transcription construct in the plant host cell. Following transformation using *Agrobacterium* the plant cells are dispersed into an appropriate medium for selection, subsequently callus, shoots and eventually plants are recovered. The *Agrobacterium* host will harbour a plasmid comprising the vir genes necessary for transfer of the T-DNA to plant cells. For injection and electroporation (see below) disarmed Ti-plasmids (lacking the tumour genes, particularly the T-DNA region) may be introduced into the plant cell.

The use of non-*Agrobacterium* techniques permits the use of constructs described herein to obtain transformation and expression in a wide variety of monocotyledonous and dicotyledonous plant species. These techniques are especially useful for transformation of plant species that are intractable in an *Agrobacterium* transformation system. Other techniques for gene transfer include particle bombardment (Sanford, (1988), Trends in Biotechn. 6: 299-302), electroporation (Fromm et al., (1985), PNAS USA, 82: 5824-5828; Riggs and Bates, (1986), PNAS USA 83: 5602-5606), PEG mediated DNA uptake (otrykus et al., (1985), Mol. Gen. Genetics., 199: 169-177), microinjection (Reich et al., Bio/Techn. (1986) 4:1001-1004) and silicone carbide whiskers (Kaeppler et al. (1990) Plant Cell Rep. 9: 415-418).

In a further specific applications such as to *B. napus*, the host cells targeted to receive recombinant DNA constructs typically will be derived from cotyledonary petioles as described by Moloney et al (1989) Plant Cell Rep. 8: 238-242 Other examples using commercial oil seeds include cotyledon transformation in soybean explants (Hinchee et al, (1988) Bio/Technol. 6: 915-922) and stem transformation of cotton (Umbeck et al, (1987) Bio/Technol. 5: 263-266).

Following transformation, the cells, for example as leaf discs, are grown in selective medium. Once the shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, to show integration into the genome of the host cell.

The methods provided by the present invention can be used in conjunction a broad range of plant species. Particularly preferred plant cells employed in accordance with the present invention include cells from the following plants: soybean (*Glycine max*), rapeseed (*Brassica napus, Brassica campestris*), sunflower (*Helianthus annuus*), cotton (*Gossypium hirsutum*), corn (*Zea mays*), tobacco (*Nicotiana tobacum*), alfalafa (*Medicago sativa*), wheat (*Triticum* sp.), barley (*Hordeum vulgare*), oats (*Avena sativa* L.), sorghum (*Sorghum bicolor*), *Arabidopsis thatiana*, potato (*Solanum* sp.), flax/linseed (*Linum usitatissimum*), safflower (*Carthamus tinctorius*), oil palm (*Eleais guineeks*), groundnut (*Arachis hypogaea*), Brazil nut (*Bertholletia excelsa*) coconut (*Cocus nucifera*), castor (*Ricinus communis*), coriander (*Coriandrum sativum*), squash (*Cucurbita maxima*), jojoba (*Simmondsia chinensis*) and rice (*Oryza sativa*).

Another embodiment of the invention includes a transgenic plant containing a transgene comprising a nucleic acid containing a seed-specific promoter which is operatively linked to a gene of interest, preferably a gene involved in lipid biosynthesis. In a preferred embodiment of the invention, the transgenic plant produces fatty acids which can then be ioalted and/or purified according to the methods described previously.

This invention is farther illustrated by the following examples which should not be construed as limiting. The contents of all references, patents and published patent applications cited throughout this application are incorporated herein by reference.

EXAMPLES

General Methodology

Plant Material

Linseed flax (*Linum usitatissimum* L.) cultivar CDC Normandy and S93-708 were grown in the growth chamber under standard conditions. Developing seeds were harvested at different days after flowering (OAF) and used for embryo excision, RNA isolation and the construction of the cDNA library. Fifteen-day-old seedlings of the same varieties were also used for the isolation of genomic DNA and construction of flax genomic library.

RNA Isolation

Leaves, stems, roots and developing seeds at various DAF were collected and frozen in liquid nitrogen immediately and kept at −80° C. Total RNA was extracted by using RNeasy plant mini kit (Qiagen). Embryos released from the developing seeds were homogenized with extraction solution RLC in the kit. Total RNA was eluted with RNase-free water and its concentration was determined by spectrophotometer.

cDNA Library Preparation and Screening

The total RNA was extracted from flax embryo without seed coats by RNeasy Plant Mini kit (Qiagen, Hilden, Germany). The mRNA enrichment was done by Dynabeads Oligo $dT_{(25)}$ (Dynal, Oslo, Norway). Obtained mRNA was then used for the cDNA synthesis by ZAP-cDNA synthesis kit and construction of the library in the Uni-Zap XR EcoRI and XhoI predigested lambda vector (Stratagene, La Jolla, USA).

cDNA library was plated on large square plates (24×24 cm) and approximately $6 \times 10^4$ clones were screened by using $^{32}$P-labelled probes prepared from double-stranded cDNAs originating from the flax embryo in the same developmental stage as used in the library construction and from 15-day-old seedlings. 1152 differentially expressed clones giving a strong signal when hybridized with the embryo probe and none or background level with the seedling cDNA probe were isolated and stored in the ordered manner on microtitre plates. To perform classification and grouping of isolated clones, 96-format PCR amplification of the inserts (vector specific primers T3 and T7) was performed and the PCR products were transferred on a positively charged nylon membrane (Boehringer Mannheim, Germany) by dot-blotting. Resulting dot blots (each carrying 192 clones) were then hybridized with biotin-labeled (Biotin Chem-Link, Boehringer Mannheim, Germany) randomly chosen inserts. Selected lambda clones were then converted into plasmids via in-vivo excision and sequenced. Similarity analysis was performed by BLAST searches utilizing both blastn and blastx programs to search databases of nucleotide and protein sequences, respectively.

For identifying the desaturase cDNA clones, the embryo cDNA library was screened by degenerate PCR amplified fragment probes. Two degenerate primers 5'-AT(ACGT) T(GT)(ACGT) GG(AG) AA(ACGT) A(GA)(GA) TG(AG) TG-3' (SEQ ID NO:12) and 5'-(AG)T(AGCT) GG(AGCT) CA(TC) GA(TC) TG(TC) GG(AGCT) CA-3' (SEQ ID NO: 13) were designed to target two histidine-rich motifs in microsomal desaturases. PCR conditions were set up for 4 min at 95° C., followed by 30 cycles of denaturing for 1 min at 94(C, annealing for 1 min at 50° C., and extension for 2 min at 72° C. The amplified fragments were purified from agarose gel by gel purification kit (Qiagen) and cloned into TA cloning vector (Invitrogen).

Flax Genomic Library Preparation and Screening

High molecular genomic DNA was isolated from 15-day-old seedlings using the modified CTAB procedure combined with Qiagen Genomic Tip purification procedures (Qiagen, Hilden, Germany). Genomic DNA was partially digested with MboI, phenol-chloroform extracted and then partially filled with dGTP and dATP. Size fractionation was done on sucrose gradient. The fraction containing DNA fragments between 16-21 kb was then cloned into Lambda Fix II XhoI predigested vector (Stratagene, La Jolla, USA).

The library was plated on top agarose at high density (approximately half a million of pfu per 15-cm plate). Approximately $8 \times 10^5$ clones were screened by $^{32}$P-labelled cDNA probes. The positive clones were subcloned and sequenced.

Northern Blot Analysis

Equal amount of total RNAs from different samples was applied to the denatured agarose gel (Formaldehyde gel) which contains 1×MOPs buffer, 3% of formaldehyde. The gel was run in 1×MOPs buffer at 65 V for about 1.5 hours. After electrophoresis, the RNA was transferred to Hybond NX+membrane with 10×SSC using the downward transfer system for about 3 hr. The membrane was then submerged in DEPC-treated water for 1 min and cross-linked by an UV Stratalinker. The membrane was prehybridized in 10 ml of QuikHyb (Stratagene) at 68° C. for 15 min. and then hybridized by $^{32}$P-labeled probes ($1 \times 10^6$ cpm/ml) at 68° C. for 2 hr. The membrane was washed once at 50° C. for 30 min with a 2×SSC and 0.1% SDS washing solution, and then washed once at 60° C. for 30 min with a 0.1×SSC and 0.1% (w/v) SDS washing solution. The hybridized membrane was exposed to an X-ray film with an intensifying screen at −80° C. overnight.

Southern Blot Analysis

Purified genomic DNA of flax was restricted with BamHI or EcoRI overnight at 37° C. The restricted samples were applied to a 1% (w/v) agarose gel and run at constant voltage of 65 V for about 2 hours. The DNA fragments in the gel were transferred to a nylon membrane Hybond-NX (Amersham) with a solution of 0.25 N NaOH and 1.5 M NaCl by the downward transferring system. The genomic DNA was UV cross-linked to the membrane. The prehybridization and hybridization procedures were the same as the northern blot analysis.

Construction of Binary Vector

About 1 kb sequence located upstream the coding region was amplified by PCR using two primers with the HindIII and XbaI restriction sites added to their 5' ends, respectively. To reduce the probability of base mis-incorporation, the recombinant thermostable DNA polymerase DyNAzyme EXT (Finnzymes, Espoo, Finland) was used in PCR amplification. The PCR product was first cloned into pCR21 (TA cloning system, Invitrogen, Carlsbad, USA), then excised by HindIII and XbaI and subcloned into pBIN19 based binary vector. The promoter sequence was placed in front of β-glucuronidase (uidA, GUS) reporter gene in the pBIN19-based plant transformation vector, replacing original CaMV 35S promoter.

Flax Transformation

Hypocotyls as flax explants were inoculated with *Agrobacterium tumefaciens* strain GV3101 (pNT90) harboring binary vectors. The transformants were selected on the medium containing kanamycin and the escape shoots were eliminated by the combination of radioactive NPTII assay, PCR of the uidA gene and the regeneration assay on the medium containing 150 mg/l kanamycin.

Transgenic plants were grown in a growth chamber under the standard condition-Upon flowering, individual flowers were labeled. The developing seeds were harvested for GUS activity assay. Being removed from the capsule, some seeds were stained entirely and others were dissected into the seed coat and the developing embryo. The leaves, stems and roots of the transgenic plants were also enclosed in the assay to assess the tissue specificity of the promoter. The GUS substrate was infiltrated into the tissues by mild vacuum and the tissues were incubated at 37° C. overnight. After the incubation, the tissue pieces were fixed, bleached and observed under stereomicroscope.

Transformation of *Arabidopsis thaliana*

Saturated liquid culture of *Agrobacterium tumefaciens* GV3101 strain harboring the binary vector and helper plasmid pMP90 was used to infiltrate plants of *A. thaliana* ecotype Columbia. Several hundred developing T1 seeds were stained for GUS activity and observed under stereomicroscope to assess tissue specificity of the flax promoter.

Histochemical GUS Staining and Fluorometric GUS Assay

Transgenic plants were grown in a growth chamber under the standard condition. Upon flowering, individual flowers were labeled. The developing seeds were harvested for GUS staining. Being removed from the capsule, some seeds were stained entirely and others were dissected into the seed coat and the developing embryo. The leaves, stems and roots of the transgenic plants were also enclosed in the assay to assess the tissue specificity of the promoter. The GUS substrate was infiltrated into the tissues by mild vacuum and the tissues were incubated at 37° C. overnight. After the incubation, the tissue pieces were fixed, bleached and observed under stereomicroscope.

For fluorometric GUS assay, twenty developing seeds at 20 DAF from 4 selected transgenic plants, as well as from 2 control plants transformed by pUI121, were pooled and used for the quantitative analysis of GUS activity. Seeds were ground in 3 ml of extraction buffer, after grinding, the volume of the extract was increased to 12 ml, which was then centrifuged at 12000 g at 4° C. for 30 min. Collected supernatant was extracted with 2 volumes of hexane to facilitate Bradford protein assay. 2 ul of the aqueous fraction was used in the assay of GUS activity, Expression of LuFad3 in Yeast The open reading frame of LuFad3 was amplified by PCR using the Precision Plus enzyme (Stratagene) and cloned into a TA cloning vector (pCR® 2.1, Invitrogen). Having confirmed that the PCR products were identical to the original cDNAs by sequencing, the fragments were then released by a BamHI-EcoRI double digestion and inserted into the yeast expression vector pYES2 (Invitrogen) under the control of the inducible promoter GAL1.

Yeast strain InvSc2 (Invitrogen) was transformed with the expression constructs using the lithium acetate method and transformants were selected on minimal medium plates lacking uracil. Transformants were first grown in minimal medium lacking uracil and containing glucose at 28° C. After overnight culture, the cells were centrifuged, washed and resuspended in distilled water. Minimal medium containing 2% galactose, with or without 0.3 mM substrate fatty acids in the presence of 0.1% tergitol, was inoculated with the yeast transformant cell suspension and incubated at 20° C. for three days, and then 15° C. for another three days.

GC Analysis of Fatty Acid

Yeast cell culture was centrifuged at 1000×g and cell pellets were dried for 2 min by placing the glass tubes up side down on the paper towels. 2 ml of 3N methanolic HCl were added into the pellets and the tubes were capped properly and incubated at 80° C. for 1 hr. After cooling down, 0.5 ml of sterile water and 200 μL of hexane were added into the tube and mixed well. The hexane layer was separated by centrifugation at 4000×g for 10 min and transferred to a screw-capped GC vial for fatty acid analysis.

Example I

Isolation and Analysis of Conlinin Genes and Promoters

Identification of Flax Conlinin Genes

According to the hybridization patterns, the preferentially expressed cDNAs in the developing seeds were divided into three groups. The first group of clones had similarity to 2S storage proteins from other plant species, the second group to 12S storage proteins, and the third group consisted of cDNAs that did not hybridize to either group.

One clone (Conlinin 1) from the first group was selected for further analysis. It is 673 bp long (FIG. 1, SEQ ID NO:1) coding for a 168 amino acids FIG. 2, SEQ ID NO:2) with molecular weight 19 kd and isoelectric point at 7.5. Another cDNA clone from the same group (Conlinin 2), encoded by another member of the gene family was also identified. It is 676 bp in length (FIG. 3, SEQ ID NO: 3) and codes for 169 amino acids (FIG. 4, SEQ ID NO:4). The difference in nucleotide sequences between Conlinin 1 and Conlinin 2 is relatively small, with 43 point mutations and one 3 base deletion within the predicted open reading frame of Conlinin 1, as shown in a comparison of the proteins (FIG. 5). Additional differences are present in the 5' and 3, untranslated regions. The difference in protein sequence is Less, with an amino acid identity between the two sequences of 88%. Conlinin 1 protein is one amino acid residue shorter than Conlinin 2 protein (168 vis 169 AA). The positions of cysteine and most of glutamine residues, typical for 2S albumins, are all conserved between the two proteins, as shown in FIG. 6.

The deduced conlinin proteins do not posses a significant homology to the sequences in databases when analyzed by blastx blastp searches. However, short stretches surrounding cysteine residues were found conserved with 2S storage proteins from other plant species, such as *Ricinus communis, Arabidopsis thaliana, Gossypium hirsutum, Helianthus annum*. Homology was also observed in the putative signal peptide region (FIG. 7).

In flax, there is no molecular sequence information available about seed storage proteins. The published data on flax storage protein linin (12S) and conlinin (2S) are limited to biochemical analysis of the protein size and amino acid contents. Analysis of the putative protein revealed that amino acid content and size of the protein (after the cleavage of putative signal peptide) encoded by the clone Conlinin 1 is very close to that of the flax conlinin published previously, as shown in Table 1. Considering that biochemical analysis of amino acids reflects the mixture of proteins encoded by possible different members of the gene family, Conlinin 1 is a member of the gene family coding for a conlinin storage protein in flax.

TABLE 1

Comparison of CONLININ previously reported and CONLININ encoded by Conlinin cDNAs.

| | Literature | | Putative proteins | |
|---|---|---|---|---|
| | Madhusudhan and Singh | Youle and Huang | (After cleavage of putative signal peptide) | |
| | (1985) | (1981) | CONLININ 2 | CONLININ 1 |
| | | | Size | |
| | 1.6 S | 2.0 S | 169 a.a. | 168 a.a. |
| | | | Mol. weight | |
| | 15000-17000 | NA | 16769 | 16718 |
| | [mol. %] | [mol. %] | [mol. %] | [mol. %] |
| Ala | 1.9 | 5.1 | 2.7 | 2.7 |
| Asx | 13.1 | 6.0 | 5.4 | 6.8 |
| Cys | 3.5 | 8.2 | 5.4 | 5.5 |
| Glx | 35.0 | 23.8 | 29.9 | 30.1 |
| Phe | 2.4 | 2.2 | 3.4 | 2.1 |
| Gly | 8.3 | 13.8 | 12.9 | 12.3 |
| His | 1.6 | 1.2 | 0.7 | 0.7 |
| Ile | 2.8 | 2.9 | 4.8 | 3.4 |
| Lys | 4.9 | 6.0 | 2.7 | 3.4 |
| Leu | 5.4 | 5.3 | 3.4 | 4.8 |
| Met | 0.8 | 1.9 | 1.4 | 0.7 |
| Pro | 3.0 | 1.6 | 1.4 | 1.4 |
| Arg | 13.1 | 6.0 | 7.5 | 8.2 |
| Ser | 3.9 | 6.1 | 6.1 | 5.5 |
| Thr | 2.1 | 3.6 | 4.1 | 3.4 |
| Val | 2.6 | 3.9 | 2.7 | 4.1 |
| Trp | 2.0 | 0.8 | 2.0 | 2.0 |
| Tyr | 1.4 | 1.5 | 2.0 | 2.7 |

Identification of Flax Conlinin Promoters

Eight independent lambda clones were isolated from the flax genomic library that hybridised with the Conlinin 1 cDNA. Two clones were sequenced using the internal primers of the cDNA. In the upstream region of the predicted start codon, several cis-elements previously identified as crucial for seed-specific expression of napin A gene were found in Conlinin 1 promoter (FIG. 8, SEQ ID NO:5). Like the napin promoter, The Conlinin 1 promoter consists of symmetrical arrangement of RY elements with the G-box in the middle (CATGCATTATTACACGTGATCGC CATGCA). This arrangement is also seen in A. thaliana 2S protein gene (At2S). The position and sequence of the G-box and the 3' RY element of Conlinin 1 Promoter are identical to that of the At2S1 promoter. In the upstream of the G-box (23 bp), however, another copy of slightly modified G-box (CTACGTG) and RY-elements (CATGAA) was also found in ConlininPromoter 1. This organisation of cis-elements, although with larger mutual distances, is also present in the second conlinin promoter, Conlinin 2 promoter (FIG. 9, SEQ ID NO:6).

Northern Blot Analysis of the Conlinin cDNA

Figure 11:
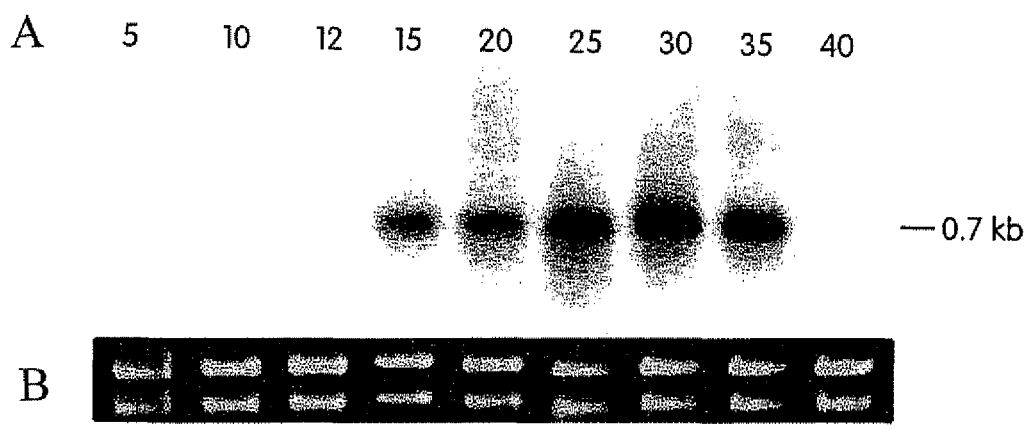
FIG. 11 depicts the temporal expression of Conlinin. A shows a northern blot hybridization with the Conlinin 1 probe. B shows an ethidium bromide gel indicating RNA loading. The total RNA was isolated from developing seeds at different stages (5-40 days after flowering)

Preliminary dot expression analysis showed Conlinin 1 was preferentially expressed in developing seeds, and not in seedling tissues. To precisely define the expression pattern, two northern blots containing total RNA isolated from hypocotyls, leaves, roots, stem, flower buds as well as developing embryo from different stages were hybridized with the Conlinin 1 probe. The results indicated that a single strong band was only detected in developing seeds, not in any other tissues analyzed even after a prolonged exposure (FIG. 10). In developing seeds, the hybridization signal was first detected at about 10 DAF (days after flowering), after then the expression is gradually increased, and it reaches the maximal level at 25-30 DAF FIG. 11).

Conlinin Promoter Activity in Flax

Figure 24:
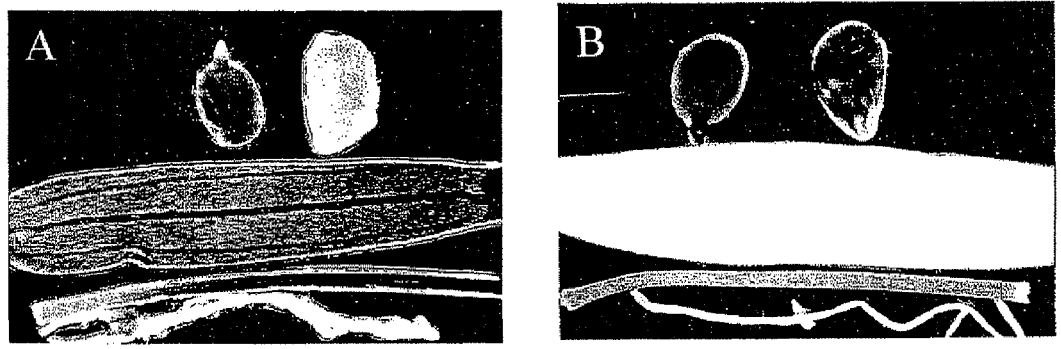
FIG. 24 depicts a flax promoter activity in flax. A shows tissue specificity and pattern of GUS expression under the control of CaMV 35S promoter. B shows tissue specificity and pattern of GUS expression under the control of the flax Conlinin promoter. Materials: embryo and seed coat dissected from the developing seed at 20 days after flowering, leaf, stem and root.

Agrobacterium carrying the construct containing the Conlinin 1 promoter and GUS fusion were used in transformation of flax hypocotyls (var. CDC Normandy). More than 10 transgenic plants were obtained. Upon flowering, individual flower of the transgenic plants was labeled. The developing seeds of both plants transformed with Conlinin 1 promoter and 35S promoters were stained for GUS activity. Results indicated that only developing seeds, not other tissues such as leaves, stems and roots from Conlinin 1 promoter transgenics, possess GUS activities (FIG. 24). In the seed, GUS gene was expressed throughout the embryo, but high activity was also observed in the inner cell layers of the seed coat. Whereas, CaMV 35S promoter is active in cotyledons, leaves, stem, but no activity was observed in the root and the seed coat (FIG. 24).

The conlinin promoter activity in the inner cell layers of seed coats was segregating together with the activity in the embryo. Therefore, the inner cell layers of seed coats where the promoter is activated might be residue left from endosperm cells. Within the embryo, blue staining had higher intensity in the embryo axis than in the cotyledons. This, however, could be caused by easier access of the enzymatic substrate and more intensive staining of vascular tissue as observed previously in other species.

Figure 12:
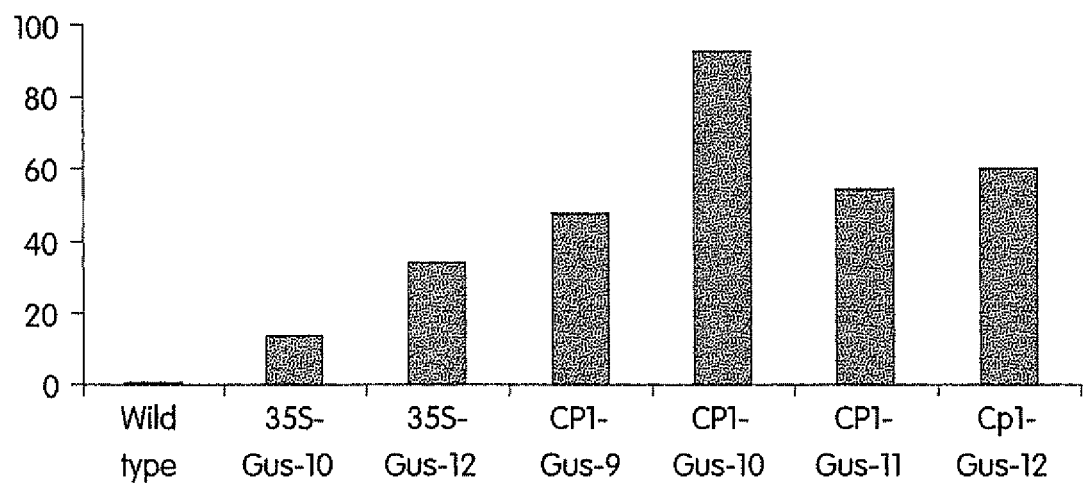
FIG. 12 depicts a quantitative assay of GUS activity of transgenic developing seeds. GUS activity was measured as pmol 4-MU/min/μg protein.

Quantitative fluorimetric GUS assays were cared out in four transgenic flax plants. They were pre-selected based on the segregation patterns and their single copy status which was confirmed by Southern analysis. GUS gene driven by the conlinin promoter constantly showed specific expression in developing seeds (FIG. 12). Compared to single copy 35S-GUS transgenic plants, the flax conlinin promoter transgenics possess considerably higher GUS activity in the developing embryo at 20 DAF.

Figure 13:
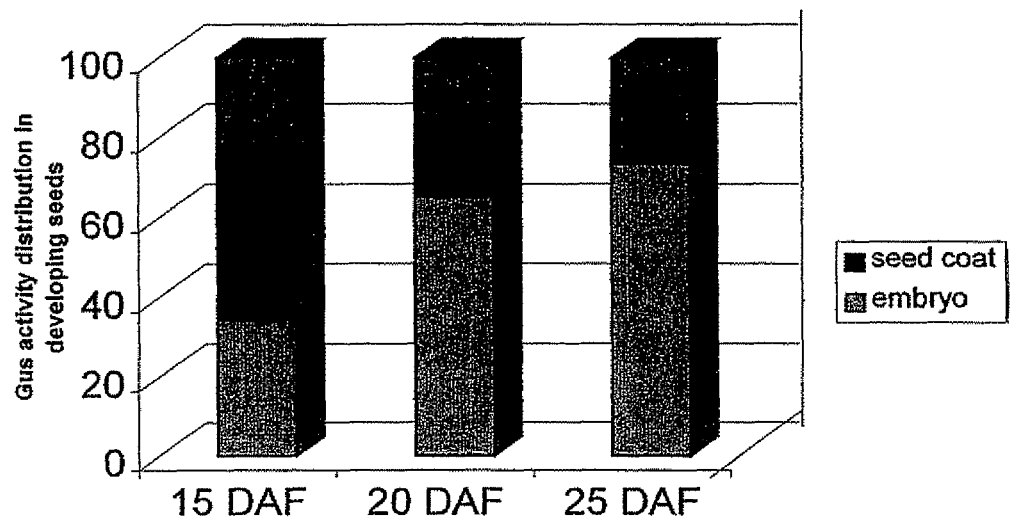
FIG. 13 depicts the distribution of GUS activity between the embryo and the seed coat at three different developmental stages. Seed coats were removed from embryos and analyzed separately. The relative contribution to overall GUS activity is expressed as percentage of the total MU produced in both reactions

To establish the contribution rate of the GUS activity in the inner layer of the seed coat to the overall seed expression, isolated embryo and seed coats at 15, 20 and 25 DAF of one transgene line were analyzed. The results showed that the seed coat constitutes rather considerable portion of the total seed GUS activity at 15 DAF (66.5%), but its share is diminishing as the embryo increases with the age—34.9% at 20 and 26.6% at 25 DAF (FIG. 13). As for the promoter activity within the embryo itself, the analysis of the developing seeds at the age of 20 DAF showed that cotyledons without the axis posses only 34.2% of the total activity in the embryo compared to 65.8% in embryo axis. This result is in agreement with stronger histochemical staining in the embryo axis. Similar pattern of expression with relatively higher activity in embryo axis and lower in the cotyledons was also observed for the At2S1 gene of A. thaliana.

Conlinin Promoter Activity in Arabidopsis thaliana

To examine the promoter activity in heterologous plant systems, Arabidopsis thaliana was transformed with the construct containing Conlinin 1 promoter and GUS fusion by dip-vacuum infiltration of the inflorescence, which resulted in hundreds of putative transgenic seeds. Siliques of infiltrated plants carrying developing Ti seeds in various stages of development were stained for GUS activity and several embryos at the late heart stage to the torpedo stage were found positive in blue staining (FIG. 25). These were individual transformation events as they were the only seeds with blue staining embryo in their siliques. This result indicates that the flax Conlinin 1 promoter is specifically activated in the developing seeds of Arabidopsis thaliana as in its host plants. However, slight difference in the expression pattern was observed. In Arabidopsis thaliana the GUS activity was restricted to the embryo and the activity was not detected in the seed coat.

Example II

Isolation and Analysis of LuFad3 Gene and Promoter

Identification of LuFad3 cDNA in Flax

To isolate LuFad3 cDNA from flax, two degenerate primers that target the first and third histidine-rich motifs were utilized to RT-PCR the fragment by using the total RNA from the developing seeds as the template. Sequence analysis of amplified fragments revealed that one clone has high sequence similarly to ω-3 desaturases from other plant species. A blastn search of Lufad3 MONA revealed an approximate 60% identity to other ω-3 desaturases along the whole sequence. A blastp search using the LuFad3 protein sequence revealed an approximate 69% amino acid identity ti ω-3 desaturases in the database. The fill-length cDNA clone was then isolated by using the insert as probes to screen a developing seed cDNA library. The full-length cDNA is 1475 bp long (FIG. 14, SEQ ID NO:7) and contains an open reading frame of 1179 bp 2 encoding 392 amino acid with the molecular mass of 43 kd and the isoelectric point of 9.0 (FIG. 15, SEQ ID NO:8). The deduced protein contains almost 50% of hydrophobic amino acids, reflecting its membrane-associated property.

Functional Expression of the cDNA Gene in Yeast

Figure 16:
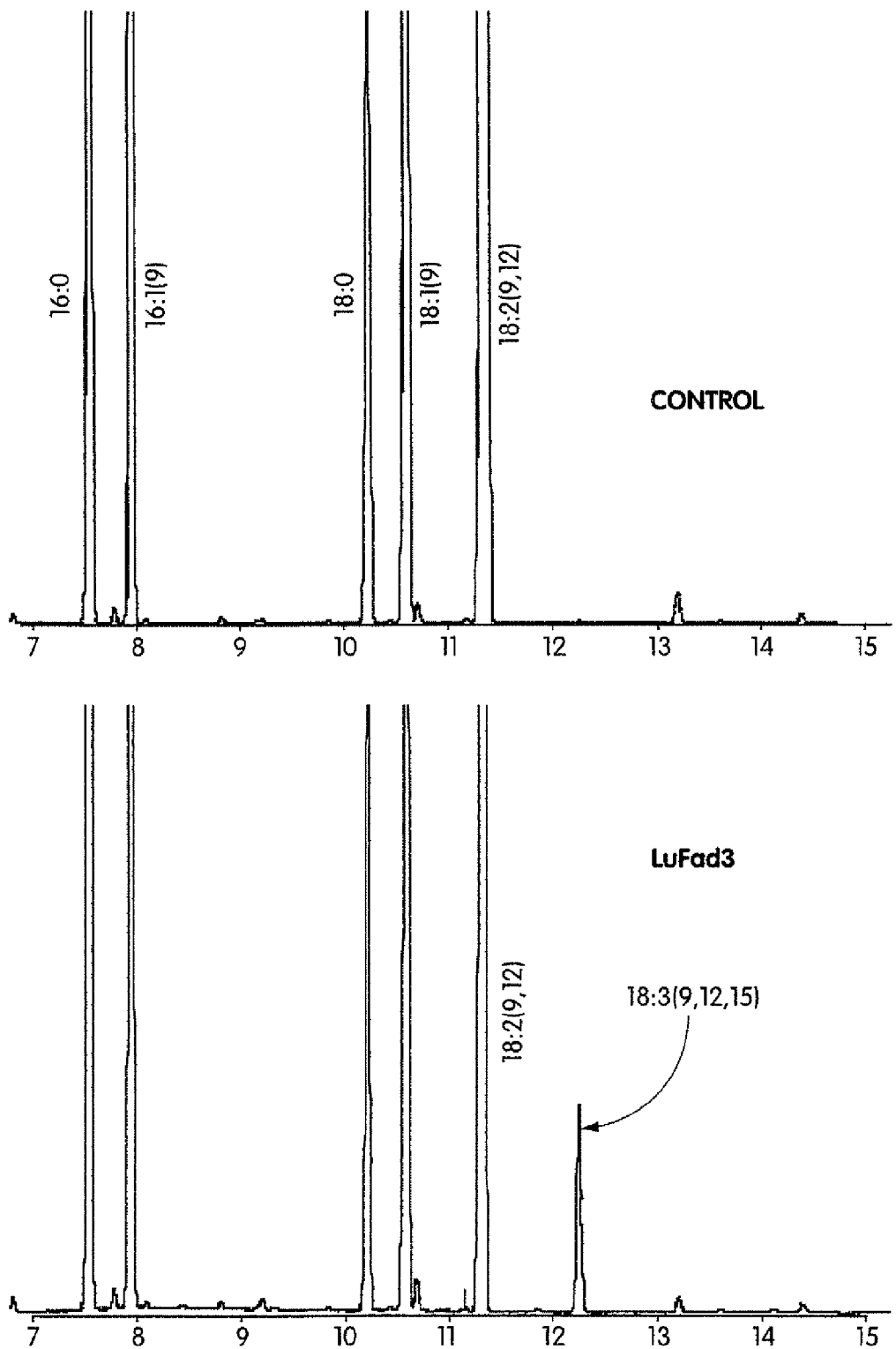
FIG. 16 shows a gas-chromatographic analysis of FAMEs (fatty acid methyl esters) isolated from yeast transformed with the control plasmid and with the plasmid which contains the full-length LuFad3 and grown in the presence of exogenous linoteic acid (18:2-9, 12).

To examine the functionality of the sequence, the full-length cDNA was then put into a yeast expression vector under control of a galactose-inducing promoter. The yeast host cells harboring the construct were fed with the substrate of ω-3 desaturase (linoleic acid). GC analysis revealed a new fatty acid in yeast cells containing the putative ω-3 desaturase, while the control cells containing the vector without the insert did not produce this novel fatty acid (FIG. 16).

Figure 17:
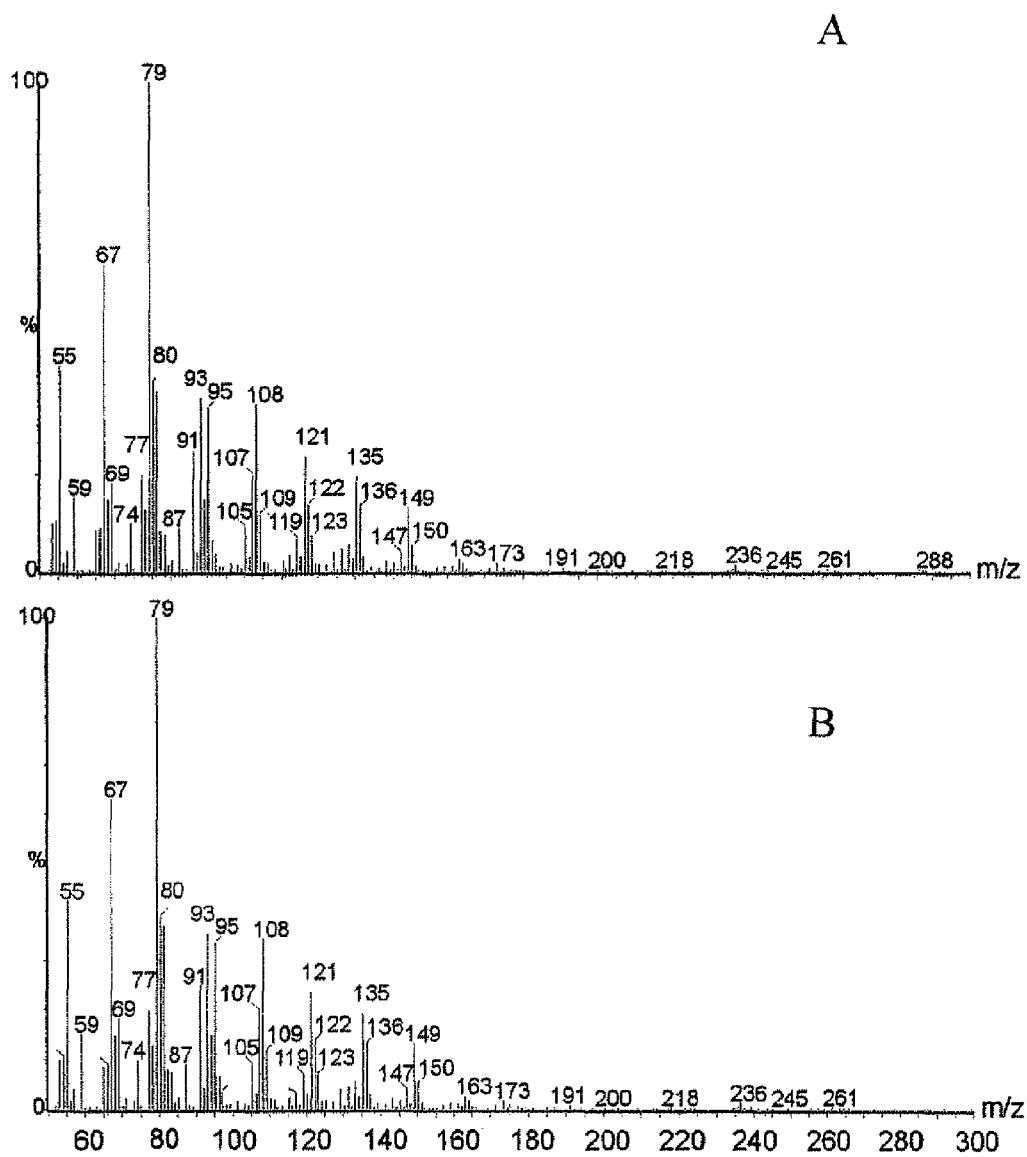
FIG. 17 depicts a GC/MS analysis of FAMEs of the new peak in FIG. 16. A, the LuFad3 product B, α-linolenic acid methyl ester standard (18:3-9, 12,15).

There are two lines of evidences indicating the new fatty acid produced in transgenic yeast is α-linolenic acid. First, gas chromatography analysis showed the retention time of the new fatty acid identical to that of α-linolenic acid standard. Second, GC/MS analysis of the fatty acid methyl ester indicated that spectra of both standard α-linolenic acid and new fatty acid are identical (FIG. 17). Taken together, LuFAD3 isolated from flax developing seeds is indeed a ω-3 desaturase that can introduce a double at position 15 of linoleic acid.

Northern Blot Analysis of LuFad3

Figure 18:
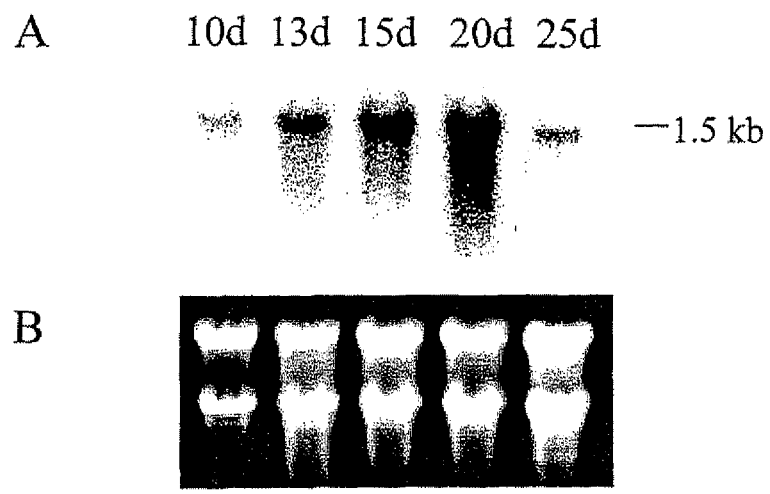
FIG. 18 shows a temporal expression of LuFad3 in flax developing seeds. A depicts a Northern blot hybridization with LuFad3 cDNA probe. B depicts an ethidium bromide gel indicating RNA loading. The total RNA was isolated from developing seeds at different stages (10-25 days after flowering).

Northern blot analysis of the developing seeds of Normandy at different days after flowering revealed the LuFad3 starts its expression at about 10 DAF, gradually increased its expression with the development of embryo, reached a maximum expression at around 20 DAF and after then, its expression was dramatically reduced (FIG. 18).

Figure 19:
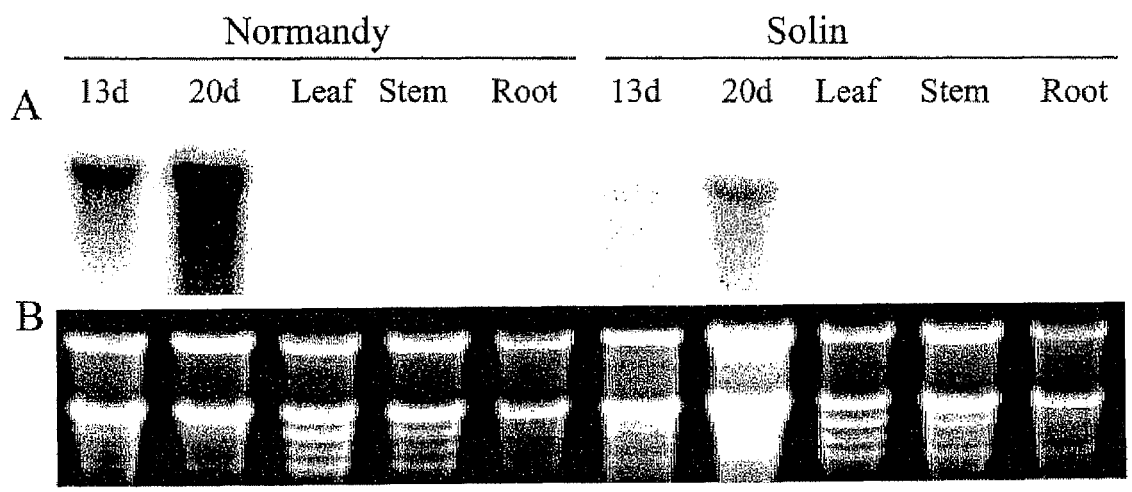
FIG. 19 depicts a Northern blot analysis of LuFad3 in flax. A shows a Northern blot hybridization with the LuFad3 probe. B shows an ethidium bromide gel indicating RNA loading. The total RNA was isolated from leaf, stem, root and developing seed at 20 DAF.

To examine the expression of the gene, another northern blot containing total RNA isolated from leaves, stems, roots and developing seeds was prepared and probed with the cDNA. The result showed that LuFad3 was only expressed in developing seeds, not in other tissues examined (FIG. 19).

Southern Analysis of the Gene

To examine the copy number of the gene in the genomes, two southern blots were prepared from genomic DNAs isolated from Normandy and Solin (flax) and digested with EcoRI and BamH. The blots were then probed with the promoter and 5'coding regions of LuFad3, respectively. Both EcoRI and BamHI do not have the cutting site in the promoter region, but EcoRI has two, BamHI has one cutting site located in the fourth intron, which is covered by the 5' coding region probe.

Figure 20:
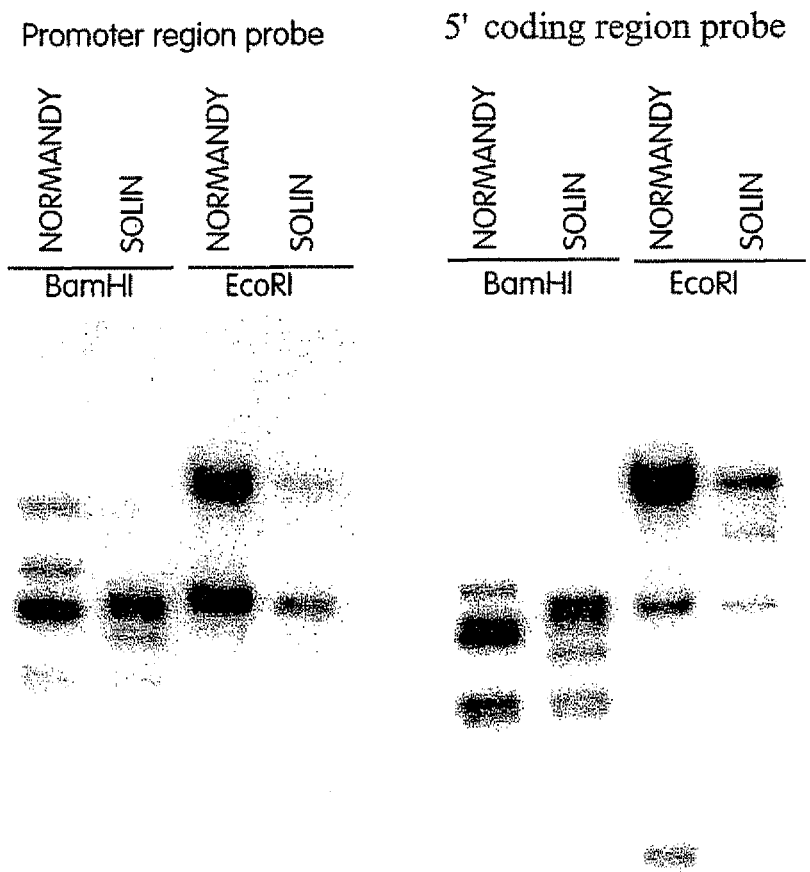
FIG. 20 depicts a Southern blot analysis of LuFad3 in flax. Genomic DNA was isolated from Normandy and Solin, digested with BamHI and EcoRI and probed with the LuFad3 promoter and coding regions, respectively.

Southern blot hybridization restricted with BamHI gave complex patterns—major bands mixed and surrounded with minors bands, which is not easy to interpret. However, southern blot hybridization restricted with EcoRI provided interpretable data. The 5' coding region probing gave four bands, the promoter region probing gave two bands with the same size in both genomes, indicating that both genomes contain two copies of the LuFad3 gene (FIG. 20). This conclusion is concomitant with a previous genetic study, which suggested that there are two loci in flax controlling the low linolenic trait.

Identification of the LuFad3 Promoter in Flax

To identify the genomic clones of the gene, a genomic library of Normandy was screened by LuFad3 cDNA probes. Comparison of genomic and cDNA sequences revealed five introns in the genomic sequences.

The promoter region of the gene was then identified from the upstream of the cDNA sequence (FIG. 21, SEQ ID NO:9). Sequence analysis of the promoter region did not reveal any significant homology to other seed-specific promoters. A blastn search using the Lufad3 promoter sequence did not reveal any significant homology, <(10%). The promoter region of the LuFad3 gene from Solin is shown in FIG. 22 (SEQ ID NO:10).

The Promoter Activity in Flax

Figure 27:
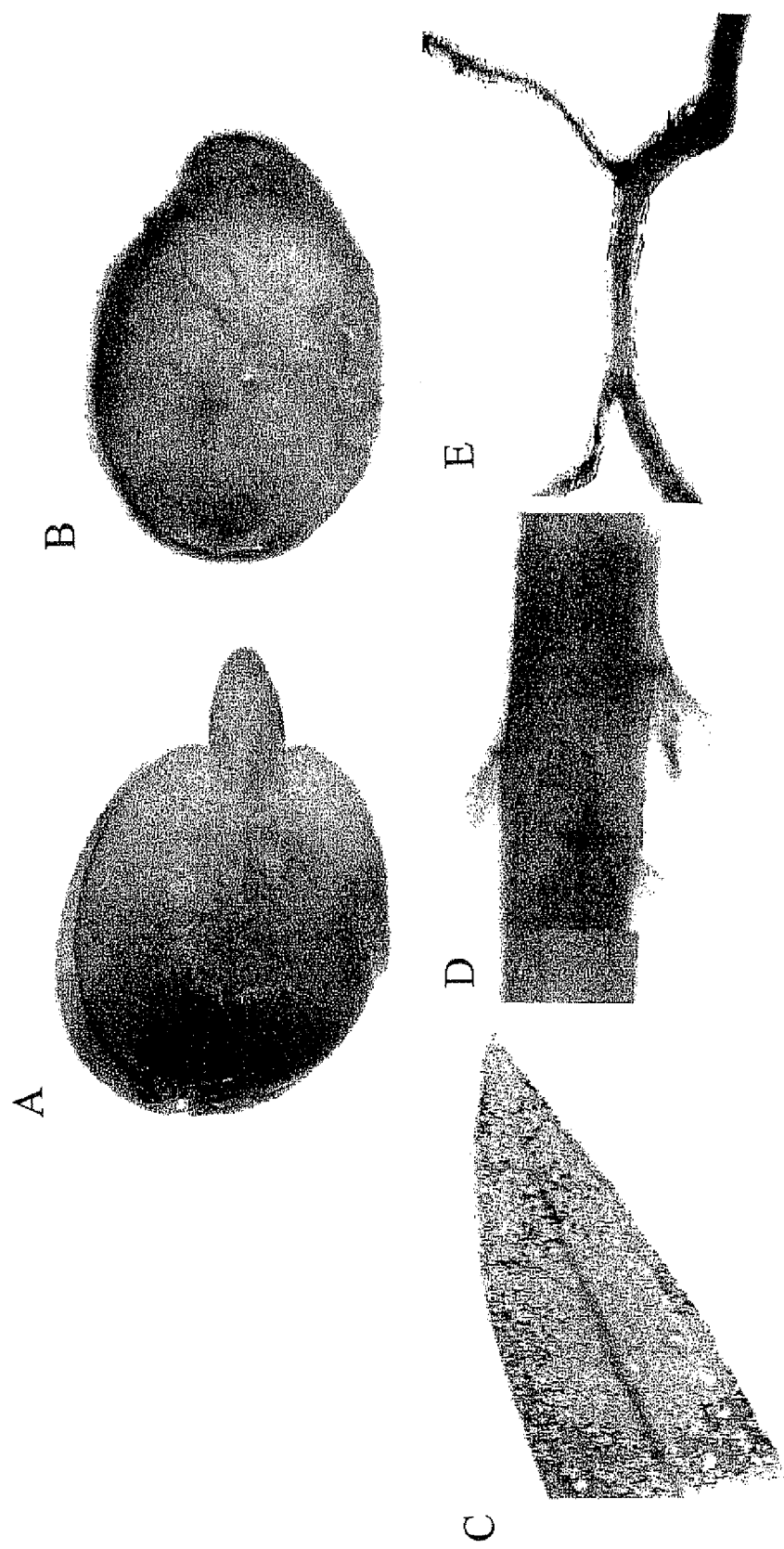
FIG. 27 depicts tissue-specific activity of the LuFad3 promoter in flax (GUS staining). A shows an embryo at 15 days after flowering; B: seed coat; C: Leaf; D: stem; E: root.
Figure 28:
FIG. 28 depicts the 35S promoter activity in flax (GUS staining). A shows an embryo at 15 days after flowering; B: seed coat; C: Leaf; D: stem; E: root.

Agrobacterium carrying the construct containing the LuFad3or 35S promoter with GUS fusion were used in transformation of flax hypocotyls (var. CDC Normandy). More than 10 transgenic plants were obtained. Upon flowering, individual flower of the transgenic plants were labeled. The developing seeds of both plants transformed with the LuFad3promoter and 35S promoters were stained for GUS activity. Results indicate that only developing embryo, not other tissues such as seed coats, leaves, stems and roots as, from the LuFad3promoter transgenics, possess GUS activities (FIG. 26 and FIG. 27). Whereas, CaMV 35S promoter is active in embryo, leaves and stems (FIG. 28). These results are consistent with that of northern blot hybridization, indicating the LuFad3promoter is specifically expressed in developing embryo of flax.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising a *Linum* LuFad3 promoter operably linked to a heterologous gene of interest, wherein said *Linum* LuFad3 promoter comprises:
   a) the nucleotide sequence of SEQ ID NO: 9 or 10, or
   b) a fragment of the nucleotide sequence of SEQ ID NO: 9 or 10, wherein said fragment is capable of directing seed-specific expression of said heterologous gene of interest in a plant.

2. A vector comprising the isolated nucleic acid molecule of claim 1.

3. An isolated nucleic acid molecule comprising a seed-specific promoter operably linked to a heterologous nucleic acid, wherein said seed-specific promoter comprises:
   a) a nucleic acid comprising the nucleotide sequence of SEQ ID NO: 9 or 10;
   b) a nucleic acid comprising a nucleotide sequence that is complimentary to the nucleotide sequence of SEQ ID NO: 9 or 10: or
   c) a fragment of a nucleic acid comprising the nucleotide sequence of SEQ ID NO: 9 or 10, wherein the fragment is capable of directing seed-specific expression of said heterologous nucleic acid in a plant.

4. A method for expressing a gene of interest in flax seeds comprising:
   a) preparing a nucleic acid construct comprising the isolated nucleic acid molecule of claim 1:
   b) introducing said nucleic acid construct into a flax plant cell; and
   c) growing said flax plant cell into a mature plant capable of setting seeds, wherein the gene of interest is expressed in the seeds under the control of said *Linum* LuFad3 promoter.

5. A transgenic flax plant prepared by the method of claim 4.

6. A transgenic seed having a transgene integrated into the genome of the seed, wherein the transgene comprises the isolated nucleic acid molecule of claim 1, and wherein the gene of interest confers a detectable and functional phenotype on the seed when expressed.

7. A nucleic acid molecule comprising a promoter isolated from *Linum* operatively linked to a heterologous gene related to fatty acid biosynthesis or lipid biosynthesis, wherein the promoter is capable of directing gene expression in developing flax seeds and comprises:
   a) the nucleotide sequence of SEQ ID NO: 9 or 10;or
   b) a fragment of the nucleotide sequence of SEQ ID NO: 9 or 10, wherein the fragment is capable of directing gene expression in developing flax seeds.

8. The nucleic acid molecule of claim 7, wherein the heterologous gene is selected from the group consisting of a conjugase Δ4 desaturase, Δ5 desaturase, and Δ6 desaturase.

9. A vector comprising the isolated nucleic acid molecule of claim 3.

10. The vector of claim 9, wherein the heterologous nucleic acid comprises a gene associated with fatty acid biosynthesis or lipid biosynthesis.

11. The vector of claim 10, wherein the gene associated with fatty acid biosynthesis or lipid biosynthesis is selected from the group consisting of conjugases, Δ4 desaturases, Δ5 desaturases, and Δ6 desaturases.

12. A transgenic plant, plant cell or a microorganism comprising the isolated nucleic acid molecule of claim 3.

13. The transgenic plant, plant cell or the microorganism of claim 12, wherein the heterologous nucleic acid comprises a gene associated with fatty acid biosynthesis or lipid biosynthesis.

14. The transgenic plant, plant cell or the microorganism of claim 13, wherein the gene associated with fatty acid biosynthesis or lipid biosynthesis is selected from the group consisting of conjugases, Δ4 desaturases, Δ5 desaturases, and Δ6 desaturases.

15. A method for producing a transgenic plant or plant cell, comprising transforming a plant cell with the vector of claim 9.

16. A method for producing a transgenic plant or plant cell, comprising transforming a plant cell with the vector of claim 10.

17. A method for producing a transgenic plant or plant cell comprising transforming a plant cell with the vector of claim 11.

18. A method for expressing a gene of interest in a plant or plant cell, comprising:
   a) preparing a nucleic acid construct comprising the isolated nucleic acid molecule of claim 3;
   b) introducing said nucleic acid construct into a plant or plant cell; and
   c) growing said plant or plant cell into a mature plant capable of setting seeds, wherein the nucleic acid is expressed in the seeds under the control of said seed-specific promoter.

* * * * *

SEQUENCE LISTING

<160> NUMBER OF SEQ ID NOS: 13

<210> SEQ ID NO 1
<211> LENGTH: 673
<212> TYPE: DNA
<213> ORGANISM: Linum usitatissimum

<400> SEQUENCE: 1

```
gaaaaaccaa tcataaccaa aatggcaaag ctgatgagcc tagcagccgt agcaacggca      60
ttcctcttcc tcattgtggt ggacgcatcc gtccgaacca cagtgatcat cgacgaggac     120
accaaccaag gccgcggtgg ccaaggtggg caaggacagc agcagcaatg cgagaagcag     180
atccaggagc aagactacct gaggagctgc agcagttcc tgtgggagaa agtccagaag      240
ggcggccgca gctactacta caaccaaggc cgtggaggag gcaacagag ccagcacttc      300
gatagctgct gcgatgatct taagcaattg aggagcgagt gcacatgcag gggactggag     360
cgtgcaatcg gccagatgag gcaggacatc agcagcagg acagcagca ggaagttgag       420
aggtgggtcc agcaagctaa acaagtcgct agggaccttc cgggacagtg cggcacccag     480
cctagccgat gccagctcca ggggcagcag cagtctgcat ggttttgaag tggtgatcga     540
tgagatcgta taaagacact tgctaggtgt taaggatggg ataataagat gtgttttaag     600
tcattaaccc gtaattaaaa ggagagagag cttgatggaa tggtattgat gttccttggg     660
ttttaaaaaa aaa                                                        673
```

<210> SEQ ID NO 2
<211> LENGTH: 168
<212> TYPE: PRT
<213> ORGANISM: Linum usitatissimum

<400> SEQUENCE: 2

```
Met Ala Lys Leu Met Ser Leu Ala Ala Val Ala Thr Ala Phe Leu Phe
 1               5                  10                  15
Leu Ile Val Val Asp Ala Ser Val Arg Thr Thr Val Ile Ile Asp Glu
                20                  25                  30
Asp Thr Asn Gln Gly Arg Gly Gly Gln Gly Gly Gln Gly Gln Gln Gln
            35                  40                  45
Gln Cys Glu Lys Gln Ile Gln Glu Gln Asp Tyr Leu Arg Ser Cys Gln
        50                  55                  60
Gln Phe Leu Trp Glu Lys Val Gln Lys Gly Gly Arg Ser Tyr Tyr Tyr
    65                  70                  75                  80
Asn Gln Gly Arg Gly Gly Gly Gln Gln Ser Gln His Phe Asp Ser Cys
                85                  90                  95
Cys Asp Asp Leu Lys Gln Leu Arg Ser Glu Cys Thr Cys Arg Gly Leu
               100                 105                 110
Glu Arg Ala Ile Gly Gln Met Arg Gln Asp Ile Gln Gln Gln Gly Gln
           115                 120                 125
Gln Gln Glu Val Glu Arg Trp Val Gln Ala Lys Gln Val Ala Arg
       130                 135                 140
Asp Leu Pro Gly Gln Cys Gly Thr Gln Pro Ser Arg Cys Gln Leu Gln
145                 150                 155                 160
Gly Gln Gln Gln Ser Ala Trp Phe
                165
```

<210> SEQ ID NO 3
<211> LENGTH: 676
<212> TYPE: DNA
<213> ORGANISM: Linum usitatissimum

<400> SEQUENCE: 3

```
aagaaccaat caccaccaaa aaatggcaaa gctgatgagc ctggcagccg tagcaacggc      60
attcctcttc ctgatcgtgg tggacgcatc cgtccgaacc acagtgatta tcgacgagga    120
```

```
gaccaaccaa ggccgcggtg gaggccaagg tggccaggga cagcagcagt cttgcgagca      180
gcagatccag cagcaagact tcctgaggag ctgccagcag ttcatgtggg agaaagtcca      240
gaggggcggc cgcagccact attacaacca gggccgtgga ggaggcgaac agagccagta      300
cttcgacagc tgttgtgacg accttaagca attgagcacc gggtgcacat gcaggggact      360
tgagcgtgcc atcggccaaa tgaggcagga aatccagcag cagggacagc agcaggaagt      420
tcagaggtgg atccagcaag ctaaacaaat cgctaaggac ctccccggac agtgccgacc      480
cagcctagcc aatgccagtt ccagggccag cagcaatctg catggttttg aagggtgat      540 cgattatgag atcgtacaaa gacactgcta ggtgttaagg atggataata ataataataa      600
tgagatggat gtgttttaag ttaatgtaac agcttaataa agagagagag agagagagag      660
agagagagtc aaaaaa                                                     676

<210> SEQ ID NO 4
<211> LENGTH: 169
<212> TYPE: PRT
<213> ORGANISM: Linum usitatissimum

<400> SEQUENCE: 4

Met Ala Lys Leu Met Ser Leu Ala Ala Val Ala Thr Ala Phe Leu Phe
  1               5                  10                  15

Leu Ile Val Val Asp Ala Ser Val Arg Thr Thr Val Ile Ile Asp Glu
             20                  25                  30

Glu Thr Asn Gln Gly Arg Gly Gly Gln Gly Gly Gln Gly Gln Gln
         35                  40                  45

Gln Ser Cys Glu Gln Gln Ile Gln Gln Gln Asp Phe Leu Arg Ser Cys
     50                  55                  60

Gln Gln Phe Met Trp Glu Lys Val Gln Arg Gly Gly Arg Ser His Tyr
 65                  70                  75                  80

Tyr Asn Gln Gly Arg Gly Gly Gly Glu Gln Ser Gln Tyr Phe Asp Ser
                 85                  90                  95

Cys Cys Asp Asp Leu Lys Gln Leu Ser Thr Gly Cys Thr Cys Arg Gly
            100                 105                 110

Leu Glu Arg Ala Ile Gly Gln Met Arg Gln Glu Ile Gln Gln Gln Gly
        115                 120                 125

Gln Gln Gln Glu Val Gln Arg Trp Ile Gln Gln Ala Lys Gln Ile Ala
    130                 135                 140

Lys Asp Leu Pro Gly Gln Cys Arg Thr Gln Pro Ser Gln Cys Gln Phe
145                 150                 155                 160

Gln Gly Gln Gln Gln Ser Ala Trp Phe
                165

<210> SEQ ID NO 5
<211> LENGTH: 1121
<212> TYPE: DNA
<213> ORGANISM: Linum usitatissimum

<400> SEQUENCE: 5
caacggttcc ggcggtatag agttgggtaa ttcgaaaccg cacagatcca attcgattag       60
cagatatttg gtgtctaaat gtttattttg tgatatgttc atgtttgaaa tggtggtttc      120
gaaaccaggg acaacgttgg gatctgatag ggtgtcaaag agtattatgg attgggacaa      180
tttcggtcat gagttgcaaa ttcaagtata tcgttcgatt atgaaaattt tcgaagaata      240
tcccatttga gagagtcttt acctcattaa tgttttagga ttatgaaatt ttatcatagt      300
```

```
tcatcgtagt cttttttggtg taaaggctgt aaaagaaat tgttcacttt tgttttcgtt      360
tatgtgaagg ctgtaaaaga ttgtaaaaga ctattttggt gttttggata aaatgatagt      420
ttttatagat tcttttgctt ttagaagaaa tacatttgaa attttttcca tgttgagtat      480
aaaataccga aatcgattga agatcataga aatattttaa ctgaaaacaa atttataact      540
gattcaattc tctccatttt tatacctatt taaccgtaat cgattctaat agatgatcga      600
ttttttatat aatcctaatt aaccaacggc atgtatggat aattaaccga tcaactctca      660 ccccctaatag aatcagtatt ttccttcgac gttaattgat cctacactat gtaggtcata      720
tccatcgttt taatttttgg ccaccattca attctgtctt gcctttaggg atgtgaatat      780
gaacggccaa ggtaagagaa taaaaataat ccaaattaaa gcaagagagg ccaagtaaga      840
taatccaaat gtacacttgt cattgccaaa attagtaaaa tactcggcat attgtattcc      900
cacacattat taaaataccg tatatgtatt ggctgcatt tgcatgaataa tactacgtgt       960 aagcccaaaa gaacccacgt gtagcccatg caaagttaac actcacgacc ccattcctca     1020
gtctccacta tataaaccca ccatccccaa tctcaccaaa cccaccacac aactcacaac     1080
tcactctcac accttaaaga accaatcacc accaaaaaat g                         1121

<210> SEQ ID NO 6
<211> LENGTH: 1017
<212> TYPE: DNA
<213> ORGANISM: Linum usitatissimum

<400> SEQUENCE: 6
aactgatata tattactttg ttggttggtt aatagattaa cctattttc ataaaattat        60 aattaataaa aaaattgagt ttttgaaatt ttgagctttc ttgtattatg ttggaacttc      120
ttgttccatt gcaataaaat cagttataaa aaaattacaa acgaagtgca ctcagtaatt      180
aaccacctca aacagactct cacttactca tagtaggatc aatattttcc ttcggcgata      240
atcgttcctc cactatgtag gtcattattt taattttggg tgatttatta tgtgtctaat      300
tttaaaaatt aattattcga taaatattac ttttatgtat tgttagtttg ttttggaatt      360
ttaaagtttg agttggtctt aagagttatc ttgtttaacc gatattaatt gtaatactag      420
aaaaataaag cttataaaaa acctttatt tgtacataga tagggaatc gaagaagaaa       480 aaaattcaaa gtttaaatta tttattttat atttatgtta tttactttaa attttctaat      540
ttctattaaa tattaatcat atacgtcaaa gcgtaatata atgggcacct tacacaaaca      600
ttcgatagaa gggatgtgaa tatgaaggga ccaaagtgag atcttgccct cagctcctag      660
tgcgcctctt gctgttgctc cacgtgttaa tccaagtggc gagaaaagga gaataataac      720
gcaaaaaaac aggccaagta agataatcca agtgtacact tgtcatcgcc aaacttacta      780
aaatacgcgg caaattgtat acccacacat tattaccata ccatatattg gctgcatttg      840
catgtataat actacgtgta agctcagaaa attccacgtg tcgcccatgc aaaattaaca      900
ctcacgaccc attcctaaat ctccactata taaacccccca ctccccccatc ttaccaaacc     960 caccacacaa ctcacaactt agaaaaacca atcataacca aaatggcaaa gctgatg        1017

<210> SEQ ID NO 7
<211> LENGTH: 1475
<212> TYPE: DNA
<213> ORGANISM: Linum usitatissimum
```

<400> SEQUENCE: 7

```
caaaaatata tattgggttt gtttggtgca gattacagtg acttcaaaac tgtggctctg      60
cacgaccaaa ctatgagccc tccaaactca atgagtcccg ccaccaacgg cagcaccaat     120
ggtgtggcta tcaatgggc gaagaagcta ctcgatttcg acccgagtgc tgctccccct     180
ttcaagattg cagacatccg tgctgcaatc ccgccgcatt gttgggtgaa gaaccctgg     240
aggtcactca gctacgtcct gagagacctc ctggtcatcc tcagcttcgc cgttgcggcg     300
acaaagctgg acagctggac tgtctggcct ctctactgga ttgctcaagg aaccatgttc     360
tgggcagtct tgttcttgg acatgattgt ggccatggga gcttctcaga cagttggttg     420
ttgaacaacg tgatgggaca tatactccat tcctcaatcc tcgtaccttac ccatggatgg     480
agaattagcc acaagaccca tcaccagaat cacggcaatg tggagaaaga tgaatcctgg     540
gttccactgc cggagaaggt gtacaagagc ttggataccg caccaagtt catgaggttc     600
accatccctc tcccaatgtt tgcgtatcct atctacttgt ggaggagaag tccggggaag     660
aaagggtcgc atttcaaccc atacagtgac ctgttcgcac cgaacgagag gacatcggtc     720
atgatttcga cattgtgctg gacagccatg gccttactcc tctgctactc atcgttcatc     780
tacggcttcc ttccggtctt caaaatctac ggcgtccctt atctaatatt cgtggcgtgg     840
ctcgacatgg tgacctacct tcaccaccac gggtacgagc agaagctgcc gtggtacaga     900
ggcaaagagt ggagctaccc acgtggaggg ctgacgaccg tcgatcgaga ttacggggtc     960
atcaacaaca tccaccatga cattggcacc catgttattc accatctctt ccctcaaatg    1020
ccacactatc acctagtcga agcgactcag gcagcgaagc acgtgctggg gaagtactac    1080
agagaaccga gaaatcagg gcctttccca ttccacttgt ttgggtactt ggtgaggagc    1140
ctgggcgagg atcactacgt tagcgataca ggcgacgtcg ttttctatca atctgacccca    1200
catattccca gttccctac cagtgccacc accaagtcca aatctagctg atgatattgg    1260
ctctgatctg atgtatgctg caggctgttt tattttgtcc tttgttcgtt tctttctgcc    1320
agaaacaaat tctctgtttc tatgtttctc tgtctctccc accccagctt tctttctgag    1380
tatatcgtat aaagtttcaa gtgattgtaa gagcagaaaa gaaagaaga agaagaataa    1440
taaagaggat tggcaacaaa aaaaaaaaaa aaaaa                                1475
```

<210> SEQ ID NO 8
<211> LENGTH: 392
<212> TYPE: PRT
<213> ORGANISM: Linum usitatissimum

<400> SEQUENCE: 8

```
Met Ser Pro Pro Asn Ser Met Ser Pro Ala Thr Asn Gly Ser Thr Asn
  1               5                  10                  15

Gly Val Ala Ile Asn Gly Ala Lys Lys Leu Leu Asp Phe Asp Pro Ser
             20                  25                  30

Ala Ala Pro Pro Phe Lys Ile Ala Asp Ile Arg Ala Ala Ile Pro Pro
         35                  40                  45

His Cys Trp Val Lys Asn Pro Trp Arg Ser Leu Ser Tyr Val Leu Arg
     50                  55                  60

Asp Leu Leu Val Ile Leu Ser Phe Ala Val Ala Ala Thr Lys Leu Asp
 65                  70                  75                  80

Ser Trp Thr Val Trp Pro Leu Tyr Trp Ile Ala Gln Gly Thr Met Phe
                 85                  90                  95
```

```
Trp Ala Val Phe Val Leu Gly His Asp Cys His Gly Ser Phe Ser
            100                 105                 110

Asp Ser Trp Leu Leu Asn Asn Val Met Gly His Ile Leu His Ser Ser
        115                 120                 125

Ile Leu Val Pro Tyr His Gly Trp Arg Ile Ser His Lys Thr His His
    130                 135                 140

Gln Asn His Gly Asn Val Glu Lys Asp Glu Ser Trp Val Pro Leu Pro
145                 150                 155                 160

Glu Lys Val Tyr Lys Ser Leu Asp Thr Gly Thr Lys Phe Met Arg Phe
                165                 170                 175

Thr Ile Pro Leu Pro Met Phe Ala Tyr Pro Ile Tyr Leu Trp Arg Arg
            180                 185                 190

Ser Pro Gly Lys Lys Gly Ser His Phe Asn Pro Tyr Ser Asp Leu Phe
        195                 200                 205

Ala Pro Asn Glu Arg Thr Ser Val Met Ile Ser Thr Leu Cys Trp Thr
    210                 215                 220

Ala Met Ala Leu Leu Cys Tyr Ser Ser Phe Ile Tyr Gly Phe Leu
225                 230                 235                 240

Pro Val Phe Lys Ile Tyr Gly Val Pro Tyr Leu Ile Phe Val Ala Trp
                245                 250                 255

Leu Asp Met Val Thr Tyr Leu His His His Gly Tyr Glu Gln Lys Leu
            260                 265                 270

Pro Trp Tyr Arg Gly Lys Glu Trp Ser Tyr Leu Arg Gly Gly Leu Thr
        275                 280                 285

Thr Val Asp Arg Asp Tyr Gly Val Ile Asn Asn Ile His His Asp Ile
    290                 295                 300

Gly Thr His Val Ile His His Leu Phe Pro Gln Met Pro His Tyr His
305                 310                 315                 320

Leu Val Glu Ala Thr Gln Ala Ala Lys His Val Leu Gly Lys Tyr Tyr
                325                 330                 335

Arg Glu Pro Lys Lys Ser Gly Pro Phe Pro Phe His Leu Phe Gly Tyr
            340                 345                 350

Leu Val Arg Ser Leu Gly Glu Asp His Tyr Val Ser Asp Thr Gly Asp
        355                 360                 365

Val Val Phe Tyr Gln Ser Asp Pro His Ile Pro Lys Phe Pro Thr Ser
    370                 375                 380

Ala Thr Thr Lys Ser Lys Ser Ser
385                 390

<210> SEQ ID NO 9
<211> LENGTH: 1107
<212> TYPE: DNA
<213> ORGANISM: Linum usitatissimum

<400> SEQUENCE: 9
actacctgca aaccaaaaca gattcatggc caagcttatt cccacaaaag ggtccaaaca    60
aaaggaaaat ggtctgattg tctgctaaag tttattgatc agtacgtggg tggatgtttt   120
gttcaccttt acagtgccat tctttaccac agttgttacc agcatcactc atcatcatca   180
gcatcattaa tccttagttt tctatgcact cactttcatt agtgttcact ttgcaattca   240
ataatccatc tattattcga ttgcaaagca agagagttgt aagagtttcg actaagttca   300
aatggagccc aaagtttgat catcagtttg tgaaaacaaa gtcaagctcg tccatatctc   360
tgccttgttc ccaaccccact acatagcatc tggaagacct cgtacttcac attctcggac   420
```

```
cgaaggacaa ccaatacccc ccttgtgatc ctaaacacat gcacaaatcc ctctgcccga      480
aacttgcccg aacttactcc ctaagaccga tgcccacttg agtcacatga gttgattagt      540
cgattccacc ctagctcccg cgaactcagc agtgcccgtt gcgactccgc caaatcacta      600
atccttaatt aaaagaacta ataagttgat atcatcacat ttgtggtaac tcatgcatgc      660
acataggttt cctagatacc attgaaggaa gttgccatgt gtttgaatca agatttgcc       720 caccaccatt gatactgaaa ttgaagaacc tagcagccag caacggctcc ttttcatttg      780
tctttcaaca gagcaagtaa caacaaccgt tgcctaaact gaaacccaat aaagagcaaa      840
aaaaaagggg ttgggtggtg taggctagtt tgtctgaaat cagtgtacat tttgcatttc      900
catttactct tctccatcca cttggcatcc tgcattactt cttcttcgtt agttctcacc      960
aacctacata ctcttcggtt ataaatactg tgaggctgaa accaaaggcc actcagtcta     1020
ttcattatta ttcaaaaata tatattgggt ttgtttggtg cagattacag tgacttcaaa     1080
actgtggctc tgcacgacca aactatg                                         1107

<210> SEQ ID NO 10
<211> LENGTH: 1107
<212> TYPE: DNA
<213> ORGANISM: Linum usitatissimum

<400> SEQUENCE: 10
actacctgca aaccaaaaca gattcatggc caagcttatt cccacaaaag ggtccaaaca       60
aaaggaaaat ggtctgattg tctgctaaag tttattgatc agtacgtggg tggatgtttt      120
gttcaccttt acagtgccat tctttaccac agttgttacc agcatcactc atcatcatca      180
gcatcattaa tccttagttt tctatgcact cactttcatt agtgttcact ttgcaattca      240
ataatccatc tattattcga ttgcaaagca agagagttgt aagagtttcg actaagttca      300
aatggagccc aaagtttgat catcagtttg tgaaaacaaa gtcaagctcg tccatatctc      360
tgccttgttc ccaacccact acatagcatc tggaagacct cgtacttcac attctcggac      420
cgaaggacaa ccaataccccc ccttgtgatc ctaaacacat gcacaaatcc ctctgcccga     480
aacttgcccg aacttactcc ctaagaccga tgcccacttg agtcacatga gttgattagt      540
cgatttcacc ctagctcccg cgaactcagc agtgcccgtt gcgactccgc caaatcacta      600
atccttaatt aaaagaacta ataagttgat atcatcacat ttgtggtaac tcatgcatgc      660
acataggttt cctagatacc attgaaggaa gttgccatgt gtttgaatca agatttgcc       720 caccaccatt gatactgaaa ttgaagaacc tagcagccag caacggctcc ttttcatttg      780
tctttcaaca gagcaagtaa caacaaccgt tgcctaaact gaaacccaat aaagagcaaa      840
aaaaaagggg ttgggtggtg taggctagtt tgtctgaaat cagtgtacat tttgcatttc      900
catttactct tctccatcca cttggcatcc tgcattactt cttcttcgtt agttctcacc      960
aacctacata ctcttcggtt ataaatactg tgaggctgaa accaaaggcc actcagtcta     1020
ttcattatta ttcaaaaata tatattgggt ttgtttggtg cagattacag tgacttcaaa     1080
actgtggctc tgcacgacca aactatg                                         1107

<210> SEQ ID NO 11
<211> LENGTH: 4575
<212> TYPE: DNA
<213> ORGANISM: Linum usitatissimum
```

```
<400> SEQUENCE: 11
actacctgca aaccaaaaca gattcatggc caagcttatt cccacaaaag ggtccaaaca      60
aaaggaaaat ggtctgattg tctgctaaag tttattgatc agtacgtggg tggatgtttt     120
gttcaccttt acagtgccat tctttaccac agttgttacc agcatcactc atcatcatca     180
gcatcattaa tccttagttt tctatgcact cactttcatt agtgttcact ttgcaattca     240
ataatccatc tattattcga ttgcaaagca agagagttgt aagagtttcg actaagttca     300
aatggagccc aaagtttgat catcagtttg tgaaaacaaa gtcaagctcg tccatatctc     360
tgccttgttc ccaacccact acatagcatc tggaagacct cgtacttcac attctcggac     420
cgaaggacaa ccaataccc ccttgtgatc ctaaacacat gcacaaatcc ctctgcccga      480
aacttgcccg aacttactcc ctaagaccga tgcccacttg agtcacatga gttgattagt     540
cgattccacc ctagctcccg cgaactcagc agtgcccgtt gcgactccgc caaatcacta     600
atccttaatt aaaagaacta ataagttgat atcatcacat ttgtggtaac tcatgcatgc     660
acataggttt cctagatacc attgaaggaa gttgccatgt gtttgaatca agatttgcc      720 caccaccatt gatactgaaa ttgaagaacc tagcagccag caacggctcc ttttcatttg     780
tctttcaaca gagcaagtaa caacaaccgt tgcctaaact gaaacccaat aaagagcaaa     840 aaaaagggg ttgggtggtg taggctagtt tgtctgaaat cagtgtacat tttgcatttc      900
catttactct tctccatcca cttggcatcc tgcattactt cttcttcgtt agttctcacc     960
aacctacata ctcttcggtt ataaatactg tgaggctgaa accaaaggcc actcagtcta    1020
ttcattatta ttcaaaaata tatattgggt ttgtttggtg cagattacag tgacttcaaa    1080
actgtggctc tgcacgacca aactatgagc cctccaaact caatgagtcc cgccaccaac    1140
ggcagcacca atggtgtggc tatcaatggg gcgaagaagc tactcgattt cgacccgagt    1200
gctgctcccc ctttcaagat tgcagacatc cgtgctgcaa tcccgccgca ttgttgggtg    1260
aagaacccct ggaggtcact cagctacgtc ctgagagacc tcctggtcat cctcagcttc    1320
gccgttgcgg cgacaaagct ggacagctgg actgtctggc ctctctactg gattgctcaa    1380
ggaaccatgt tctgggcagt ctttgttctt ggacatgatt ggtaatttca catgatcttt    1440
ctggtaatgt gggttttctt ttcttattga aaaagattaa aacttttat ctgggctgtt     1500 gcatgcagtg gccatgggag cttctcagac agttggttgt tgaacaacgt gatgggacat    1560
atactccatt cctcaatcct cgtaccttac catggatggt attgtaacta ttgttcgata    1620
ttcgattatg attactgttc tttcagatga agaatctgta ccctaattgt ttttttgttac   1680 caggagaatt agccacaaga cccatcacca gaatcacggc aatgtggaga agatgaatc    1740 ctgggttcca gtaagttgac atgcagtttg ctctaaaatg cagagtcctc tgttttttgt     1800
gtgttcttgt gctttaatgg cgaatgataa tgaaattgaa atttgtaata gctgccggag    1860
aaggtgtaca agagcttgga taccggcacc aagttcatga ggttcaccat ccctctccca    1920
atgtttgcgt atcctatcta cttggtaagt aaacagactg actccaaagt aggaactaat    1980
gacaattttg gacccgacct ggtttggttg actcgggtcg atatgttcg ggtgggtaat      2040 tacccgatct ggcgatgggt gtgcggcgga cattgtcttg ctcgtggtcc accccgctcc    2100
caacccgccc cattcttgac gaaaaagatt tcggaatatg tatcaacaga aaatctagt     2160 ttttatgtta ctagttttct gtatttccat gttttttcct caattctagc cggaatttga    2220
attcaaactg aaatcgggta attccgtcca taacaaaacg gaattgggcc accggtaatt    2280
```

```
agttgaaact aacctcaatt ttggcggaat tggaccggcc atttttttacg tttgcaaacg    2340 gaaaacgttt ttttttttgta aagcgcaaaa tgaaaaacgt atctaagtgg aattattgga    2400
cccatctaga atgggtccat tccaccccca atttcgggct ccaattcatg cccggaaaac    2460
actactgtca tgcattttaa tcttgtatgg ttttaccccca atggatgcag atggatccgg    2520 acgatttttta aaatattatc gggttaaatt taaaaatatc ttaaaactat aagaaaaaaa    2580
taaccaattt taaagaataa aagaactgga cacatatgac gggtgtcgtg gatggatgta    2640
cttgtcccgc tctattaaag gctgataata tacaggtcaa cggtgaatga aggttagatg    2700
cgctattgga tttgaatccg atatgaaatg ataattttgg acacgatctg ttttgggtgg    2760
gtaatatttg atctagggat ggctcgtgct ccaaaccgca ccaaaaccgc ctaattctcg    2820
accaaaaaga ttttatgaat acatatcaac agaaaaatct agttttcatg ttactagttt    2880
tatgtacaac aatattaggt gtcgttttcc cagccttttt cttcaattcc ggccggaatt    2940
cgcattcaaa ccggaattgg atggaatcgg tatacctcgt cacgatgca ttgtcaattc     3000 ctagttagtt tcatggtttt gaaaccaatc aatctattct atatggtttt gattaacagt    3060
ggaggagaag tccggggaag aaagggtcgc atttcaaccc atacagtgac ctgttcgcac    3120
cgaacgagag gacatcggtc atgatttcga cattgtgctg gacagccatg gccttactcc    3180
tctgctactc atcgttcatc tacggcttcc ttccggtctt caaaatctac ggcgtcccctt    3240 atctaatatt cgtggcgtgg ctcgacatgg tgacctacct tcaccaccac gggtacgagc    3300
agaagctgcc gtggtacaga ggcaaagagt ggagctacct acgtggaggg ctgacgaccg    3360
tcgatcgaga ttacggggtc atcaacaaca tccaccatga cattggcacc catgttattc    3420
accatctctt ccctcaaatg ccacactatc accttgtgga agcggtaaac aatttgatta    3480
ttaatttact gttttttgttg ttataatttg agtcgggaga tttccttcct aaatccgatc    3540
cctggtcaat cttggccctt gaatcttcat ataatctaaa aatctagatt aatcaggaac    3600
aatatgatca tgttgtttaa actaattttg ttggaccata acctaccgcc aactgatgga    3660
ccaccgtctc tggttaccgg acccatcatt tccggttacc aagaagtttc tcgatcagtt    3720
ttccggttac tttgacctgc gttgaggaaa attctttcac ccacgtaaac actgtcgtca    3780
actttacgtt tctggaaagt ttttccgatg attggccgta caattttgta csaaagagtt    3840
gtacggatca tataaatgtg tataagtttc tagaaatccg tactgaaata tatacatatt    3900
tgacttttgt ataaagtgta atactaaata ctatactaag tgctgtactc agtatgatac    3960
ttagtacaca catttgtatg actatgaaat gtcaattttg cccttatatt ctcagccgtt    4020
agatctaaga cacagttttt tatacggctga aatttgtggg ggctttgtag atcggatcca    4080
taagtcattt cttcgctcaa gattcggact cgattattaa ctatattatt catcaactct    4140
gacgtttgat gttgcagtcg aagcgactca ggcagcgaag cacgtgctgg ggaagtacta    4200
cagagaaccg aagaaatcag ggcctttccc attccacttg tttgggtact tggtgaggag    4260
cctgggcgag gatcactacg ttagcgatac aggcgacgtc gttttctatc aatctgaccc    4320
acatattccc aagttcccta ccagtgccac caccaagtcc aaatctagct gatgatattg    4380
gctctgatct gatgtatgct gcaggctgtt ttattttgtc ctttgttcgt ttcttttctgc   4440 cagaaacaaa ttctctgttt ctatgtttct ctgtctctcc caccccagct ttctttctga    4500
gtatatcgta taaagtttca agtgattgta agagcagaaa agaaaagaag aagaagaata   4560
ataaagagga ttggc                                                     4575
```

```
<210> SEQ ID NO 12
<211> LENGTH: 20
<212> TYPE: DNA
<213> ORGANISM: Linum usitatissimum
<220> FEATURE:
<221> NAME/KEY: misc_feature
<222> LOCATION: 3, 6, 12
<223> OTHER INFORMATION: n = A,T,C or G
<220> FEATURE:
<221> NAME/KEY: misc_feature
<222> LOCATION: 5
<223> OTHER INFORMATION: n = G or T
<220> FEATURE:
<221> NAME/KEY: misc_feature
<222> LOCATION: 9, 14, 15, 18
<223> OTHER INFORMATION: n = A or G

<400> SEQUENCE: 12
atntnnggna ananntgntg                                         20

<210> SEQ ID NO 13
<211> LENGTH: 20
<212> TYPE: DNA
<213> ORGANISM: Linum usitatissimum
<220> FEATURE:
<221> NAME/KEY: misc_feature
<222> LOCATION: 3, 6, 18
<223> OTHER INFORMATION: n = A,T,C or G
<220> FEATURE:
<221> NAME/KEY: misc_feature
<222> LOCATION: 1
<223> OTHER INFORMATION: n = A or G
<220> FEATURE:
<221> NAME/KEY: misc_feature
<222> LOCATION: 9, 12, 15
<223> OTHER INFORMATION: n = T or C

<400> SEQUENCE: 13
ntnggncang antgnggnca                                         20
```